US012331274B2

(12) United States Patent
Llamazares

(10) Patent No.: US 12,331,274 B2
(45) Date of Patent: Jun. 17, 2025

(54) CONTINUOUS FLOW MICROBIOREACTOR

(71) Applicant: Stamm Vegh Corporation, San Francisco, CA (US)

(72) Inventor: Juan Francisco Llamazares, San Francisco, CA (US)

(73) Assignee: Stamm Vegh Corporation, San Francisco, CA (US)

( * ) Notice: Subject to any disclaimer, the term of this patent is extended or adjusted under 35 U.S.C. 154(b) by 947 days.

(21) Appl. No.: 17/225,307

(22) Filed: Apr. 8, 2021

(65) Prior Publication Data
US 2021/0348096 A1 Nov. 11, 2021

Related U.S. Application Data

(63) Continuation of application No. PCT/US2019/055231, filed on Oct. 8, 2019.
(Continued)

(51) Int. Cl.
| B01L 3/00 | (2006.01) |
| B01F 33/302 | (2022.01) |
| B01F 33/3033 | (2022.01) |
| B01L 7/00 | (2006.01) |
| B33Y 80/00 | (2015.01) |
| C12M 1/00 | (2006.01) |
| C12M 1/34 | (2006.01) |

(Continued)

(52) U.S. Cl.
CPC .............. C12M 23/16 (2013.01); B33Y 80/00 (2014.12); C12M 3/00 (2013.01); C12M 23/44 (2013.01); C12M 29/20 (2013.01); C12M 29/24 (2013.01); C12M 41/46 (2013.01)

(58) Field of Classification Search
CPC ........ C12M 23/16; C12M 3/00; C12M 23/44; C12M 29/20; C12M 29/24; C12M 41/46; B33Y 80/00
See application file for complete search history.

(56) References Cited

U.S. PATENT DOCUMENTS 9,157,550 B2 10/2015 Wheeler et al.
11,718,020 B2 8/2023 Llamazares Vegh et al.
(Continued)

FOREIGN PATENT DOCUMENTS

CN 1678731 A 10/2005
CN 1688686 A 10/2005
(Continued)

OTHER PUBLICATIONS

EP Application No. 19871830.6 Extended European Search Report dated Jun. 9, 2022.
(Continued)

Primary Examiner — Jennifer Wecker
Assistant Examiner — Oyeleye Alexander Alabi
(74) Attorney, Agent, or Firm — Wilson Sonsini Goodrich & Rosati

(57) ABSTRACT

The present disclosure contemplates components, systems and methods for bioreactors that may be employed for producing and maintaining cells, optimizing cell growth and production of products from such cells, and for producing and isolating cells and products made by such cells. The systems, components and methods herein address the scale, cost, efficiency and consistency and are suitable for bespoke cell and bioproduct production.

18 Claims, 55 Drawing Sheets

Related U.S. Application Data

(60) Provisional application No. 62/743,974, filed on Oct. 10, 2018.

(51) Int. Cl.
*C12M 3/00* (2006.01)
*C12M 3/06* (2006.01)
*C12Q 1/6848* (2018.01)
*C12Q 1/686* (2018.01)
*G01N 21/29* (2006.01)

(56) References Cited

U.S. PATENT DOCUMENTS

| | | | |
|---|---|---|---|
| 2002/0173033 A1* | 11/2002 | Hammerick | C12N 5/0062 435/288.5 |
| 2005/0032208 A1 | 2/2005 | Oh et al. | |
| 2005/0175302 A1 | 8/2005 | Ishikawa et al. | |
| 2006/0020392 A1 | 1/2006 | Brokaw et al. | |
| 2006/0091051 A1 | 5/2006 | Takada et al. | |
| 2006/0240548 A1 | 10/2006 | Deutsch et al. | |
| 2008/0032380 A1* | 2/2008 | Kleis | C12M 23/04 435/243 |
| 2008/0306000 A1 | 12/2008 | Zhang et al. | |
| 2010/0116747 A1 | 5/2010 | Franzreb et al. | |
| 2010/0248361 A1 | 9/2010 | Lasky et al. | |
| 2011/0313560 A1 | 12/2011 | Hangaard et al. | |
| 2014/0116881 A1 | 5/2014 | Chapman et al. | |
| 2014/0227769 A1 | 8/2014 | Strobbe | |
| 2015/0343396 A1 | 12/2015 | Aamer et al. | |
| 2016/0279707 A1 | 9/2016 | Mattes et al. | |
| 2016/0312165 A1 | 10/2016 | Lowe, Jr. et al. | |
| 2017/0029968 A1 | 2/2017 | Wadley et al. | |
| 2017/0051243 A1 | 2/2017 | Niazi | |
| 2017/0192717 A1 | 7/2017 | Lee | |
| 2018/0154443 A1 | 6/2018 | Milshtein et al. | |
| 2018/0187139 A1 | 7/2018 | Patel | |
| 2018/0292053 A1 | 10/2018 | Minor et al. | |
| 2018/0369785 A1 | 12/2018 | Fee et al. | |
| 2018/0374262 A1 | 12/2018 | Ezair et al. | |
| 2019/0138670 A1 | 5/2019 | Bandara et al. | |
| 2019/0227526 A1 | 7/2019 | Taber et al. | |
| 2019/0309250 A1 | 10/2019 | Ling | |
| 2019/0339261 A1 | 11/2019 | Lind et al. | |
| 2020/0010788 A1 | 1/2020 | Vellinger et al. | |
| 2020/0023584 A1 | 1/2020 | Portela et al. | |
| 2021/0179993 A1 | 6/2021 | Ginn et al. | |
| 2022/0143610 A1 | 5/2022 | Biz et al. | |
| 2023/0116685 A1 | 4/2023 | Llamazares et al. | |
| 2024/0180198 A1 | 6/2024 | Llamazares Vegh et al. | |

FOREIGN PATENT DOCUMENTS

| | | |
|---|---|---|
| CN | 102112594 A | 6/2011 |
| CN | 103562124 A | 2/2014 |
| CN | 104786508 A | 7/2015 |
| CN | 105259664 A | 1/2016 |
| CN | 106228969 A | 12/2016 |
| CN | 106552560 A | 4/2017 |
| CN | 107532132 A | 1/2018 |
| CN | 109260525 A | 1/2019 |
| EP | 1498475 A1 | 1/2005 |
| JP | 2006189426 A | 7/2006 |
| JP | 2019155279 A | 9/2019 |
| RU | 2340662 C2 | 12/2008 |
| WO | WO-9505944 A1 | 3/1995 |
| WO | WO-2004020590 A2 | 3/2004 |
| WO | WO-2016157027 A1 | 10/2016 |
| WO | WO-2016172350 A1 | 10/2016 |
| WO | WO-2017103863 A1 | 6/2017 |
| WO | WO-2017161210 A1 | 9/2017 |
| WO | WO-2017192717 A1 | 11/2017 |
| WO | WO-2019050842 A1 | 3/2019 |
| WO | WO-2019206207 A1 | 10/2019 |
| WO | WO-2020076852 A1 | 4/2020 |
| WO | WO-2021158529 A1 | 8/2021 |
| WO | WO-2022229381 A1 | 11/2022 |
| WO | WO-2024059658 A2 | 3/2024 |
| WO | WO-2024243043 A2 | 11/2024 |

OTHER PUBLICATIONS

PCT/US2019/055231 International Search Report and Written Opinion dated Feb. 11, 2020.
PCT/US2021/016187 International Search Report and Written Opinion dated Jun. 3, 2021.
Elliott, Olivia et al. Design and Manufacturing of High Surface Area 3D-Printed Media for Moving Bed Bioreactors for Wastewater Treatment. Journal of Contemporary Water Research & Education. Apr. 2017. 160(1):144-156.
EP20210750757.3 Extended European Search Report dated Jan. 24, 2024.
EP20240198520.9 Extended European Search Report dated Jan. 3, 2025.
Fee Conan, et al. 3D-printed porous bed structures. Current Opinion in Chemical Engineering. vol. 18, Nov. 2017, pp. 10-15. DOI:10.1016/j.coche.2017.07.003.
Maskery I., et al. Effective design and simulation of surface-based lattice structures featuring vol. fraction and cell type grading. Materials & Design. vol. 155, Oct. 5, 2018, pp. 220-232. DOI:10.1016/j.matdes.2018.05.058.
Pasko, Alexander et al. Procedural Function-based Modelling of Volumetric Microstructures. Graphical Models 73(5):165-181 (2011).
Pasko, Alexander et al. Procedural Function-Based Spatial Microstructures. Shape Modeling International Conference: 47-56 (2010).
PCT/US2024/029965 International Search Report and Written Opinion dated Oct. 1, 2024.
PCT/US2024/029965 Invitation to Pay Additional Fees dated Jul. 24, 2024.
PCT/US2024/055879 International Search Report and Written Opinion dated Dec. 23, 2024.
Peng Hao, et al. Design, Modeling and Characterization of Triply Periodic Minimal Surface Heat Exchangers with Additive Manufacturing. Solid Freeform Fabrication 2019: Proceedings of the 30th Annual International Solid Freeform Fabrication Symposium—An Additive Manufacturing Conference. Dec. 5, 2019. pp. 2325-2337.
Salmean, Christopher et al. 3D-Printed Stationary Phases with Ordered Morphology: State of the Art and Future Development in Liquid Chromatography. Chromatographia. Published: Dec. 14, 2018. vol. 82. pp. 443-463. https://doi.org/10.1007/s10337-018-3671-5.
Stolaroff, Joshuah K. FEW0233: Additive Manufacturing of New Structures for Heat Exchange. Crosscutting Research Program Portfolio Review Meeting. Lawrence Livermore National Laboratory. Apr. 10, 2019. Pages 1-27. Retrieved from the Internet: URL: https://netl.doe.gov/sites/default/files/2019-05/2019_Annual_Reports/Thursday/MaterialsWaterManagement/C8_3-%2020190411_0900C8_FEW0233_LLNL.pdf.
U.S. Appl. No. 17/759,433 Notice of Allowance dated Mar. 10, 2023.

* cited by examiner

470

401

Module Assembly

Module Assembly
Pairs of parallel planes: A/a; B/b; D/d; E/e
Ten connected planes total 1- Connector support
2- Input 1
3- Output 1
4- Waste 1
5- Waste 2
6- Input 2
7- Output 2
8- SoC Case 1
9- Cleaning Chamber
10- Safety film
11- OM input channel
12- Harvest Channel
13- Filtered OM output
14- Filtered flow
15- Porous membrane
16- Microorganisms
17- Gas flow
18- SoC Case 2
19- Septum A. Media feeding System
B. Media Collector
C. Double Gyroid Layers
D. Culture Collector Tree (1.) Time = 0 s. (2.) Time = 120 s. (3.) Time = 240 s. (4.) Time = 360s.

CONTINUOUS FLOW MICROBIOREACTOR

CROSS-REFERENCE

This application is a continuation of International Application No. PCT/US2019/055231, filed Oct. 8, 2019, which claims the benefit of U.S. Provisional Patent Application No. 62/743,974, filed Oct. 10, 2018, the contents of each of which are incorporated herein by reference in their entirety for all purposes.

BACKGROUND

Production of biological products including cells, proteins, and small and large chemical molecules has become an increasing focus in the provision of medical, food, industrial and other types of products. Consistency of the product and the ability to scale production as well as the flexibility to tailor manufacturing to different locations and for environmental conditions are important factors for production.

Bioreactors provide an environment for large scale production of cells and for producing proteins and other molecules from such cells. Many bioreactors require a large capital investment, as well as require a large physical space. Additionally, the environment of a large bioreactors can differ in environment from smaller scale growth chambers and thereby result in suboptimal growth and production conditions. The larger scale of bioreactors can also make it difficult to investigate growth conditions on an individual cell level. This can result in population heterogeneity of cells as well as affect the quality, purity and yield of bioproducts produced by the cells.

SUMMARY

Provided herein are systems, components and methods for producing and maintaining cells and for producing and isolating cells and products made by such cells. The systems, components and methods herein address scale, cost, efficiency and consistency.

In an aspect, the present disclosure provides for a bioreactor, comprising: an inlet configured to receive a plurality of cells; a plurality of minimodules in fluid communication with the inlet, wherein a minimodule of the plurality of minimodules comprises a double gyroid structure or a modified double gyroid structure, wherein the plurality of minimodules are fluidically interconnected to provide at least one microchannel configured to flow the plurality of cells; and an outlet in fluid communication with the plurality of minimodules, which outlet is configured to direct the plurality of cells or derivatives thereof out of the at least one microchannel.

In some embodiments, the minimodules are interconnected in a manner to provide at least two non-overlapping microchannels each having a constant-mean-curvature. In some embodiments, a first microchannel of the at least two non-overlapping microchannels is configured to flow a liquid medium, and wherein a second microchannel of the at least two non-overlapping microchannels is configured to flow a gas composition. In some embodiments, the at least two non-overlapping microchannels provide liquid. In some embodiments, the at least two non-overlapping microchannels are separated by a porous membrane. In some embodiments, an area of the first microchannel is equivalent to an area of the second microchannel, and wherein the area of the porous membrane is the sum of the areas of the first and second microchannels. In some embodiments, the plurality of minimodules are assembled into a macrostructure. In some embodiments, the macrostructure is selected from the group consisting of a pyramid, a hollow pyramid, a lamella pyramid, a lamella, a chessboard arrangement, and a log. In some embodiments, the plurality of minimodules are arranged in layers within the macrostructure, and wherein the layers are configured such that a velocity of liquid medium in each layer is substantially the same. In some embodiments, the plurality of minimodules are arranged in layers within the macrostructure, and wherein the layers are configured such that a velocity of liquid medium varies throughout the layers. In some embodiments, a liquid medium flowing through the at least one microchannel has a velocity greater than a free fall velocity of a cell flowing through the at least one microchannel. In some embodiments, the bioreactor further comprises a gas input at the base of the macrostructure and a gas output at the top of the macrostructure. In some embodiments, the bioreactor further comprises a cell input at the top of the macrostructure configured to provide the plurality of cells and a cell collection device at the base of the macrostructure configured to harvest the plurality of cells. In some embodiments, the bioreactor further comprises a liquid medium input device configured to flow a liquid medium into each layer of the plurality of minimodules. In some embodiments, a volume of liquid medium provided by the liquid medium device to each layer maintains a substantially constant cell density in each of the layers. In some embodiments, the velocity of liquid media through each minimodule is determined by the cell division rate such that the time for cells to traverses a single minimodule or a layer of minimodules is substantially the same as the cell division rate or proportional to the cell division rate. In some embodiments, the bioreactor is interconnected with a sandbox module. In some embodiments, the bioreactor is interconnected with a cell chip module.

In another aspect, the present disclosure provides systems for cell production, comprising: a first module comprising a cell chip configured to contain a plurality of cells; a second module in fluid communication with the first module, wherein the second module comprises a sandbox bioreactor configured to (i) interface with the cell chip, (ii) direct a subset of cells from the plurality of cells to different segments, wherein cell growth conditions in the different segments are individually configurable, and (iii) iteratively generate a set of growth conditions for the plurality of cells; and a third module in fluid communication with the first module and the second module, wherein the third module comprises a bioreactor configured to (i) interface with the second module, (ii) receive the subset of cells, and (iii) generate copies of the subset of cells under the set of growth conditions.

In some embodiments, the first, second and third modules are fluidically interconnected. In some embodiments, the system further comprises a pump corresponding to each module, wherein the pump is configured to provide liquid medium at a flow rate or pressure for a corresponding module. In some embodiments, the pump is a syringe pump, a peristaltic pump, or a pressure pump. In some embodiments, the system further comprises a component selected from the group consisting of a culture media formulator, an electroporator, a reservoir, a pump, a bubble sensor, a bubble trap, and combinations thereof. In some embodiments, the system further comprises at least one sensor. In some embodiments, the at least one sensor is an in-line sensor. In some embodiments, the at least one sensor measures a biological parameter, a physical parameter, or a chemical parameter. In some embodiments, the biological parameter is selected from the group consisting of cell division rate, cell growth rate, a cell stress response, cell protein content, cell carbohydrate content, cell lipid content, and cell nucleic acid content. In some embodiments, the physical parameter is selected from the group consisting of cell size, cell density, cell flow rate, liquid media flow rate, mixing rate, turbidity, temperature and pressure. In some embodiments, the chemical parameter is selected from the group consisting of pH, liquid media composition, concentration of individual liquid media component, gas composition, and gas concentration, and dissolved gas concentration. In some embodiments, the system further comprises a camera device. In some embodiments, the camera device is configured to count the cells from an output of the sandbox bioreactor or the bioreactor. In some embodiments, the camera device is configured to capture at least one additional parameter associated with individual cells from the output of at least one bioreactor module, and wherein the additional parameter is a biological, chemical or physical feature of a cell.

In another aspect, the present disclosure provides for a cell chip module, comprising: a layered structure comprising at least one fluid circuit; a cell holding area in fluid communication with the at least one fluid circuit, wherein the cell holding area comprises at least one first trap configured to hold a plurality of cells; an inlet port in fluid communication with the layered structure and configured to input a liquid medium into the cell holding area; and an outlet port in fluid communication with the layered structure and configured to collect spent or excess medium and cells.

In some embodiments, the at least one fluid circuit is configured to flow a gas to the cell holding area. In some embodiments, the at least on fluid circuit is configured to flow a liquid medium to the cell holding area. In some embodiments, the at least one trap comprises a suction trap. In some embodiments, the at least one trap comprises a gate trap. In some embodiments, the cell holding area further comprises a second trap. In some embodiments, the second trap is an overflow trap. In some embodiments, the at least one trap and the second trap are in series with one another. In some embodiments, the cell holding area comprises at least one gate trap and two or more overflow traps. In some embodiments, the cell chip module further comprises one or more cells in storage mode. In some embodiments, the storage mode is selected from cells that are dried, lyophilized, frozen, or suspended in liquid. In some embodiments, the cell chip module further comprises one or more physical barriers for distributing cells flowing through the cell chip module.

In another aspect, the present disclosure provides a sandbox bioreactor module comprising a series of segments, wherein a segment of the series of segments comprises at least two microchannels configured to transport at least one cell from one end of a microchannel of the at least two microchannels to the another end of the microchannel of the at least two microchannels, wherein one end of the microchannel is configured to input a liquid media and the at least one cell, wherein the another end of the microchannel is configured to output the liquid media and the at least one cell, and wherein growth conditions in the series of segments are individually configurable.

In some embodiments, a first segment and a second segment of the series of segments are arranged in series such that a cell transits from the microchannel of the first segment to the microchannel of the second segment. In some embodiments, the microchannel of the first segment bifurcates at an output end into at least two microchannels from the second segment, wherein the at least two microchannels are arranged in a parallel configuration such that the cell output from the first segment inputs into one of the at least two microchannels and another cell output from the first segment inputs into another of the at least two microchannels. In some embodiments, the sandbox bioreactor further comprises a first inlet configured to provide liquid medium to the series of segments. In some embodiments, a length of the microchannel is determined by the rate of cell division such that a cell divides zero, once, twice, three times, four times, five times or more than five times during transit from one end of the microchannel to another end of the microchannel. In some embodiments, a diameter of the microchannel is determined by cell size, mixing rate of the transiting liquid, or a combination thereof. In some embodiments, the sandbox bioreactor further comprises at least one sensor for measuring a parameter of the sandbox bioreactor cell environment. In some embodiments, the sandbox bioreactor further comprises a controller configured to alter an input to the sandbox bioreactor in response to the measurement from the at least one sensor. In some embodiments, the parameter is selected from the group consisting of a biological parameter, a physical parameter, and a chemical parameter. In some embodiments, the parameter is selected from the group consisting of gas content, gas concentration, pH, optical density and temperature. In some embodiments, the parameter is selected from the group consisting of cell division rate, cell density, a cell stress response or a cell metabolite. In some embodiments, the sandbox bioreactor further comprises a sample collection chamber at the exit of the microchannel of a final segment in the series of segments. In some embodiments, the sandbox bioreactor is interconnected with a cell chip module.

In another aspect, the present disclosure provides a method of growing and storing cells, comprising: inoculating a cell chip module with at least one cell, wherein the cell chip module comprises a layered structure with at least one fluidic circuit, a cell holding area in fluid communication with the at least one fluid circuit, an inlet port in fluid communication with the layered structure, and an outlet port in fluid communication with the layered structure; providing a liquid medium to the inlet such that the at least one cell remains in a first trap of the cell holding area; incubating the cell chip for a period of time under conditions sufficient to permitting cell division such that divided cells remain in the first trap; after the period of time of cell division, placing the cells in a storage mode.

In some embodiments, the storage mode is selected from the group consisting of drying, lyophilizing, freezing, or suspending in liquid. In some embodiments, the method further comprises providing a new liquid medium to the inlet and incubating the cell chip for a period of time under conditions permitting cell division to reactivate the cell division. In some embodiments, the period of cell division produces sufficient cells such that a substantial number of cells exit the first trap and enter a second trap in the cell chip module. In some embodiments, the cells are further incubated for a second period of time for cell division, and wherein the second period of time produces a sufficient number of cells such that a substantial number of cells exit the second trap and flow to the outlet from the cell chip module for collection. In some embodiments, the cells from the outlet of the cell chip module are provided to an interconnected sandbox or bioreactor module. In some embodiments, the second trap is a suction trap or an overflow trap. In some embodiments, the first trap is a gate trap or a suction trap.

In another aspect, the present disclosure provides methods for selecting cell growth conditions, comprising: introducing first group of cells into a sandbox bioreactor comprising a series of segments, wherein a segment of the series of segments is individually configurable; incubating the first group of cells under a first set of growth conditions in a first segment of the series of segments; monitoring a first parameter of the first group of cells in the first segment; and altering the set of growth conditions to create a second set of growth conditions in a second segment of the series of segments in response to the monitoring of the first parameter in the first segment.

In some embodiments, the first group of cells moves to the second segment, and wherein a second group of cells are introduced into the first segment. In some embodiments, the first group of cells are introduced to the sandbox bioreactor from a cell chip module. In some embodiments, the sandbox reactor is interconnected with a bioreactor module. In some embodiments, the second set of growth conditions is applied to the bioreactor. In some embodiments, a flow rate of cells from one end of each segment to another end is determined by the cell division rate. In some embodiments, the cells divide one time in the period of time that the cells transit from one end of the segment to another end of the segment. In some embodiments, a flow of liquid medium through each segment of the series of segments is laminar flow.

In another aspect, the present disclosure provides methods for scaling production of cells, comprising: introducing a plurality of cells into an inlet of a bioreactor, wherein the bioreactor comprises a collection of minimodules of double gyroid structure or modified double gyroid structure, wherein the minimodules are arranged into layers within a macrostructure comprising an inlet and an outlet; flowing a liquid medium into the bioreactor; supplying a gas composition into the bioreactor; and collecting the plurality of cells from the outlet; wherein the plurality of cells transit between the minimodules, and wherein the plurality of cells transit from the inlet end of the macrostructure to the outlet end of the macrostructure.

In some embodiments, the plurality of cells divides on average one time during the transit from one layer of minimodules to the next layer of minimodules. In some embodiments, an amount of liquid medium flowing to each layer of minimodules maintains substantially the same density of cells in each layer. In some embodiments, a velocity of liquid media flowing through the bioreactor exceeds a free fall velocity of the cells. In some embodiments, the plurality of cells is introduced to the bioreactor from a cell chip or a sandbox module. In some embodiments, a portion of the plurality of cells is collected from the outlet end of the macrostructure. In some embodiments, the plurality of cells produces at least one bioproduct, and wherein the bioproduct is collected from the outlet end of the macrostructure. In some embodiments, the bioproduct is selected from the group consisting of a small molecule, a protein, an antibody, a large macromolecule, and a metabolite.

In another aspect, the present disclosure provides methods for bespoke cell production, comprising: introducing a selected type of cell into a cell chip module; growing the cells in the cell chip module; transiting the cells from the cell chip module to a sandbox bioreactor; and selecting at least one growth condition from a first set of growth conditions in the sandbox bioreactor to generate a second set of growth conditions.

In another aspect, the present disclosure provides methods for culturing cells, comprising: providing a plurality of cells to an adherent bioreactor comprising at least one channel and a microporous membrane; permitting at least a portion of the plurality of cells to adhere to a surface of the at least one channel such that the at least the portion of the plurality of cells replicate on the surface of the at least one channel to generate attached cells; flowing a liquid medium from the at least one channel through the microporous membrane to (i) wash the attached cells, (ii) detach the attached cells to generate suspended cells, (iii) wash the suspended cells; and optionally, collecting the suspended cells.

In some embodiments, the at least one channel comprises a material suitable for adhesion of the at least a portion of the plurality of cells. In some embodiments, the method further comprises flowing an additional liquid medium through the at least one channel to (i) provide a culture medium to permit growth and/or replication of the at least the portion of the plurality of cells, (ii) detach the attached cells from the at least one channel, or (iii) flow the suspended cells from the at least one channel to a collection area. In some embodiments, the adherent bioreactor is in fluid communication with a cell chip module, and wherein the cell chip module provides the plurality of cells to the adherent bioreactor. In some embodiments, the adherent bioreactor is in fluid communication with a bioreactor, and wherein the adherent bioreactor provides the suspended cells to the bioreactor. In some embodiments, the plurality of cells is selected from the group consisting of bacterial cells, fungal cells, yeast cells, eukaryotic cells, plant cells, and algal cells. In some embodiments, the plurality of cells are recombinant cells.

In some embodiments, the method further comprises growing a sample of the selected type of cell in a bioreactor with the second set of growth conditions. In some embodiments, the selected type of cell or a portion thereof are collected from the bioreactor. In some embodiments, the selected type of cell is a chimeric antigen receptor T (CAR-T)cell, a stem cell or a differentiated cell. In some embodiments, the selected type of cell produces at least one bioproduct, and wherein the bioproduct is collected from the bioreactor.

In another aspect, the present disclosure provides a system comprising a plurality of fluid flow paths having a substantially constant cross-section, wherein a first fluid flow path of the plurality of fluid flow paths is in fluid communication with a second fluid flow path of the plurality of fluid flow paths to permit gas flow from the first fluid flow path to the second fluid flow path at a substantially constant rate along the first fluid flow path, and wherein the first fluid flow path is configured to permit cell culture.

In some embodiments, the plurality of fluid flow paths comprises a gyroid structure, a double gyroid structure, a modified double gyroid structure, a triply periodic minimal surface or combinations thereof.

In another aspect, the present disclosure provides methods for processing a plurality of cells, comprising: (a) providing a bioreactor comprising (i) an inlet, (ii) a plurality of minimodules in fluid communication with the inlet, wherein a minimodule of the plurality of minimodules comprises a double gyroid structure or a modified double gyroid structure, wherein the plurality minimodules are fluidically interconnected to provide at least one microchannel; and (iii) an outlet in fluid communication with the plurality of minimodules; and (b) directing a plurality of cells to the inlet, which plurality of cells or derivatives thereof is directed from the inlet through the at least one microchannel to the outlet.

In some embodiments, the bioreactor comprises at least two microchannels. In some embodiments, a first microchannel of the at least two microchannels flows a liquid medium. In some embodiments, a second microchannel of the at least two microchannels flows a gas composition. In some embodiments, the at least two microchannels are separated by a porous membrane. In some embodiments, the plurality of minimodules are assembled into a macrostructure.

In another aspect, the present disclosure provides methods comprising generating a bioreactor comprising: an inlet configured to receive a plurality of cells; a plurality of minimodules in fluid communication with the inlet, wherein a minimodule of the plurality of minimodules comprises a double gyroid structure or a modified double gyroid structure, wherein the plurality of minimodules are fluidically interconnected to provide at least one microchannel configured to flow the plurality of cells; and an outlet in fluid communication with the plurality of minimodules, which outlet is configured to direct the plurality of cells or derivatives thereof out of the at least one microchannel.

In some embodiments, the bioreactor is generated using three-dimensional (3-D) printing of the plurality of minimodules.

In some embodiments provided is a system for cell production comprising a first module comprising a cell chip configured to contain a plurality of cells; a second module comprising a sandbox bioreactor configured to (i) interface with the cell chip, (ii) direct cells from the plurality of cells to different segments, wherein cell growth conditions in the different segments are individually configurable, and (iii) iteratively generate a set of growth conditions for the plurality of cells; and a third module comprising a production bioreactor configured to (i) interface with the second module, (ii) receive the cells, and (iii) generate copies of the cells under the set of growth conditions.

In some embodiments, the first, second and third modules of the system are functionally interconnected. In some embodiments, the system further comprises a pump corresponding to each module, wherein the pump provides liquid media at a flow rate or pressure for the corresponding module. In some embodiments, the pump is a syringe pump, a peristaltic pump, or a pressure pump.

Also provided herein are such systems further comprising a component selected from the group consisting of a culture media formulator, an electroporator, a reservoir, a pump, a bubble sensor, a bubble trap and combinations thereof. In some embodiments, the system also includes at least one sensor, such as an in-line sensor. In some embodiments, at least one sensor measures a biological parameter, a physical parameter or a chemical parameter, which may include, for example, a biological parameter selected from the group consisting of cell division rate, cell growth rate, a cell stress response, cell protein content, cell carbohydrate content, cell lipid content, and cell nucleic acid content; a physical parameter selected from the group consisting of cell size, cell density, cell flow rate, liquid media flow rate, mixing rate, turbidity, temperature and pressure; a chemical parameter selected from the group consisting of pH, liquid media composition, concentration of individual liquid media component, gas composition, and gas concentration, and dissolved gas concentration; and combinations thereof.

Provided herein are such systems that further comprising a camera device. In some embodiments, the camera device counts the cells from an output of the sandbox bioreactor or the production bioreactor. In some embodiments, the camera device captures at least one additional parameter associated with individual cells from the output of at least one bioreactor module, wherein the additional parameter is a biological, chemical or physical feature of a cell.

Also provided herein in some embodiments is a cell chip module comprising a cell holding area comprising at least one first trap for holding cells and optionally at least one second trap for holding cells; an inlet port configured to input a liquid media into the cell holding area; and an outlet port configured to collect spent or excess media and cells. In some embodiments, the first trap may be a suction trap, a gate trap, an overflow trap or a combination thereof. In some embodiments, the first trap and the second trap are in series with one another. In some embodiments, the cell chip module includes at least one gate trap and two or more overflow traps. In some embodiments, the cell chip module can include one or more physical barriers for distributing cells flowing through the module.

In some embodiments, the cell chip module further comprises one or more cells in storage mode, which can be for example, cells that are dried, lyophilized, frozen, or suspended in liquid.

Provided herein in some embodiments is a sandbox bioreactor module comprising a series of segments, wherein a segment of the series of segments comprises at least one microchannel configured to transport a cell from one end of the microchannel to the other end of the microchannel, and wherein one end of the microchannel is configured to input a liquid media and at least one cell, and wherein the other end of the microchannel is configured to output the liquid media and at least one cell.

In some embodiments, of the sandbox bioreactor, a first segment and a second segment are arranged in series such that a cell transits from one of the microchannels of the first segment to one of the microchannels of the second segment. In some embodiments, the microchannel of a first segment bifurcates at an output end into at least two microchannels from the second segment, wherein the two microchannels are arranged in a parallel configuration such that the cell output from the first segment inputs into one of the at least two microchannels and another cell output from the first segment inputs into another of the at least two microchannels.

In some embodiments, the sandbox bioreactor further includes a first inlet suitable for providing liquid media to the segments. In some embodiments, the length of each microchannel the sandbox bioreactor is determined by the rate of cell division such that the cell divides zero, once, twice, three times, four times, five times or more than five times during its transit from one end of the microchannel to the other end of the microchannel. In some embodiments, the diameter of each microchannel is determined by cell size, mixing rate of the transiting liquid or a combination thereof.

In some embodiments, the sandbox bioreactor includes at least one sensor for measuring a parameter of the bioreactor cell environment, and optionally, a controller for altering an input to the bioreactor in response to the measurement from the at least one sensor. In some embodiments, the sensor measures a parameter such as a biological parameter, a physical parameter and/or a chemical parameter, such as gas content, gas concentration, pH, optical density, temperature, cell division rate, cell density, a cell stress response, a cell metabolite or combinations thereof.

In some embodiments, the sandbox bioreactor includes a sample collection chamber at the exit of the microchannels of the final segment in the series of segments. In some embodiments, the sandbox bioreactor is interconnected with a cell chip module, such as any of the cell chip modules described herein.

Provided herein, in some embodiments, is a production bioreactor, comprising a plurality of minimodules, wherein each of the plurality of minimodules comprises a double gyroid shape or structure, and wherein the plurality minimodules are interconnected to provide microchannels. In some embodiments, the interconnection of the minimodules creates two non-overlapping channels each having a constant-mean-curvature. In some embodiments, one microchannel of the production bioreactor provides liquid media and wherein the second microchannel provides a gas composition. In some embodiments, both microchannels provide liquid. In some embodiments, the microchannels are separated by a porous membrane. In some embodiments, the area of the first microchannel is equivalent to the area of the second microchannel, and wherein the area of the membrane is the sum of the areas of the first and second microchannels.

In some embodiments, the production bioreactor may include minimodules that are assembled into a macrostructure, which may be for example, a pyramid, a hollow pyramid, a lamella pyramid, a lamella, a chessboard arrangement or a log. In some embodiments, the minimodules are arranged in levels within the macrostructure and wherein the velocity of liquid media in each level is substantially the same. In some embodiments, the velocity of liquid medium varies throughout the levels. In some embodiments, liquid media flowing through a microchannel has a velocity greater than the free fall velocity of a cell flowing through the microchannel.

In some embodiments, the production bioreactor includes a gas input at the base of the macrostructure and a gas output at the top of the macrostructure. In some embodiments, there is a cell input at the top of the macrostructure and a cell collection device at the base of the macrostructure.

In some embodiments, the production bioreactor includes a liquid media input device, wherein liquid media flows into each level of minimodules. In some embodiments, the volume of liquid media provided by the liquid media device to each level maintains a substantially constant cell density in each of the levels. In some embodiments, the velocity of liquid media through each minimodule is determined by the cell division rate such that the time for cells to traverses a single minimodule or a level of minimodules is substantially the same as the cell division rate or proportional to the cell division rate.

In some embodiments, the production bioreactor is interconnected with a sandbox module, a cell chip module or interconnected to a system that includes both a cell chip module and a sandbox module. Provided herein in some embodiments is a system comprising a plurality of fluid flow paths having a substantially constant cross-section, wherein a first fluid flow path of the plurality of fluid flow paths is in fluid communication with a second fluid flow path of the plurality of fluid flow paths to permit gas flow from the first fluid flow path to the second fluid flow path at a substantially constant rate along the first fluid flow path. In some embodiments, the plurality of fluid flow paths comprises a gyroid shape or structure, a modified gyroid shape or structure, a triply periodic minimal surface or combinations thereof.

Also provided herein are methods of growing and storing cells comprising inoculating a cell chip module with at least one cell; providing a liquid media to a liquid inlet of the cell chip such that the at least one cell remains in a first trap; incubating the cell chip for a period under conditions permitting cell division such that the divided cells remain in the first trap; and after the period of cell division, placing the cells in a storage mode. In some embodiments, the storage mode is selected from the group consisting of drying, lyophilizing, freezing, or suspending in liquid. In some embodiments, the method further includes providing new liquid media to the liquid inlet of the cell chip and incubating the cell chip for a period of time under conditions permitting cell division to reactivate the cell division. In some embodiments, the period of cell division produces sufficient cells such that a substantial number of cells exit the first trap and enter a second trap in the cell chip module. In some embodiments, the cells are further incubated for a second period of time of cell division and wherein the second period of cell division produces sufficient cells such that a substantial number of cells exit the second trap and flow to an outlet from the cell chip for collection. In some embodiments, the cells from the outlet of the cell chip are provided to an interconnected sandbox or production bioreactor module. In some embodiments of the method, the second trap is a suction trap or an overflow trap. In some embodiments, the first trap is a gate trap or a suction trap.

Provided herein are methods of optimizing cell environment comprising introducing first group of cells into a sandbox bioreactor comprising a series of segments; incubating the first group under a first environment in a first segment; monitoring a first parameter of the cells in the first segment; and altering the first environment to create a second environment in response to the monitoring of the first parameter. In some embodiments of the methods, the first group of cells moves to a second segment and wherein a second group of cells are introduced into the first segment. In some embodiments, the cells are introduced to the sandbox bioreactor from a cell chip module. In some embodiments, the sandbox reactor is interconnected with a production bioreactor module. In some embodiments of the methods, the second environment is applied to the production bioreactor.

In some embodiments of the methods, the flow rate of cells from one end of each segment to the other end is determined by the cell division rate. In some embodiments, the cells divide one time in the period of time the cells transit from one end of the segment to the other end of the segment. In some embodiments, the flow of liquid media through each segment is laminar flow.

Also provided herein are methods for scaling production of cells, comprising introducing cells into a production bioreactor, wherein the production bioreactor comprises a collection of minimodules of double gyroid shape or structure, wherein the minimodules are arranged into levels within a macrostructure; flowing liquid media into the production bioreactor; and supplying a gas composition into the production bioreactor; wherein the cells transit between the minimodules; and wherein the cells transit from an inlet end of the macrostructure to an outlet end of the macrostructure. In some embodiments of the methods, the cells divide on average one time during the transit from one level of minimodules to the next level of minimodules. In some embodiments, the amount of liquid media flowing to each level of minimodules maintains substantially the same density of cells in each level. In some embodiments, the velocity of liquid media flowing through the production reactor exceeds the free fall velocity of the cells.

In some embodiments of the methods herein, the cells are introduced to the bioreactor from a cell chip or a sandbox module. In some embodiments, a portion of the cells are collected from the output end of the macrostructure. In some embodiments, the cells produce at least one bioproduct and wherein the bioproduct is collected from the outlet end of the macrostructure, such as for example a small molecule, a protein, an antibody, a large macromolecule, a metabolite, or combinations thereof produced by the cells.

Provided herein are methods for bespoke cell production comprising introducing a selected type of cell into a cell chip; growing the cells in the cell chip; transiting the cells from the cell chip module to a sandbox bioreactor; and optimizing at least one parameter of a first cell environment in the sandbox bioreactor to create a second cell environment. In some embodiments, the method further includes growing a sample of the selected type of cell in a production bioreactor with the second cell environment. In some embodiments, the cells or a portion thereof are harvested from the production bioreactor. In some embodiments, the cells used in the methods are a CAR-T cell, a stem cell or a differentiated cell or combinations thereof. In some embodiments, the cells produce at least one bioproduct and wherein the bioproduct is collected from the production bioreactor.

Provided herein are methods of growing cells comprising growing cells in a cell chip module as described herein. In some embodiments, the method further includes placing the cells in storage mode. Provided herein are methods of optimizing cell environment conditions, comprising growing cells in the sandbox bioreactor as described herein, and optimizing at least one parameter of the cell environment. Also provided herein are methods of growing cells comprising growing cells in a production bioreactor as described herein. In some embodiments, the method is a method of high scale cell production. In some embodiments of the methods for growing and producing cells, the cells are selected from the group consisting of a bacterial cell, a fungal cell, a plant cell, an animal cell, an avian cell, a mammalian cell, a human cell, and a genetically modified cell. In some embodiments, the systems, devices, and methods described herein may be used at zero gravity or under microgravity conditions such that the cells are grown in a zero gravity or microgravity condition.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 3A-3B show example embodiments of a gate trap; FIGS. 3C-3D show example embodiments of an overflow trap; and FIGS. 3E-3F show example embodiments of a suction trap;

FIG. 9A shows an example of a minimodule; FIG. 9B shows an example of minimodule assembly into an example three-dimensional matrix; FIG. 9C shows an example three-dimensional matrix; FIG. 9D shows an example layer of a three-dimensional matrix; FIGS. 9E-9F show example assemblies comprises multiple three-dimensional layers;

FIG. 19A shows an overview of an example connection system comprising a connector between a cell chip module and fluid source; FIG. 19B shows an example connection system with input and output needles; FIG. 19C show example connections made by an example connector system; FIG. 19D shows an example embodiment of a connection system with needles penetrating a chamber in an example cell chip module; FIG. 19E shows an example connection system with needles penetrating a second chamber;

DETAILED DESCRIPTION

Figure 1:
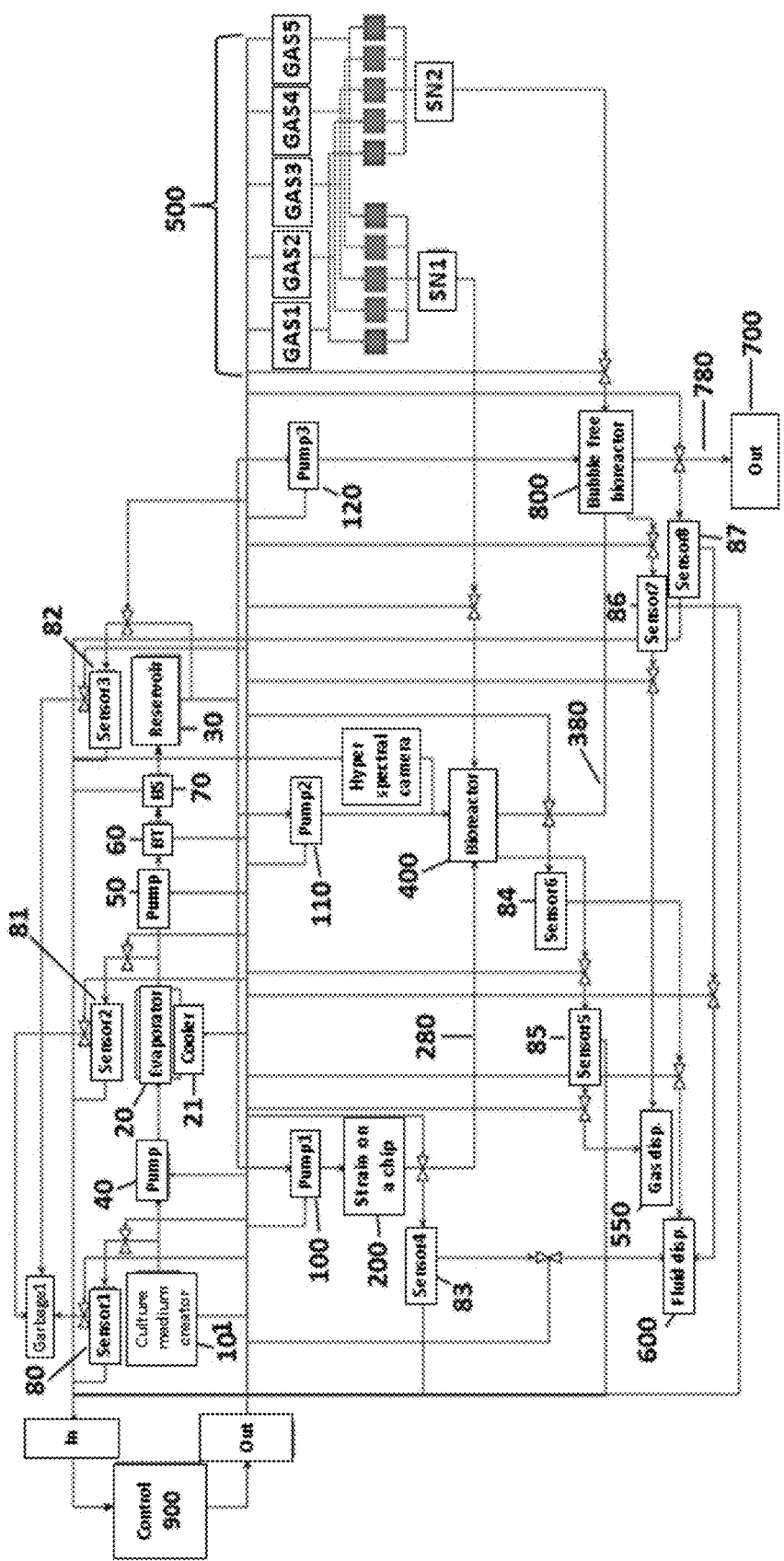
FIG. 1 shows an example embodiment of a system with three modules.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are systems, components and methods for producing and maintaining cells and for producing and isolating cells and products made by cells. The systems, components and methods herein provide flexibility to tailor production for different types of cells, types of cellular environments, and types of molecules produced. The systems, components and methods also provide flexibility of scale. For example, the systems, components, and methods described herein may provide for production scale-up without the altering or significantly altering bench-scale growth conditions.

Included herein in the system and components are one or more bioreactors for growing cells. The bioreactors are on a microbioreactor scale, such that the system can be constructed as a benchtop bioreactor with a capacity to grow and produce cells and/or cell products in both small and large amounts. This system and methods of use are advantageous in their scalability, flexibility, and conservation of resources.

The term "cell chip" or "cell chip module," as used herein, generally refers to a device suitable for growing, culturing and/or storing cells that may include one or more channels or other openings for inputting cells, for providing liquid media and other cell environment factors, and optionally, one or more structures for trapping, containing or directing the flow of cells within the growing/culturing environment of the cell chip or subsections thereof.

The term "sandbox bioreactor," as used herein, generally refers to a device for growing cells and permits testing in an iterative fashion of the impact of one or more cell environment conditions on one or more types of cells. Sandbox reactors may include designs such that the cell environment therein and impacts thereof on the cells are correlative to cell environment and impacts for scale-up and production of cells and bioproducts. A sandbox reactor can include a single testing environment or may be composed of multiple segments within which one or more environment conditions can be tested.

The term "production bioreactor" or "bioreactor," as used herein, generally refers to a bioreactor device suitable for scaling production of cells and/or products produced by cells. A production bioreactor may include one or more channels or other openings for inputting cells, for providing liquid media, gas composition and other cell environment factors and one or more channels for harvesting cells and/or products produced by cells.

The term "culture media formulator," as used herein, generally refers to a component or device for mixing ingredients for use as culture media for growing cells.

The term "trap," as used herein, generally refers to a structure for trapping, containing and/or directing the flow of cells within a physical area. Traps may include, but are not limited to, gate traps, overflow traps, suction traps and porous membrane traps, such as, but not limited to, those described herein. In some embodiments, the trap size is determined by the cell size, volume and/or diameter such that the trap slows, impedes or prevents a cell from moving from one physical space into another physical space. In some embodiments, the ability of a trap to slow, impede or prevent cell movement may be decreased or overcome when the cell number or density increases or when the velocity of cell or liquid media flow is increased.

The term "minimodule," as used herein, generally refers to a segment of a production bioreactor that may be interconnected and assembled into a larger structure (e.g., macrostructure or macroshape) to constitute at least a portion or an entirety of the production bioreactor.

The term "gyroid," as used herein, generally refers to a connected periodic minimal surface containing no straight lines. Such surface may have a mathematically infinite number of connections. In some examples, a gyroid is a unique non-trivial embedded member of the associate family of the Schwarz P and D surfaces with angle of association approximately 38.01°. A gyroid may be configured as a single gyroid or a double gyroid. A double gyroid may be oriented and configured for a particular application in a microfluidic device. The double gyroid may be configured by balancing geometric aspects related to fluid dynamic performances observed in minimodules and macrostructures (e.g., macroshapes), such as the double gyroids crystallographic structure and space group. The gyroid or double gyroid may be implemented in a variety of crystallographic structures.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Bioreactor Modules

In an aspect, the present disclosure provides systems and methods of modular and interconnected bioreactor components for the production of cells. The cells may be bacterial cells, fungal cells, yeast cells, eukaryotic cells, plant cells, or algal cells. The cells may be recombinant cells. A modular system may comprise a first module, a second module, and a third module. The first module may be a cell chip that is configured to contain a plurality of cells. The second module may be in fluid communication with the first module and may be a sandbox reactor. The sandbox reactor may be configured to (i) interface with the cell chip, (ii) direct a subset of cells from the plurality of cells to different segments of the sandbox, and (iii) iteratively generate a set of growth conditions for the plurality of cells. The different segments may be individually configurable. The third module may be in fluid communication with the first and second modules. The third module may comprise a bioreactor configured to (i) interface with the second module, (ii) receive the subset of cells, and (iii) generate copies o the subset of cells under the set of growth conditions. In some embodiments, the third module may comprise a bioreactor and may be in fluid communication with a cell chip module.

The systems, components and methods herein are modular and interconnectable. In some embodiments herein, the system is composed of one or more modules with each module including at least one bioreactor. In some embodiments, the system contains at least one, two, three, or more modules. In some embodiments, the system includes more than three modules. Each module is configured for laminar flow of liquid (including media and/or solvents) and additionally, in some embodiments, unidirectional flow of cells. In some embodiments, one or more modules are configured for transition flow or turbulent flow of liquid (e.g., media and/or solvents).

In some embodiments, the system includes at least 1, 2, 3, or more modules interconnected. In some embodiments, the modules comprise one or more of a cell chip module, a sandbox bioreactor module and a production bioreactor module. In some embodiments, a cell chip module is interconnected (e.g., fluidically connected) to a sandbox bioreactor module such that the cell chip supplies cells to initially seed the sandbox reactor. In some embodiments, a cell chip module is interconnected (e.g., fluidically connected) to a production bioreactor such that the cell chip supplies cells to initially seed the production bioreactor. In some embodiments, a sandbox bioreactor is interconnected (e.g., fluidically connected) to a production bioreactor and cells from the sandbox bioreactor flow into the production bioreactor for scale up. In some embodiments, the system connects a cell chip to a sandbox bioreactor and to a production bioreactor in a series configuration. Alternatively, or in addition to, the system connects a cell chip to a sandbox bioreactor and a production bioreactor in a parallel configuration. Cells can be initially grown in the cell chip, tested for optimal environmental conditions in the sandbox bioreactor and scaled-up in the production bioreactor.

In some embodiments, the system includes a module that is a cell holding and storage chip (also referred to herein as a cell chip) in which one or more cells are input and multiplied through cell growth and division. The cell chip may be a consumable item (e.g., is used once or a few times and discarded). The cell chip may be provided with one or more cell strains. The cell chip may include an input channel for flowing in liquid media and an output channels for flowing spent media and optionally, cells to exit the cell chip. The cell chip may have at least 1, 2, 3, 4, 5, 6, 8, 10, or more input channels. The cell chip may have at least about 1, 2, 3, 4, 5, 6, 8, 10, or more output channels. The cell chip may have an equal number of input and output channels or may have a different number of input and output channels. Each input channel may flow a single component (e.g., a single liquid media) or each input channel may flow a different component (e.g., different types of liquid media). The output channels may flow both spent or excess media and cells. Alternatively, or in addition to, the cells may be separated from the media stream and output from the cell chip by one or more output channels. The cell chip may include at least one mechanism for trapping cells within the module.

In some embodiments, the mechanism for trapping cells is a gate trap which collects cells within the trap as cells flow into the trap with the laminar flow of liquid media within the cell chip. The gate traps may prevent cells from flowing freely within the chip, confining them to a shielded environment, uncoupled from the inertial forces of the flow, while enabling proper access to nutrients and gases. The gate trap may have an inoculation port to enable the seeding of cells within the internal space of the gate trap. The gate trap may have one or more flow protectors shaped as to uncouple the cell within from inertial forces of the flow. Example shapes or structures that can be used as the one or more flow protectors include a triangle, square, a pentagon, a hexagon, a circle and combinations thereof. The flow protectors may be interrupted with openings to allow access of gases and nutrients, and to enable a controlled escape of cells away from the gate trap. In some embodiments, the opening sizes are bigger than the diameter of the cells within the flow protectors. In some cases, the openings size is twice than the cell within the flow protector. In some cases, the openings can be at least 2, 3, 4, 5, 7, or 10 times bigger than the cell diameter within the flow protectors. In some embodiments, the openings are evenly distributed throughout the shape or structure of the flow protectors shape. In some embodiments, the openings are arranged according to the expected flow direction and velocity. In some embodiments, openings may be more abundant on the second half side of the flow protector shape counting in the flow general direction. In some embodiments, the diameter of the gate trap is from about 20 microns to about 1000 microns. In some embodiments, the diameter of the gate trap is about greater than or equal to 30 microns, 40 microns, 50 microns, 60 microns, 70 microns, 80 microns, 90 microns, 100 microns, or more. In some embodiments, the diameter of the gate trap is about 100 microns, 200 microns 300 microns, 400 microns, 500 microns, 600 microns, 700 microns, 800 microns, 900 microns, 1000 microns, or more. In some embodiments, the diameter of the gate trap is less than or equal to about 1000 microns, 900 microns, 800 microns, 700 microns, 600 microns, 500 microns, 400 microns, 300 microns, 200 microns, 100 microns, 90 microns, 80 microns, 70 microns, 60 microns, 50 microns, 40 microns, 30 microns, or less.

In some embodiments, the mechanism for trapping cells is an overflow-type trap. The overflow-type trap, traps may prevent cells from flowing freely within the chip, confining them to a shielded environment, by physically impeding them from escape and leveraging inertial flow forces to enforce their confinement, while enabling access to nutrients and gases. In some embodiments, overflow trap flow protectors include one or more canalized box walls arrange in order to physically confine cell within the trap. In some embodiments the canalized box walls have openings between them. In some embodiment the opening is smaller than the cells diameter within. In some embodiments, the canalized box walls do not have any openings between them. In some embodiments, there is an opening between the roof of the chip and the height of the canalized box walls. In some embodiments the opening between the height of the canalized box wall and the roof is smaller than cell diameter within the trap. When the volume of cells exceeds the capacity of the volume of the gate trap, cells flow out of the trap. In some embodiments, the diameter of the overflow trap is about 50 microns to about 2000 microns. In some embodiments, the diameter of the overflow trap is greater than or equal to about 180 microns or 210 microns. In some embodiments, the diameter of the overflow trap is less than or equal to about 210 microns or 180 microns. In some embodiments, the diameter of the overflow trap is greater than or equal to about 50 microns, 100 microns, 150 microns, 200 microns, 250 microns, 300 microns, 350 microns, 400 microns, 450 microns, 500 microns, 600 microns, 800 microns, 1000 microns, 1200 microns, 1500 microns, 2000 microns, or more. In some embodiments, the diameter of the overflow trap is less than or equal to about 2000 microns, 1500 microns, 1200 microns, 1000 microns, 800 microns, 600 microns, 500 microns, 450 microns, 400 microns, 350 microns, 300 microns, 250 microns, 200 microns, 150 microns, 100 microns, 50 microns, or less.

In some embodiments, the cell trap includes a suction trap. The suction trap may be designed by vertically separating a liquid media area from a cell growth area with a porous membrane. The suction trap may be designed to have one or more arms where the cells are input and where the cells grow and divide. The liquid media travels through the chip and can cross the porous membrane to the lower area, whereas the cells remain in the upper area due to the pore size being smaller than the cell size. The movement of the liquid media from the upper to lower level creates a suction which retains the cells within the one or more arms. When the cells divide to a certain number or density, the suction no longer maintains all of the cells within the arms, and cells can flow on the upper level out of the arms and towards the output port of the cell chip. A suction trap may have at least 1, 2, 3, 4, 5, 6, 7, 8, 9, 10 or more arms. In some embodiments, the porous membrane used may vary according to the cell type. In some embodiments, the porous membrane may have a pore size smaller than the cell diameter. In some embodiments, the pore size of the porous membrane may be greater than or equal to 0.22 microns, 1 micron, 3 microns, 5 microns, 7 microns, or more. In some embodiments, the pores size is less than or equal to about 7 microns, 5 microns, 3 microns, 1 micron, 0.22 microns, or less. In some embodiments the porous membrane used has discrete holes of the specific pore size chosen; this can be achieved by the implementation of track-etched techniques. In some embodiments, the pores of the porous membrane are randomly distributed. Alternatively, or in addition two, the pores may be arranged or patterned. In some embodiments the material used for the porous membranes is high-quality polycarbonate films. In some embodiments, the material used for the porous membranes is polysulfone, polyethylene, polytetrafluoroethylene, polypropylene, nitrocellulose, nanocellulose, nylon, ceramic foams, or carbon nanotubes.

In some embodiments, the mechanism for trapping cells in the cell chip includes a combination of trap types, including gate traps, suction traps and overflow traps. In some embodiments, the trap types are in series, so that as cells are released from one type of trap, they flow into and our trapped in another type of trap. Alternatively, or in addition to, the traps may be arranged in a parallel configuration. In some embodiments, the traps are arranged in both a series and parallel configuration. The number and arrangement of traps can be tailored for the types of cells as well as the size and volume of cell chip and rate of liquid flow in the cell chip. In some embodiments, the cell chip contains greater than or equal to 1, 2, 3, 4, 5, 10, 20, 50, 100, or more gate traps alone or in combination with one or more overflow traps or in combination with one or more suction traps. In some embodiments, the cell chip contains greater than or equal to about 1, 2, 3, 4, 5, 10, 20, 50, 100, 250, 300, 400, 500, 1000 or more overflow traps alone or in combination with one or more gate traps or one or more suction traps.

In some embodiments, the mechanism for trapping cells is a porous membrane trap. This type of trap has liquid media flow on the upper side of a porous membrane and cells are input and grow in a chamber below the porous membrane. As media perfuses into the cell chamber and as the density of cells increases and cells grow closer to the membrane, cells are pulled through the pores of the membrane into the upper media lane, where the cells can then move with the liquid media flow, thereby exiting the trap. The pore size of the membrane in the trap can be tailored for the type and size of cells. In some embodiments, the pore size is from about 0.22 micron to about 5 microns. In some embodiments, the pore size is greater than or equal to about 0.22 microns, 1 micron, 3 microns, 5 microns, 7 microns, or more. In some embodiments, the pore size is less than or equal to about 7 microns, 5 microns, 3 microns, 1 micron, 0.22 microns, or less. The size and volume of the chambers below the membrane can be tailored for the type and size of cells. The number of cell chambers can be tailored for any throughput. In some embodiments, the number of cell chambers is greater than or equal to 1, 2, 3, 4, 5, 10, 25, 50, 100, 250, 500, 1000 or more.

In some embodiments, after cells are grown in the cell chip, the cell chip stores the cells trapped therein for later use. Cells can be stored by a variety of approaches, including, for example, freezing, drying, lyophilizing or storage in liquid media or a liquid media modified to enable cell storage at room temperature or at other temperatures.

In some embodiments, the system includes a sandbox bioreactor. The sandbox reactor may be a consumable item (e.g., is used once or a few times and discarded). Alternatively, or in addition to, the sandbox reactor may not be a consumable item. The sandbox bioreactor module is made up of a series of segments where each segment has at least one microchannel suitable for transit of a cell from one end of the microchannel to the other end of the microchannel. In some embodiments, a segment has two or more microchannels that function in parallel to one another, such that a cell in one microchannel may not transit to another microchannel within the same segment. In some embodiments, a segment has greater than or equal to 2, 4, 8, 16, 32, 64, 128 or $2^n$ microchannels in parallel. The length and diameter of a microchannel can be tailored for the cell type, cell size and rates of transit of the cell and liquid media in the microchannel. In some embodiment channel may have a diameter of greater than or equal to about 20 microns, 50 microns, 70 microns, 120 microns, 200 microns, 600 microns, 1500 microns, 2000 micron and a length of or of about 1 millimeter, 2 millimeters, 4 millimeters, 10 millimeters, 22 millimeters, 40 millimeters, 120 millimeters, 200 millimeters, or more. In some embodiments, the length of a microchannel is tailored to the cell division rate of a cell transiting through the microchannel such that the cell divides once during the transit time from entering to exiting the microchannel. The diameter of each microchannel can be tailored to cell size, mixing rate of the transiting liquid, rate of gas exchange or a combination thereof.

In some embodiments, a segment of the sandbox bioreactor comprises two or more sections. One section may comprise a mixing module and another section may comprise a growing chamber. The mixing module and growing chamber may be in series or parallel configuration. In an example, the mixing module and growing chamber are in a series configuration. The mixing module may be fluidically connected to greater than or equal to 1, 2, 4, 6, 8, 10, or more input channels. The input channels may include a channel that flows media, gas, and/or cells. In an example, the mixing module is fluidically connected to two input channels such that one channel provides media and another channel provides cells to the mixing module. The media and cells may mix in the mixing module. The mixing module may comprise a straight channel or may comprise a channel with a serpentine or tortuous geometry. The diameter of the channel of the mixing module may be greater than or equal to about 20, 50, 70, 120, 200, 600, 1500, or 2000 microns and a length of or of about 1, 2, 4, 10, 22, 40, 120, 200 millimeters. The mixing module may provide the mixed cells and media to the growing chamber. The growing chamber may include an expansion zone that increases the diameter of the segment. The growing chamber may have a diameter that is greater than or equal to 20, 50, 70, 120, 200, 600, 1500, or 2000 microns and a length of or of about 1, 2, 4, 10, 22, 40, 120, or 200 millimeters.

In some embodiments, the sandbox bioreactor has two or more segments placed in series with one another such that a cell from a microchannel of one segment flows into a microchannel of the next segment. In some embodiments, a microchannel from a first segment is interconnected to two microchannels within a second segment placed in series with the first segment. The length of the microchannel of the first segment is tailored so that the cell divides at most once during the transit time from entering to exiting the first microchannel, and so that the two cells produced from such division are separated and flow separately into the two microchannels of the second segment. The two microchannel of the second segment may be arranged in a parallel configuration. In some embodiments, second segment microchannels are interconnected in a similar manner with microchannels of a next segment in series. In some embodiments, the cells do not divide during their transit through each microchannel. In other embodiments, the cells can divide greater than or equal to 1, 2, 3, 4, 5 or more times during the period in which they transit the length of the microchannel. Segments can be placed in series of greater than or equal to 2, 3, 4, 5, 6, 7, 8, 9, 10 or more segments, each segment containing one or more microchannels. Where microchannels interconnect from one segment to the next segment and partition dividing cells as they transit from microchannels of one segment to the next, the number of microchannels may increase by factors of $2^n$, where n=1, 2, 3, 4, 5, 6, or greater than 6.

The sandbox bioreactor may permit testing and measurement of the impact of varying environmental conditions on a cell. Varying environmental conditions can include variations in media components, pH, temperature, gas composition, gas exchange, cell density, cell flow, and/or flow rate for liquid media. In some embodiments, the sandbox bioreactor has an inlet to the first segment through which liquid media is provided and flows through the first segment into the downstream segments connected in series and/or parallel. The composition and/or flow rate of the media can be changed over time or can remain constant.

The sandbox bioreactor may include one or more sensors and/or one or more sample collection devices. The sensors and/or sample collection devices may be used to monitor cellular responses to changes in the environment. In some embodiments, one or more sensors are in-line sensors. In some embodiments, the sensors are off-line and receive a sampling of cells, media or a combination thereof. The sensor can measure a biological, physical and/or chemical parameter. Example parameters include pH, cell division rate, cell growth rate, cell density, temperature, optical density, gas composition, and/or gas exchange rate. Example parameters also include profiling, single species identification and quantification of one or more of a cellular metabolite, protein, nucleic acid, lipid, small molecule, or biologic molecules or combinations thereof. In some embodiments, a sensor measures a cell stress response and a cell metabolite as a response to a change in environment.

The sandbox reactor may further comprise one or more controllers. The controllers may control the cell environment in one or more segments of the sandbox bioreactor. In some embodiments, the controller is in communication with and/or receives information from one or more sensors related to the cells, cell environment or a combination thereof within the one or more segments of the sandbox bioreactor. The controller may make changes to the cell environment in response to the information from the one of more sensors. Example changes include liquid media flow rate, liquid media component concentrations, pH, temperature, gas concentration, gas content, and cell density.

In some embodiments, the system includes a production bioreactor module. The production bioreactor provides an environment for scaled-up growth and production of cells and/or bioproduct from cells. The production bioreactor provides a 3-D structure comprised a multiple minimodules. The production bioreactor may include greater than or equal to 1, 2, 4, 6, 8, 10, or more minimodules. The minimodules create a series of channels and chambers for the growth and movement of cells and for the flow of liquid media, gasses and bioproduct. The minimodules of the production bioreactor can include shapes such as double gyroid, modified double gyroid, or any shaped that may be described as a triply periodic minimal surface (TPMS), This type of surface forms a lattice system that can grow on all three axes (X, Y, Z) periodically. TPMS may be free of self-intersections and divide a given volume into two (or more) independent sub volumes. A self-intersection may comprise a surface with a single normal vector per point defining the surface. If the surface divides the volume in which it is circumscribed into two independent and congruent sub volumes, this surface is called a balanced surface. TPMS are described in terms of a fundamental patch or asymmetric unit from which the entire surface may be built up by its symmetry elements. The minimodules may be fluidically connected (e.g., interconnected) with one another such that gasses, media, and/or byproduct can flow from one minimodule to another minimodule.

In some embodiments, the minimodules of the production bioreactor may include a double-gyroid or modified double-gyroid shape. A double gyroid (DG) may comprise two gyroids, and may include two intergrown nonoverlapping domains. A modified double gyroid (DG) may include two intergrown nonoverlapping domains, which may be bounded by two constant-mean-curvature (CMC) surfaces separated by a matrix phase. A modified double gyroid structure may comprise minor modifications to the connections of a non-modified double gyroid in order to adapt the structure to a given macrostructure or function. Modifications may include blocking of a portion of the connections or intersections (e.g., 'mouths'), modifying the diameter of one or both phase channels of the structure, or complete or partial elimination of any of the phase channels present in a DG structure. A DG or modified DG may include a first gyroid structure intertwined with a second gyroid structure. The two channels may be separated by a porous membrane (matrix phase). The matrix phase can diffuse gas molecules in a manner that may be based at least in part on a specific pressure and gas composition. When both liquid and gaseous components microchannel radius are equal, the matrix phase surface can be equal to the sum of these. The two CMC surfaces create two continuous channels when multiple DG's are interconnected (e.g., fitted together). These two channels create two nonoverlapping channels for the flow of liquid media and/or gas. The porous membrane may provide a surface on which certain cell types can adhere and grow. In some embodiments, one channel provides liquid media throughout the production bioreactor. In some embodiments, both channels provide liquid. In some embodiments, one channel provides liquid media and the other channel provides gas to the production bioreactor. In some embodiments, the diameter of the microchannel of the minimodules can vary as required for specific cell types, production requirements and the like. In some embodiments, the minimodules can have a regular cubic wrap structure having a length "L" of its edge. L can be related to the sweeping diameter. In some embodiments, L is equal to the two thirds of the sweeping diameter of a microchannel, times the square root of two, times the square root of three. The total surface and volume of the microchannels corresponding to the liquid component can be equal to the corresponding dimensions of gaseous component if the radius of both components is the same within a minimodules. In some embodiments, the radius of the components can be different. In some embodiments when both radii are equal, the microchannel radius cannot be greater to 0.7 times the sweeping radius. The shortest distance between two minimodules of two different faces is equal to the sweeping radius times the square root of two, minus the addition of each component channel radius.

In some embodiments, the area of the first channel with a DG is equivalent to the area of the second channel within a DG, and wherein the area of the matrix phase is the sum of the area of the first channel and the area of the second channel.

The distance between the matrix phase separating the channels and the center of each channel is a constant. The rate at which media and gas flow through the production module can be determined by the selected cell type and cell density, as well as stress conditions to be generated on the cells. The rate of gas diffusion through the matrix into the liquid media is determined by the gas composition and the pressure of gas in the gas channel formed by the structures as well as the membrane thickness and the material selected for manufacturing the channels and surrounding areas. The gas flow rate and working pressure may be related to culture cell density. In some embodiments, the gas flow may be equal to the gaseous component volume per minute. In some embodiments, the gas flow is greater than or equal to about 2, 3, 5, or 10 times the gaseous component volume per minute. In some embodiments, the working pressure may vary from about 1 atmosphere (atm) to 5 atm. In some embodiments, the working pressure is greater than or equal to 1 atm, 2 atm, 3 atm, 4 atm, 5 atm, or more.

One advantage of the DG is the mitigation of gravitational forces that may, in other structures, provide an uneven exposure to media and for gas exchange. The shape creates a three-dimensional (3-D) laminar forces such that the variation in distance of any one cell to a structural wall is averaged out to provide a more constant and even exposure among the cell population. Additionally, the DG shape avoids stagnant areas of liquid or gas, where flow may not occur or may be interrupted. This allows for the use of higher throughput through the bioreactor with lower velocities and results in lower sheering stress on the cells. In some embodiments, the average velocity can be greater than or equal to about 1 micron/second, 3 microns/second, 5 microns/second, 10 microns/second, 15 microns/second, 20 microns/second, 50 microns/second, 100 microns/second, 200 microns/second, or more. The DG structures provide better diffusion of media and gases as compared to other bioreactor systems. In some embodiments, the velocity of the liquid media flowing through the channel within a DG is greater than the free fall velocity of cell flowing through the same channel.

The DG structures provide increased surface area over many shape options, and this increased surface area provides surface area for cell growth as well as improvements in liquid media flow, mixing and gas exchange. When L equals L1, the surface of each component can be described as $Y=3258.6 \cdot XE(-1)$, where Y is square millimeters/microliter and X equals the radius defined by L1.

The minimodule DG structures are fitted together into a macrostructure or macroshape that makes up the production bioreactor. In some embodiments, the macrostructure is a pyramid. In some embodiments, the macrostructure is hollow pyramid, a lamella pyramid, a chessboard arrangement or a log. The macrostructure and number of minimodules within the production bioreactor can be tailored to cell division rate of the cells to be grown, as well as to regulate the velocities of liquid media, gas exchange and cell movement through the bioreactor. Each macrostructure can provide different possibilities to interact with cells, and it may be chosen given the specific process the production bioreactor is intended to stimulate. Pyramid and hollow pyramid macrostructure enable a suitable environment for growth while keeping constant velocities and cell density. More sensitive strains may require more interventions over time, in which case hollow pyramids may provide that capacity. Lamella pyramids enable a suitable environment for growth and development, by keeping both velocity and density constant while providing complete access to each cell at each moment in time, enabling direct intervention and treatment. The chessboard and log arrangements may also provide complete access to every cell at every point of the process while permitting control over homogenous velocity and density. In some embodiments, cells are inputted at the top of the macrostructure and a cell collection device at the base of the macrostructure.

The arrangement of the DG minimodules into a macrostructure provides a mechanism for determining and optimizing liquid media and gas flow within the bioreactor. In some embodiments, the macrostructure is comprised of layers or levels of the minimodules. In some embodiments, the minimodules are arranged in levels or layers and the velocity of liquid media in each level is substantially the same. Alternatively, or in addition to, the velocity of the liquid media in each level or layer may vary. For example, the velocity of the liquid media may increase or decrease between levels or layers. The velocity of the liquid media may vary from minimodule to minimodule or may be substantially the same between minimodules. In some embodiments, the production bioreactor further comprises a liquid media input device. The liquid media device may be structured to provide liquid media to each level of minimodules within the macrostructure. In some embodiments, the volume of liquid media provided to each level maintains a substantially constant cell density in each of the levels. Microchannel radius may be linked to the radius of the cells, cell density or to other parameters (e.g., filamentous arrangements, chain arrange, etc.). In some embodiments, cell density can vary from $1\times10^6$ cells/ml to $1\times10^{12}$ cells/ml. In some embodiments, the velocity of the liquid media through each minimodule is determined by the cell division rate such that the time for a cell to traverse a single minimodule or level of minimodules is substantially the same as the cell division rate or is proportional to the cell division rate so that the cell divides greater than or equal to 1, 2, 3, 4, 5, or more than 5 times during the transit. In some embodiments, a first level has x volume of liquid media such that with a given number of cells, the density in X, and a second level with a 2× volume of liquid media, and in the duration the cells transit from the first level to the second level, the number of cells doubles (e.g., each cell divides on average one time) so that the density in the second level remains X (i.e. a constant cell density between the levels).

Additional optimization can be achieved by determining the expected number of cells at the base of the macrostructure, the terminal end of the macrostructure where the cells and/or bioproduct arrive before exiting the structure through the output to a collection container. Expected cell number also can be determined for the different levels of the macrostructure. Based on the expected cell number at the base and different levels, the flow of gas and liquid media can be adjusted for each level to compensate for the increased gas and liquid media requirements as the number of cells increase through cell division, cell movement and cell accumulation as they progress through the bioreactor towards the base of the structure.

Liquid Media Supply

In some embodiments, the system includes one or more components to supply liquid media to the one or more modules. Components can include one or more of a culture media formulator, an electroporator or other sterilization device, a reservoir, a pump, a bubble sensor and a bubble trap. The culture media formulator generates the liquid media for one or more modules by mixing the components of the media, and water as appropriate for the cells to be grown in the modules. An electroporator can be interconnected to the media generator to clean the media and provide a sterile starting media for supply to the one or modules for growing cells. A bubble sensor and bubble trap can be included to detect and remove any gas bubbles in the liquid media introduced in media generation or cleaning.

The system can also include one or more reservoirs for holding reserve media before supplying it to a module. In some embodiments, the system includes at least 2, 3, 4, 6, 8, 10, or more reservoirs. The reservoirs can be filled asynchronously, so that one reservoir fills while another, already fully filled, is used to supply the one or more modules with liquid media. The separation of reservoirs in this manner is additionally advantageous to isolate the cell growth modules of the system from any connection to electrical current. The reservoir being filled has any exposure to electrical current that may flow from upstream components such as the electroporator. The filled reservoir is isolated from electrical current flow such that it cannot transmit current to downstream components and modules. In some embodiments, the volume of the reservoir may be linked to throughput of the production bioreactor over the division time of cell chosen for the process. In some embodiments, multiple reservoirs may be installed in parallel and uncoupled from each other. In some embodiments, multiple reservoirs may be installed in series.

The liquid media supply components can also include one or more sensors. The sensors can measure parameters including pH and temperature of the media. A sensor may be an in-line sensor or may be connected to a sampling device that samples media intermittently from one ore components of the liquid media supply. The supply system can provide liquid media at a range of rates dependent on the use, scale and operation of the system. In some embodiments, the liquid media supply can provide from about 100 microliters to about 1000 liters per hour to one or more of the downstream modules. In some embodiments, the liquid media supply provides from about 0.5 liter to 1000 liters per hour to one or more of the downstream modules. In some embodiments, the liquid media supply provides from about 0.5 liter to 5 liters per hour to one or more of the downstream modules. In some embodiments, the liquid media supply provides from about 10 liters to 80 liters per hour to one or more of the downstream modules. In some embodiments, the liquid media supply provides form about 100 liters to 1000 liters per hour to one or more of the downstream modules.

The liquid media supply components may include one or more pumps for flowing media from a reservoir or media formulator to a downstream component such as a cell chip, sandbox bioreactor or production bioreactor. The system may include greater than or equal to 1, 2, 3, 4, 6, 8, 10, or more pumps. The pumps may be the same type of pump or may be different types of pumps. Example pumps include a syringe pump, a peristaltic pump, and a pressure pump. The liquid media supply system is configured to provide unidirectional flow through to the downstream component. In some embodiments, the pump is a syringe pump that is used to supply media to the cell chip. In some embodiments, the pump is a syringe pump that is used to supply media to the sandbox bioreactor. In some embodiments, the pump is a peristaltic pump used to supply media to the production bioreactor. In some embodiments, the system includes three pumps, two syringe pumps, supplying the cell chip and the sandbox reactor and a peristaltic pump supplying the production bioreactor. The pumps may work synchronously or individually. In some embodiments, all three pumps work synchronously. The one or more pumps supply media with a high degree volume and rate accuracy to the downstream modules. In some embodiments, the accuracy is within 1, 2, 3, 4 or 5 nanoliters.

Gas Supply and Composition

The system herein is compatible for use with cells that require a specific gas composition, such as cells which require oxygen to grow and survive. The materials for use in constructing the bioreactor modules can include glass, acrylic, collagen, polydimethylsiloxane (PDMS), poly(ethylene glycol) (PEGDA), Poly(D,L-Lactide), and other biocompatible polymers that allow for oxygenation of the media. In some embodiments, the system includes a controller which controls the diffusion of oxygen and other gas solutions in one or more modules. A gas solution is formulated out of pure component gases, such as from gas storage tanks or other supply mechanisms, to establish a mixture or pure gas solution at various concentrations and flow rates. Alternatively, or in addition to, the gas mixture may be provided by a purified air mixture. Gas solution can be used to provide an aeration environment and control pH, as well as to provide carbon, nitrogen, phosphorus and sulfur to the liquid phase. In some embodiments, the system has more than one gas controller or mechanism such that different gas solutions can be provided to different modules within the system.

Sensors and Monitoring of Environment

In some embodiments, the one or more bioreactor modules are interconnected with one or more sensors that monitor one or more features of the environment. The sensors can be placed at specific points within the module or system. Measurements are taken over specific time frames and at specific time points such that the sensor monitors a specific group of cells. In some embodiments, one or more sensors trace a feature for a specific group of cells as they move through the bioreactor module. The sensor can trigger a specific treatment in response to the measurement to optimization conditions for the specific group of cells. Example measurement and optimization of features include pH, oxygen diluted, overall gas composition, dilution of other gases, temperature, cell density, sugar profile, transcriptomics and targeted transcript monitoring, metabolomics and proteomics. In some embodiments, the feature is measured at least 1, 2, 3, 4, 6, 8, 10, or more time points. In some embodiments, the feature is measured for a specific group of cells and can be timed to monitor the group as it moves through the module of the bioreactor and from module to module.

In some embodiments, at least one sensor measures a parameter such as a biological parameter, physical parameter or chemical parameter of cells within, traveling through, entering and/or exiting a bioreactor module. In some embodiments, at least one sensor measures a parameter such as a biological parameter, physical parameter or chemical parameter of the cell environment within a bioreactor module. Example biological parameters include cell division rate, cell growth rate, a cellular stress response, cell protein content, cell carbohydrate content, cell lipid content and cell nucleic acid content. Example physical parameters include cell size, cell density, cell flow rate, liquid media flow rate, mixing rate, turbidity, temperature and pressure. Example chemical parameters include pH, liquid media composition, concentration of individual liquid media components, gas composition, gas concentration and dissolved gas composition.

In some embodiments, the system or module is in communication with a camera device. The camera monitors the output of at least one bioreactor module. The camera may capture a biochemical, physical or chemical feature of the bioreactor output. In some embodiments, the camera device captures information such as cell count, cell velocity, and cell density. In some embodiments, the camera is an inverse spectral camera which captures information across a range of wavelengths. In some embodiments, the camera device captures information from the output of two or more bioreactor modules.

Methods of Use

Figure 8:
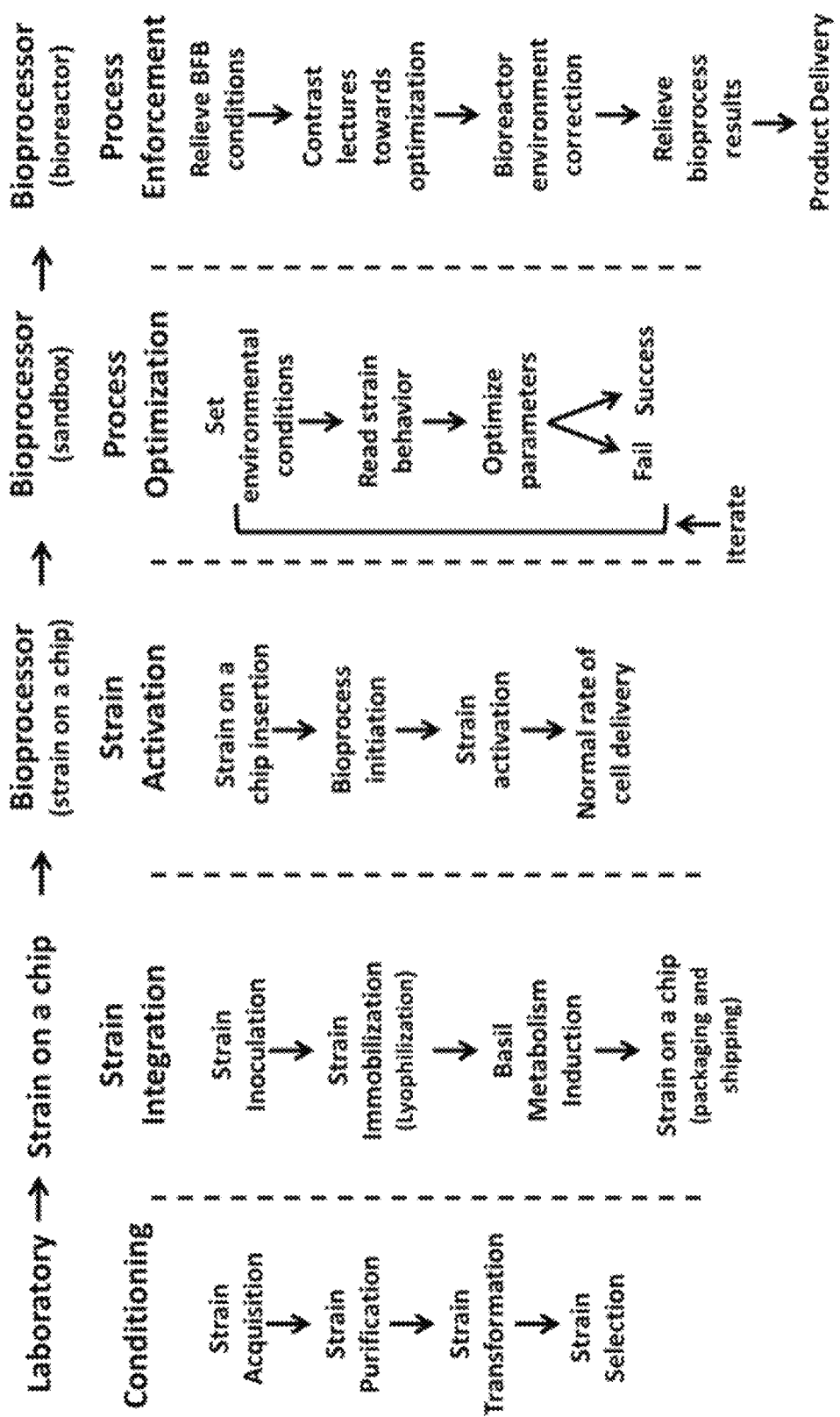
FIG. 8 shows schema for example methods of cell growth, storage, environment optimization and scale-up production.

In some embodiments herein, one or more modules is utilized to produce cells. FIG. 8 shows an example method for utilizing one or more modules to produce cells. The cells can be collected through the output channel of a module. In some embodiments, cells are collected within the module and stored in the module, such as storage of cells within a cell chip module. In some embodiments, one or more modules is utilized to produce a bioproduct from the cells, such as a small molecule, protein, antibody, metabolite or other product produced by the cells grown in the module. The bioproduct can be collected through the output channel of a module and separated from the growing cells, such as by diffusion through a porous membrane or by filtration. In some embodiments, the bioproduct is internal to the cell. To harvest the bioproduct, the cells are collected, lysed and the bioproduct can then be further purified. In some embodiments, the bioproduct is secreted from the cells and can be collected without harvesting or lysing the cells.

The bioreactor modules and systems herein can be utilized to produce specific cell types and has the flexibility to be utilized to grow a variety of cell types. In some embodiments, a cell chip module is utilized to provide a particular type of cells to a sandbox bioreactor, to a production bioreactor or to a sandbox module in series with a production module. The cell chip module allows for bespoke cell production and environment optimization.

The cell chip can accommodate production of stem cells and other types of cell therapies including autologous and allogeneic productions. The cell chip can accommodate production of stem cells and other types of cell therapies including autologous and allogeneic productions. In some embodiments, it can be carried out the expansion, gene delivery, or activation oft-cells for personalized chimeric antigen receptor T cell (CAR-T) treatments. In some embodiments stem cells can be undifferentiated, grown, and/or differentiated.

In some embodiments, the cells to be grown in the system are prokaryotic cells, such as bacterial cells. In some embodiments, the cells grown are eukaryotic cells, such as a yeast cell, fungal cell, algae cell, plant cell, avian cell, or mammalian cell. The cells can be free-floating in culture or can be adherent cells, that adhere to one or more surfaces within the bioreactor. The cells can be transformed or otherwise engineered to produce a bioproduct such as a heterologous protein, small molecule or metabolite.

In some embodiments, the systems, devices, and methods described herein may be used at zero gravity or under microgravity conditions such that the cells are grown in a zero gravity or microgravity condition.

Methods for Constructing Bioreactor Modules

The systems, components and modules herein can be fabricated from a variety of materials and such materials can be tailored depending on the cells grown and cell environments employed. In some embodiments, components and modules or parts thereof are fabricated by 3-D printing. The printing can employ commercially available resins and ultra-violet (UV) curable biocompatible polymers. In some embodiments, each minimodule shape is discretely designed in a virtual environment. In some embodiments, components and modules are provided by commercially available components that are combined and arranged together as described herein. In some embodiments, the biomaterial used may include a combination of three subcomponents, a biocompatible polymer, a photoinitiator and UV absorber.

Devices and systems of the present disclosure may be formed by 3-D printing, such as, for example, stereolithography. In some examples, a computer-aided manufacturing (CAM) or computer-aided design (CAD) model of a device of the present disclosure is provided to a 3-D printing system that employs stereolithography, comprising providing a container having a resin comprising a photoinitiator and one or more polymer precursors. An ultra-violet (UV) laser may be used to draw a pre-programmed design or structure into the surface of the container having the resin. The resin may be a photopolymer that photochemically solidifies to form a single layer upon contact with the UV laser. Additional resin may be added and solidified in a layer-by-layer manufacturing process. Stereolithography may be used to construct modules in an additive top-down or bottom-up manufacturing approach.

Alternative approaches for constructing reactor modules may include self-assembly of polymers, e.g., block copolymers, to form 3-D gyroid structures or subtractive manufacturing methods. Subtractive manufacturing methods may include chemical or mechanical removal of sacrificial materials. For example, sacrificial materials may be formed using adhesive manufacturing with a sintering laser. The sacrificial material may be immersed, dipped, or otherwise coated in biocompatible polymers. The sacrificial material may then be dissolved or mechanically removed to form 3-D gyroid structures from the biocompatible polymers.

Bespoke Bioreactors and Systems

The bioreactor modules and systems herein can be designed and tailored for specific cell types and specific bioproduct output. In particular, the production bioreactor can be designed for a specific and individualized use. The volumes of the minimodules, the channels within each minimodule, the number of minimodule levels and the macrostructure can be selected to provide the cell environment (e.g., growth conditions) to achieve a given cell density, cell division rate, liquid shear force, and to accommodate choices of liquid media, liquid for harvesting bioproducts (such as solvents to break open and/or fractionate cell components), liquid flow rate, gas composition and gas flow rate.

In some embodiments, the system includes a mechanism for optimizing the bioreactor module and the cell environment in conjunction with one or more cells. The optimization mechanism may include a data loop that receives information about cell environment (E) and cell behavior (B) from the one or more sensors and cameras within the system. In addition, for the cells inputted into the system, genetic information (G) for the cell types can be inputted into the optimization mechanism, to provide for a relationship such as $G*E=B$.

In some embodiments, the cell environment is varied on one or more parameters (such as pH, liquid media components, gas composition, flow rates) and information on cell environment is collected for each variation ($E_1$-$E_n$) and the resulting cell behavior under each environment variation ($B_1$-$B_n$). In some embodiments, the cells inputted are varied (such as different genetics, e.g., cells that vary in division rate, nutrient consumption, morphology, stress tolerance) and information on each is collected for each cell variation ($G_1$-$G_n$) and the resulting cell behavior under the environment in the bioreactor ($B_1$-$B_n$). In some embodiments, variations are used in cell environment and cell genetics, and behavior measured, such that more each cell variation ($G_1$-$G_n$), the optimization mechanism measures a behavior ($B_1$-$B_n$) under more than one cell environment ($E_1$-$E_n$). The optimization mechanism ranks, indicates or otherwise compares the $G*E=B$ relationships across cell genetics and cell environments to provide information on compatibility, optimization, and ranking of different cell genetics under a variety of tested cell environments. The optimization mechanism can thereby optimize for production based on cell genetics, cell environment or both. The optimization mechanism can thereby provide parameters to optimize a production bioreactor, including the design of a bespoke bioreactor and bespoke cell environment conditions for the cell type and outputs for production.

In some embodiments, the optimization mechanism is a computer-controlled device. In some embodiments, the optimization mechanism includes a machine learning algorithm that employs the data from one variation or one set of variations to create the next variation or set of variations to test. In some embodiments, the systems, devices, and methods described herein may be used at zero gravity or under microgravity conditions such that the cells are grown in a zero gravity or microgravity condition.

Example Bioreactor Module and Systems

The bioreactor modules provided herein can be used separately or in combination to construct a system for producing, optimizing and in some cases, storing cells. In some embodiments, the systems, devices, and methods described herein may be used at zero gravity or under microgravity conditions such that the cells are grown in a zero gravity or microgravity condition. An example embodiment of a 3-module system is shown in FIG. 1. In this example embodiment, three bioreactors are interconnected to the system: Cell chip 200, sandbox bioreactor 400 and production bioreactor 800. Liquid media is mixed in the culture medium formulator 101 and moved for cleaning to an electroporator 20. The electroporator may include a cooler 21, to bring the temperature of the liquid media to the operating temperature for the system. Pump 40 moves liquid media from the formulator 101 into electroporator 20. Pump 50, flows the media through a bubble trap 60, to remove bubbles created by the electroporation treatment and bubble sensor 70 monitors the media flowed through for the proper bubble-free state. The media then reaches reservoir 30. In some embodiments, reservoir 30 is made up of two or more reservoirs so that when full the first reservoir 31 provides liquid media to the bioreactor modules while the second reservoir 32 is filling. Each bioreactor modules, 200, 400 and 800, receives liquid media from the reservoir when using pumps 100, 110 and 120, respectively. Gas is supplied to the bioreactors using gas supply 500, which may comprise one or more gas storage devices for each gas component. Gas supply can include a control device 900 for mixing and regulating gas composition and gas flow to the bioreactors, including different mixtures and different flow rates separately to each bioreactor module.

The system and bioreactors may also include certain output receptacles and devices. Each bioreactor that includes liquid media input and flow-through may also include a fluid disposal device. A common fluid disposal 600 can be utilized to collect spent liquid media from all bioreactor modules. Similarly, for each bioreactor that includes gas input and flow-though, a gas disposal may collect spent and cell-excreted gas composition. A common gas disposal 550 can be utilized to collect outputted gas from all bioreactor modules.

One or more sensors can be included with the use of a bioreactor or in a system of multiple bioreactors to monitor one or more parameters including physical, biological and chemical parameters as well as combinations thereof. Example sensors shown in FIG. 1 include sensor 80, for monitoring the culture medium formulator, sensor 81 for monitoring the electroporator and sensor 82 for monitoring the one or more reservoirs. Additional sensor 83 monitors the output from the cell chip module. Sensors 84 and 85 monitor liquid and gas output, respectively from the sandbox module. Similarly, sensors 86 and 87 monitor liquid and gas output, respectively from the production bioreactor module.

The system of one or more bioreactors can further include interconnection between the bioreactor modules. As shown in the example system of FIG. 1, the cell chip is interconnected by connection 280 to the sandbox module and can be regulated to allow passage of cells from the output of the cell chip to the input into the sandbox module. Connector 380 permits cells from the output of the sandbox module to flow to the input of the production bioreactor module. Connector 480 is an interconnection between the output of the production bioreactor to a collection receptacle or device collector 700. The collector 700 can collect cells, bioproduct or a combination thereof from production bioreactor 800. In some embodiments, collector 700 can include filters, membranes or other units and/or modules for separation, such as separation of cells from liquid media, separation of bioproduct from cells, and separation of or between cellular components.

Figure 2A:
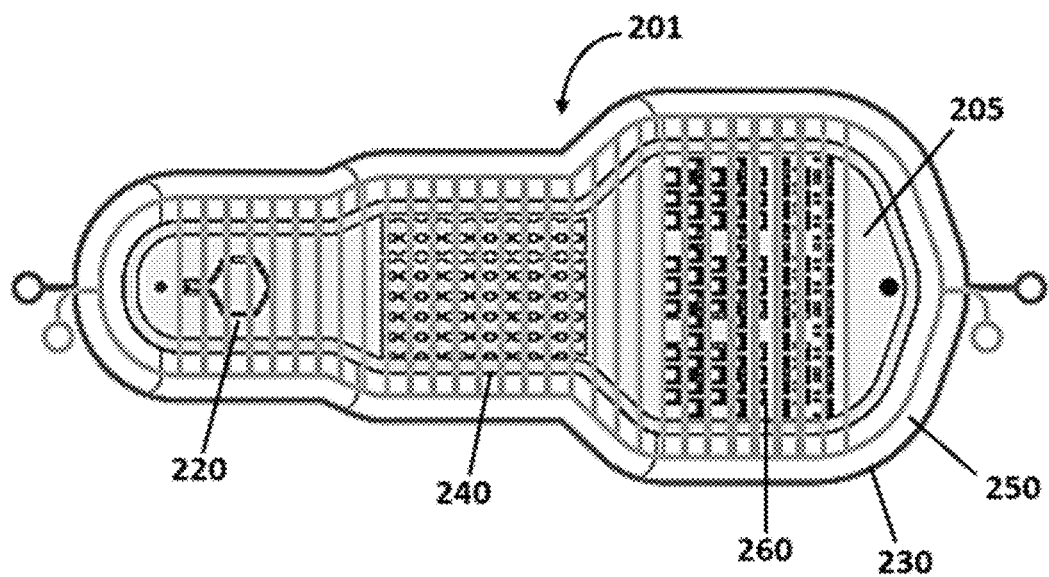
FIG. 2A shows an example embodiment of a cell chip module 201.
Figure 2B:
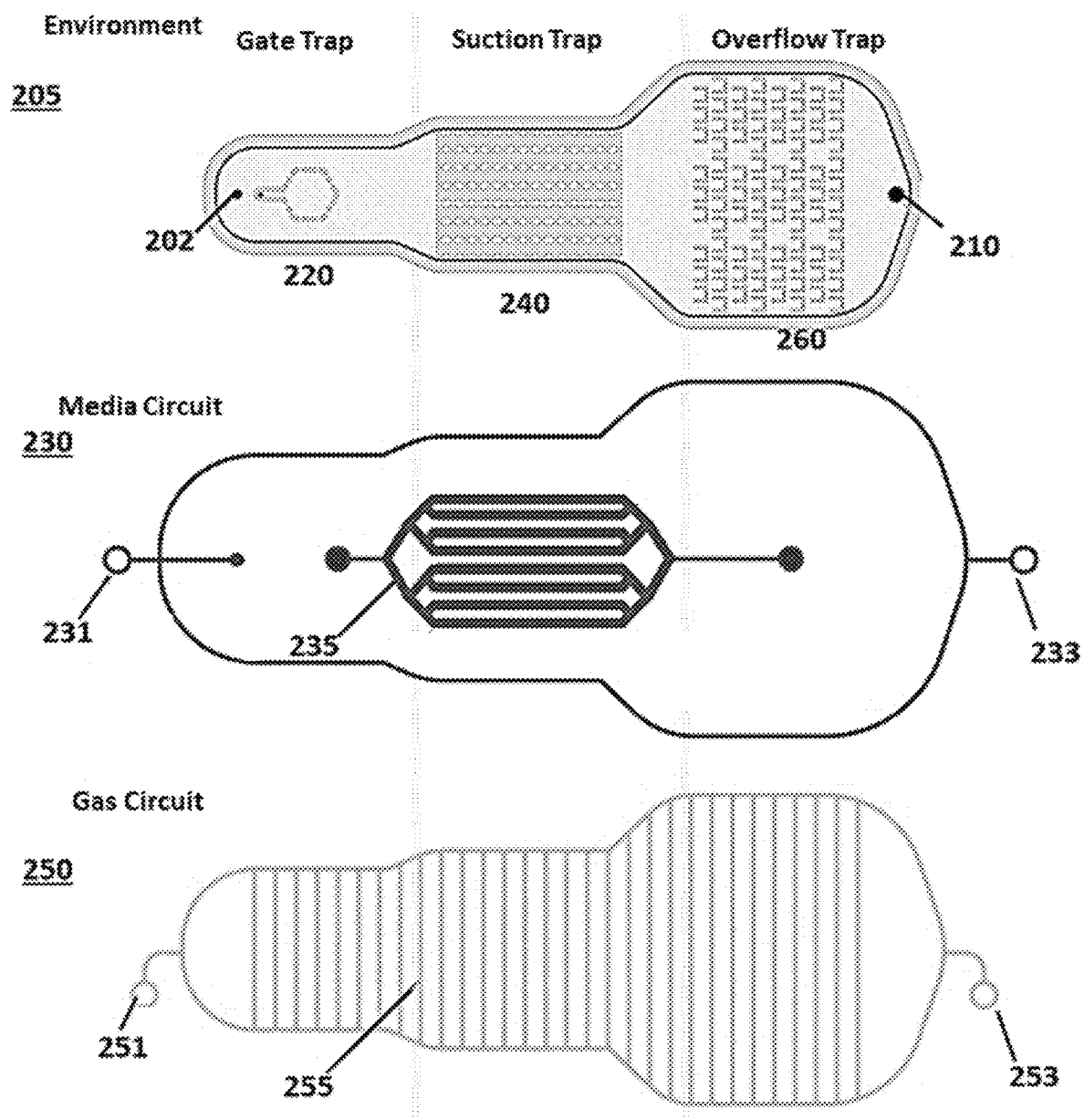
FIG. 2B shows an example embodiment of a cell environment 205, cell chip media circuit 230 and cell chip gas circuit 250 as individual "layers" of a cell chip.
Figure 2C:
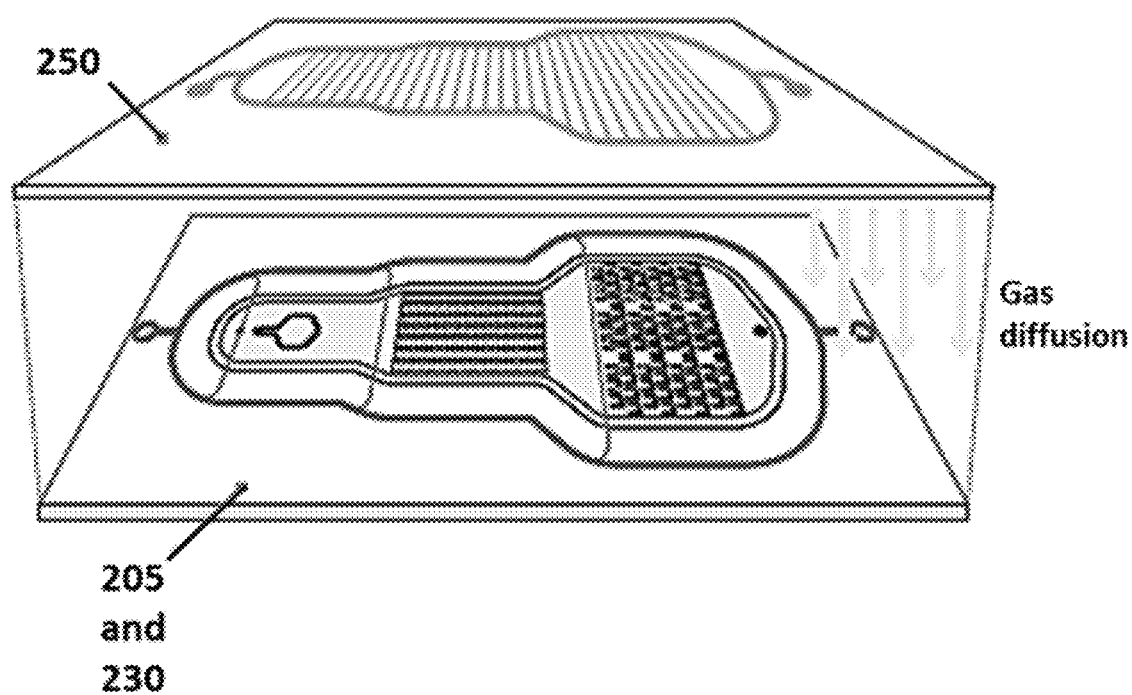
FIG. 2C shows the side profile of the layers of the cell chip.

Shown in FIG. 2A is an example cell environment 205 in a chip module 201. In this example, the cell chip includes gate trap 220, multiple suction traps 240 and multiple overflow traps 260. At the input end is a media input port 202 for providing media to the cell environment. At the opposite end (in the direction of liquid media flow) is harvesting port 210, for harvesting cells grown in the cell chip module. Details of an example media circuit 230 for cell chip 201 is shown in FIG. 2B. The media circuit may include input media port 231, output media port 233 and media feeding channels 235. Details of an example gas circuit 250 for cell chip 201 is shown in FIG. 2B. The gas circuit may include input gas circuit 251, output gas circuit 253 and gas distribution channels 255. FIGS. 2C shows a side view of cell chip 201 with an example of the arrangement of the media circuit 230, gas circuit 250, and cell environment 205.

FIGS. 3A-3F show example traps for use with a cell chip module. An example gate trap 221 is diagrammed in FIG. 3A (upper view) and 3B (side view), shown in proximity to media input port 202. The gate trap is constructed from flow protectors 225 surrounding an internal space, the protectors 225 have openings 227 between them that limit cell 203 flow out from the internal space of the trap. In some embodiments, the openings 227 between protectors 225 are sized to be twice the diameter of the cells to be grown on the cell chip. In some embodiments the openings 227 are sized to be greater than the diameter of the cells to be grown on the cell chip. Cells may be inoculated onto the chip and into gate trap 221 using inoculation port 223.

Figure 3A:
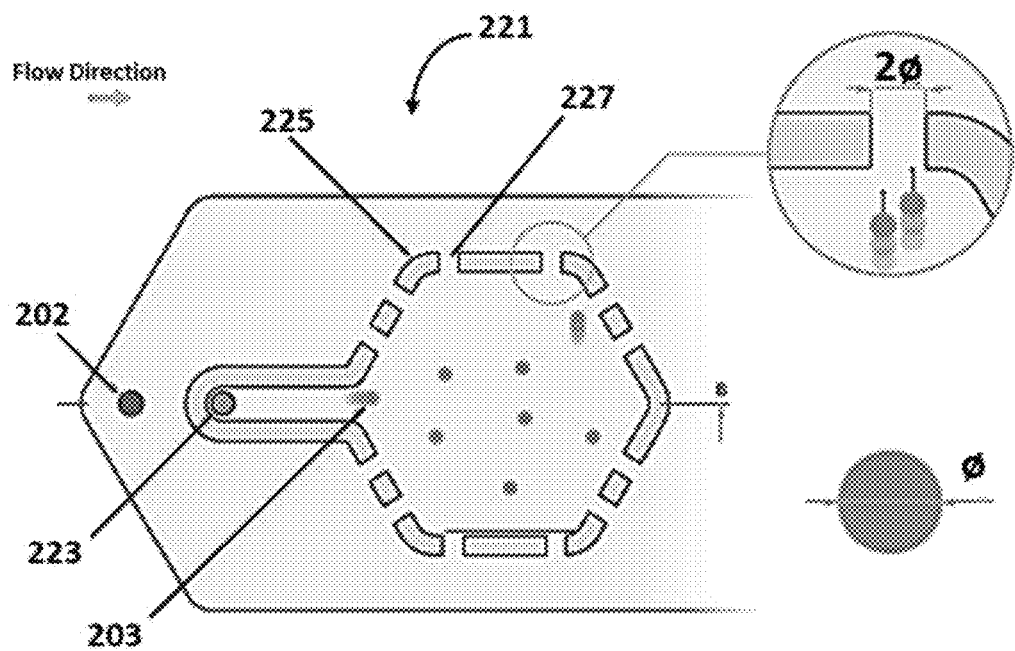
FIGS. 3A-3F provide example embodiments of cell traps for use with a cell chip module.
Figure 3B:
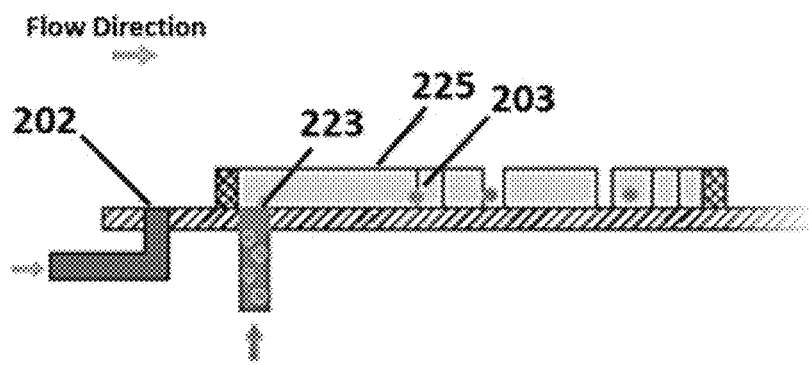
Figure 3C:
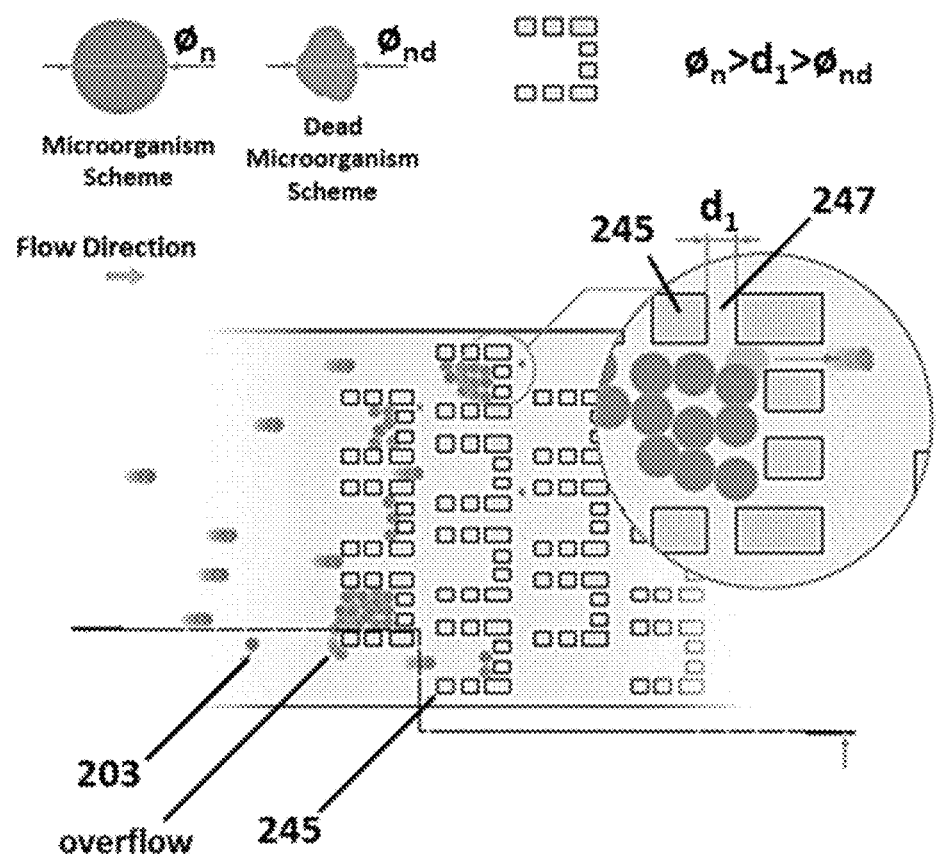
Figure 3D:

FIGS. 3C and 3D show an example overflow trap 240 arrangement from upper view (FIG. 3C) and side view (FIG. 3D). The traps are constructed from arrangements of canalized box walls 245 arranged to surround an inner space on three sides and in a formation to create openings 247 between the wall sections 246. The size of openings 247 can be tailored to the cells to be grown on the chip. In some embodiments, openings 247 are smaller in diameter than a live cell, but larger than the diameter of a dead cell, such that live cells 203 remain trapped in the inner space of canalized box walls 245 until they reach sufficient number to overflow the box arrangement, whereas dead cells pass through openings 247 and are not retained within the inner space of canalized box walls 245.

Figure 3E:
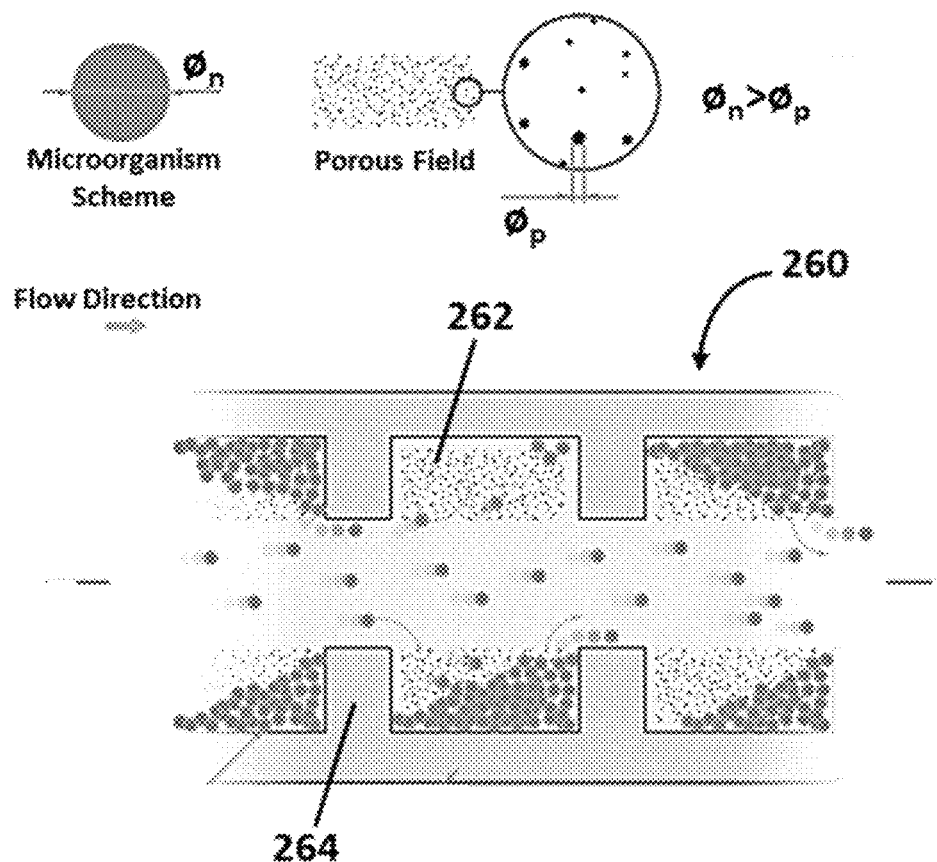
Figure 3F:
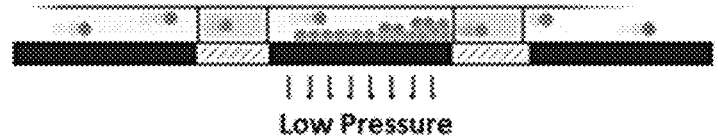

An example suction trap 260 is show in upper view and side view in FIGS. 3E and 3F. The trap has porous fields 262 and environment walls 264. The porous field is designed such that the size of the cells exceeds the size of the pores.

Figure 4A:
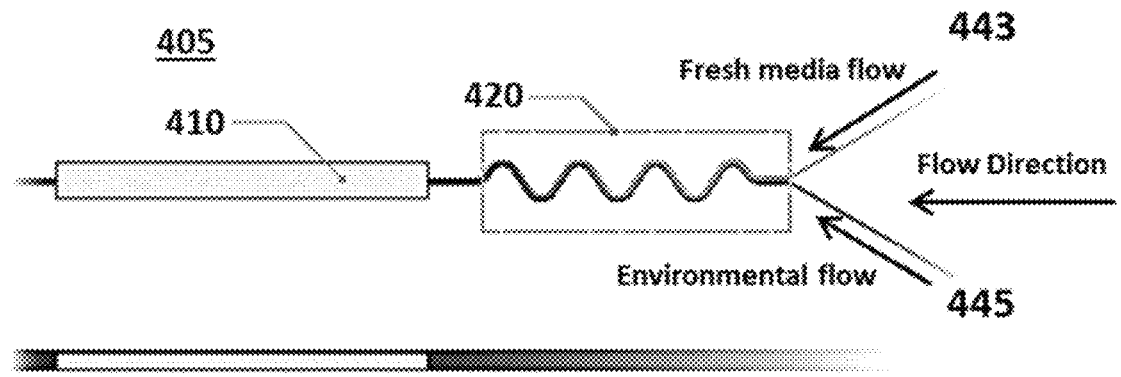
FIGS. 4A-4E provide example embodiments of a sandbox bioreactor.
Figure 4B:
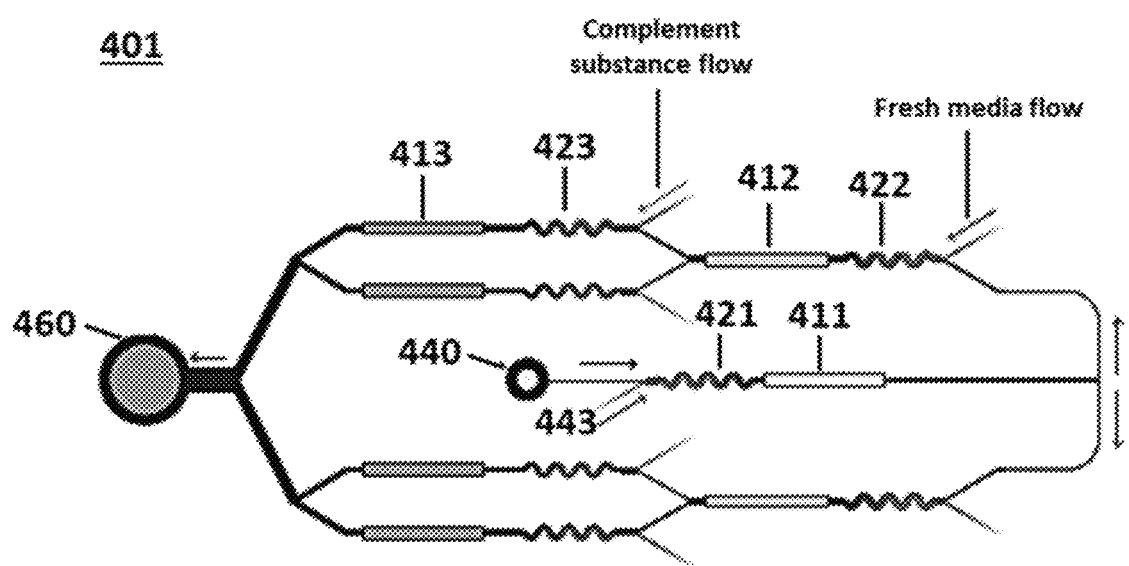
Figure 4C:
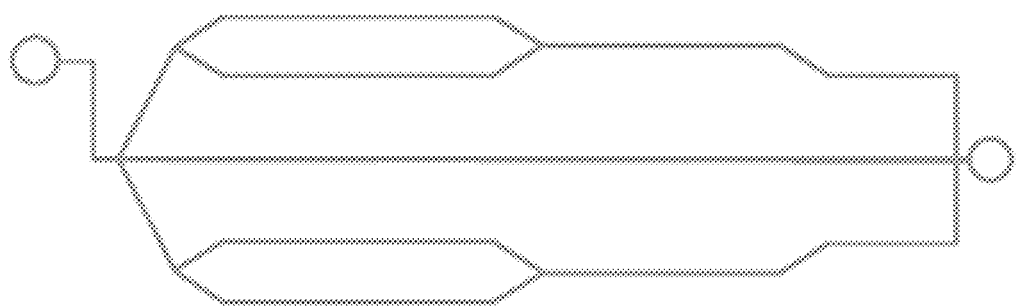
Figure 4C:
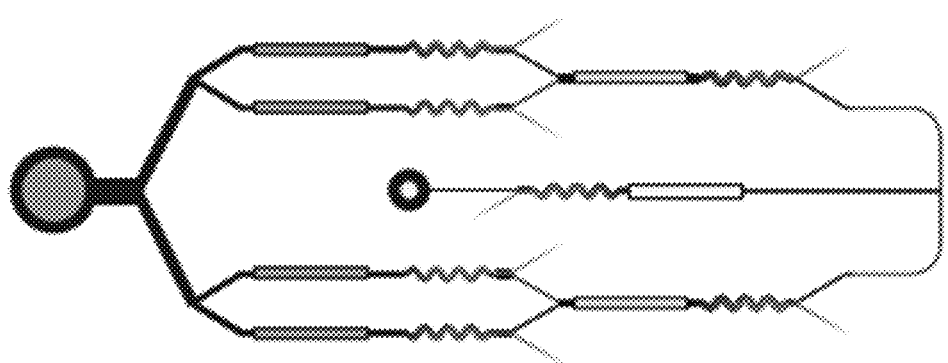
Figure 4D:
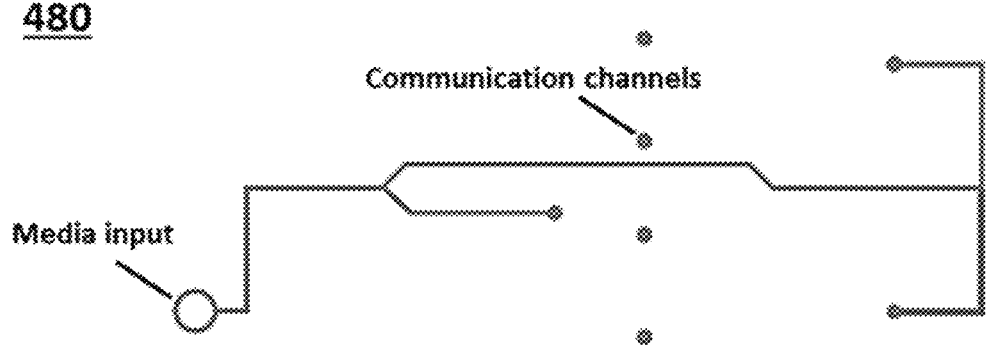
Figure 4D:
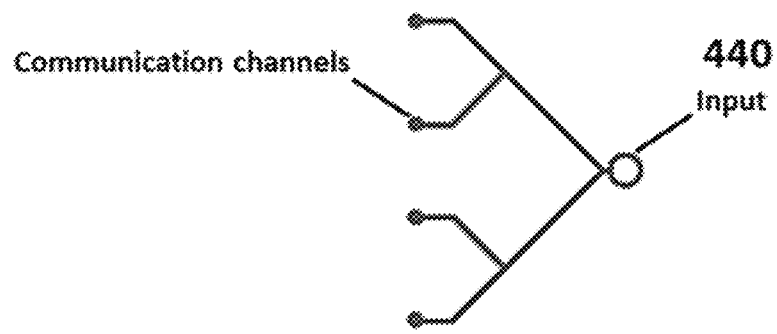
Figure 4E:
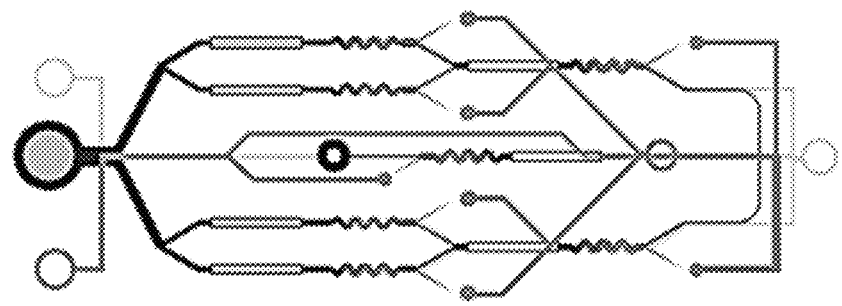
Figure 4E:
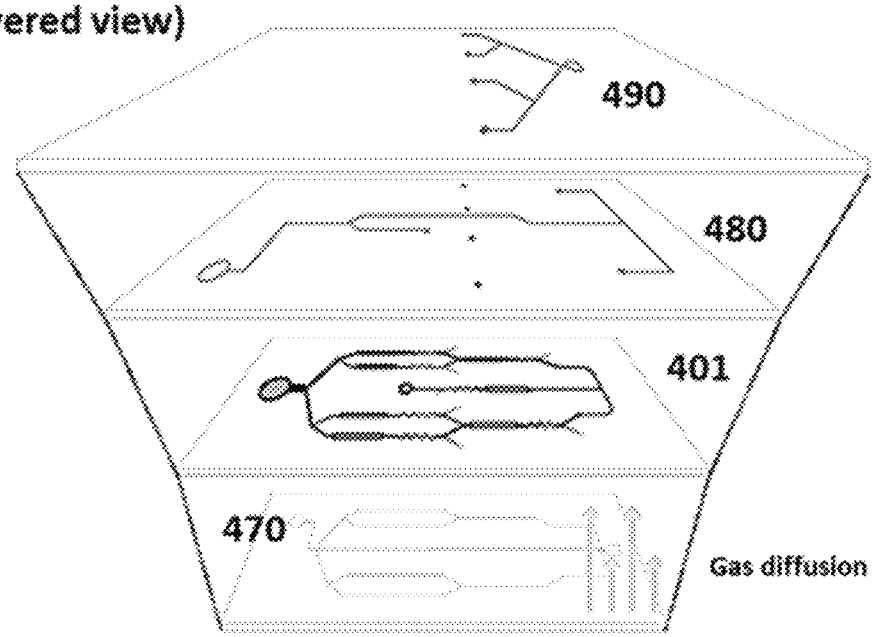

FIGS. 4A-4E display example sandbox modules and components thereof. FIG. 4A displays an example sandbox segment 405. The example segment includes channel 445 where cells and associated cell environment flow into mixing module 420 where liquid media from channel 443 mixes with the cells and subsequently the mix flows into cell chamber 410 for cell growth and optionally, measurement by one or more sensors or cameras. FIG. 4B displays an example sandbox module cell environment 401 which includes multiple segments joined in series and in parallel, a cell input 440 and cell output 460 from the sandbox module. Each example segment includes a mixing module (e.g., 421, 422, 423) and cell chambers (e.g., 411, 412, 413). FIG. 4C shows an example of a gas circuit 470 (top) for example sandbox cell environment 401 (bottom). FIG. 4D shows an example of a liquid media circuit 480 (top) with media input and an example of a cell input channels 490 (bottom). FIG. 4E shows an example of the overlay of liquid media circuit 480, gas circuit 470, and cell input channels 490 onto an example sandbox cell environment 401 to construct example sandbox module 400, shown from a top view and side view.

Figure 5:
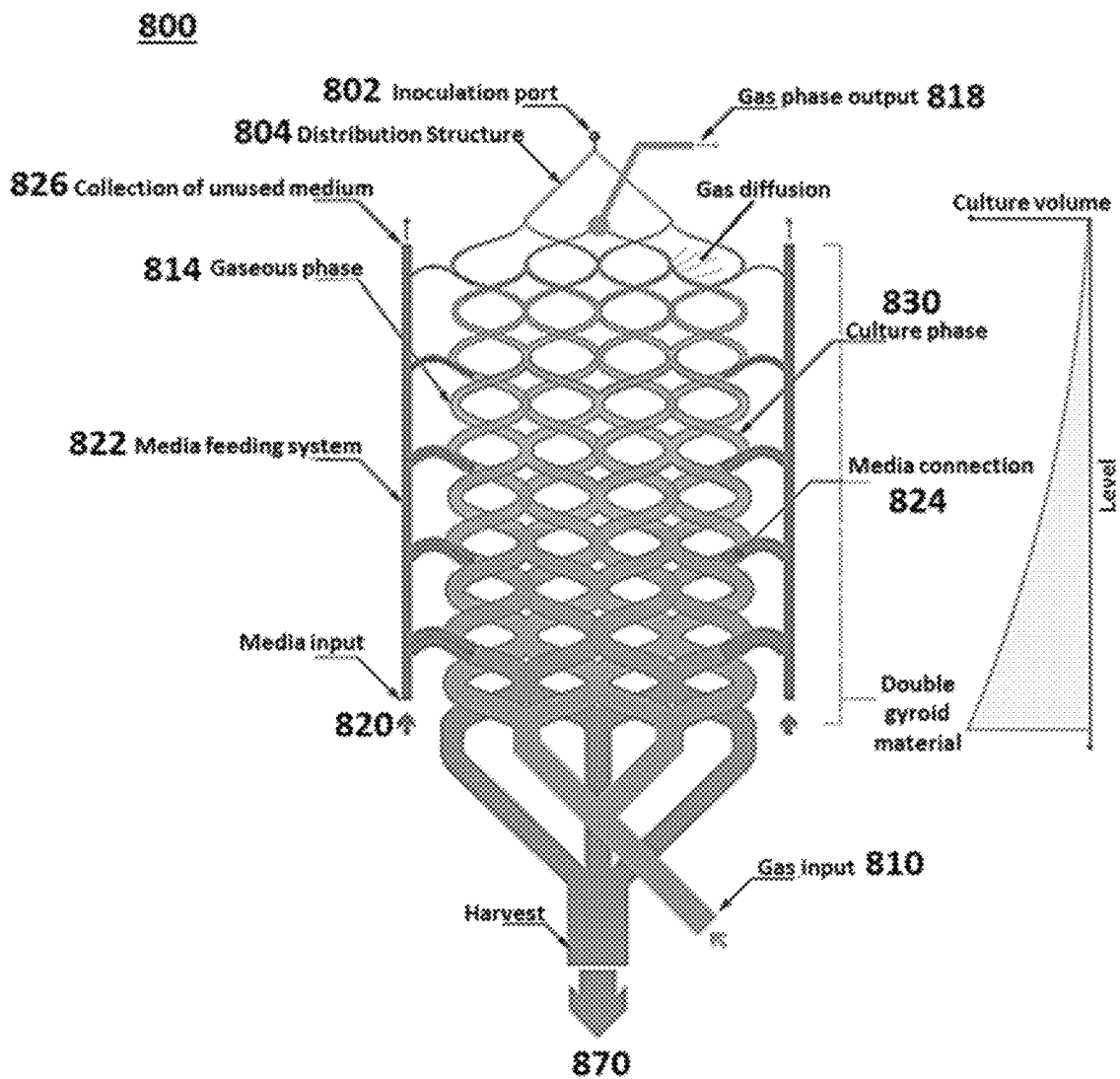
FIG. 5 provides an example embodiment of a production bioreactor.

FIG. 5 displays an example production bioreactor 800 which includes inoculation port 802 for cells to enter the bioreactor, and cell distribution structure 804, where cells flow into the bioreactor and are mixed with liquid media and other cell environment components to generate a culture phase 830. Liquid media input 820 permits introduction of liquid media into the production bioreactor which is then distributed through media feeding system 822 using media connections (e.g., 824), and unused media is collected 826. Gas enters at gas input 810 and distributes throughout the bioreactor by way of gas phase channels 814, and is outputted through gas output 818. Cells and/or products produced by cells can be harvested through port 870.

Figure 6A:
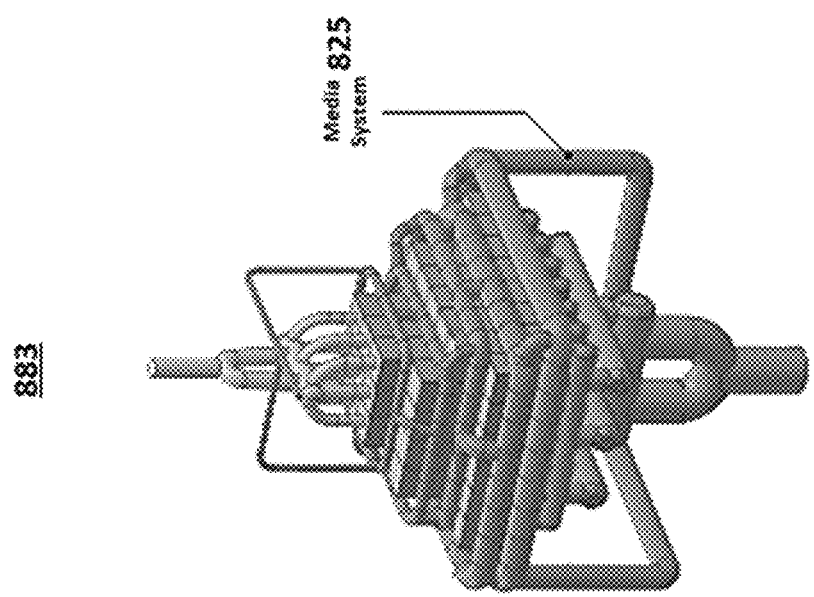
FIG. 6A-6C provide example embodiments for macrostructures for a production bioreactor.
Figure 6A:
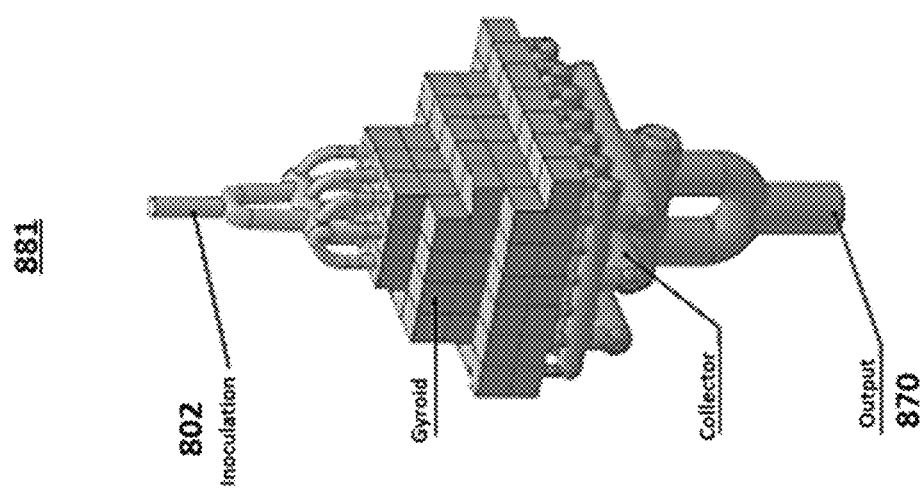
Figure 6B:
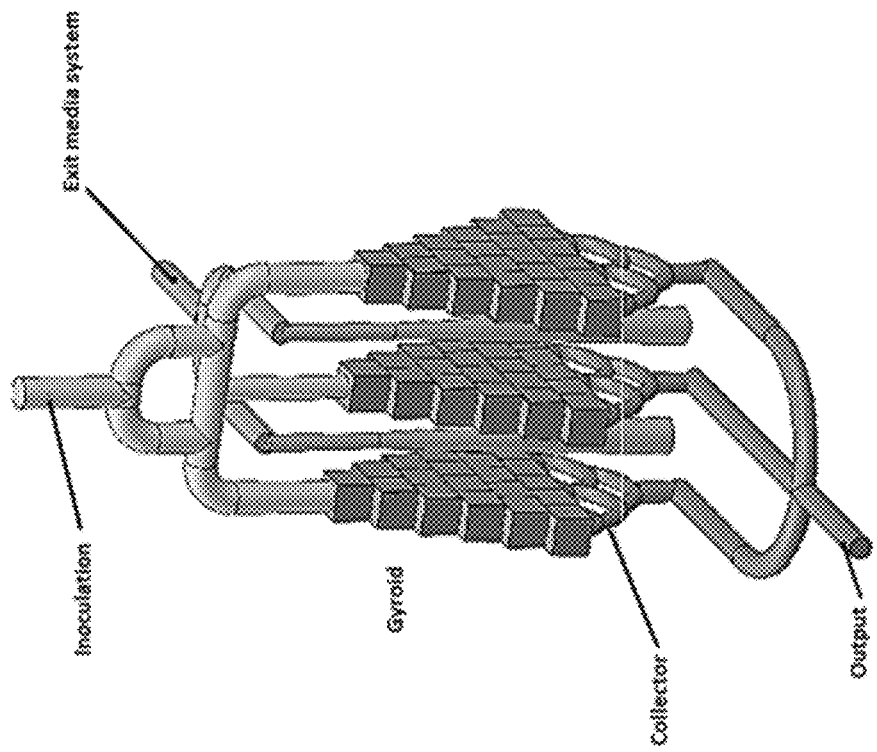
Figure 6B:
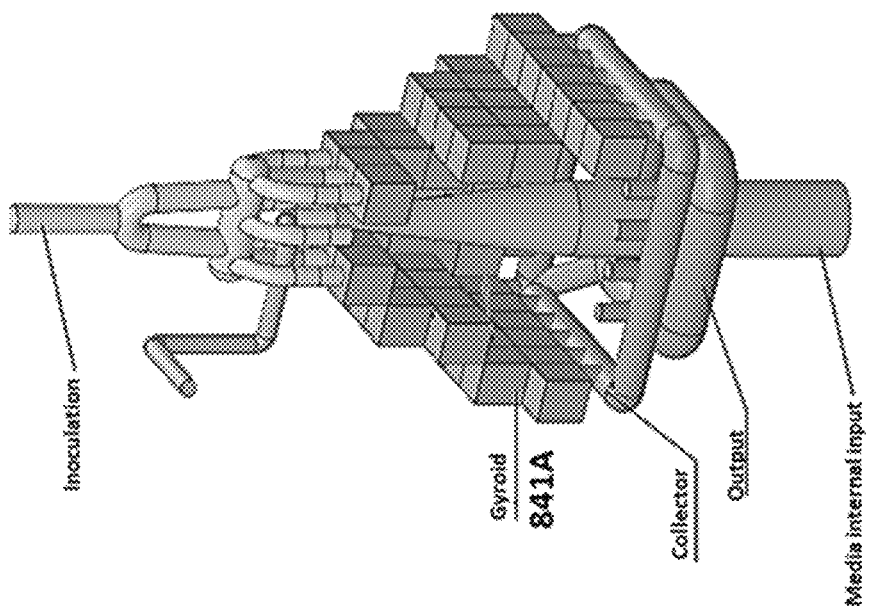
Figure 6C:
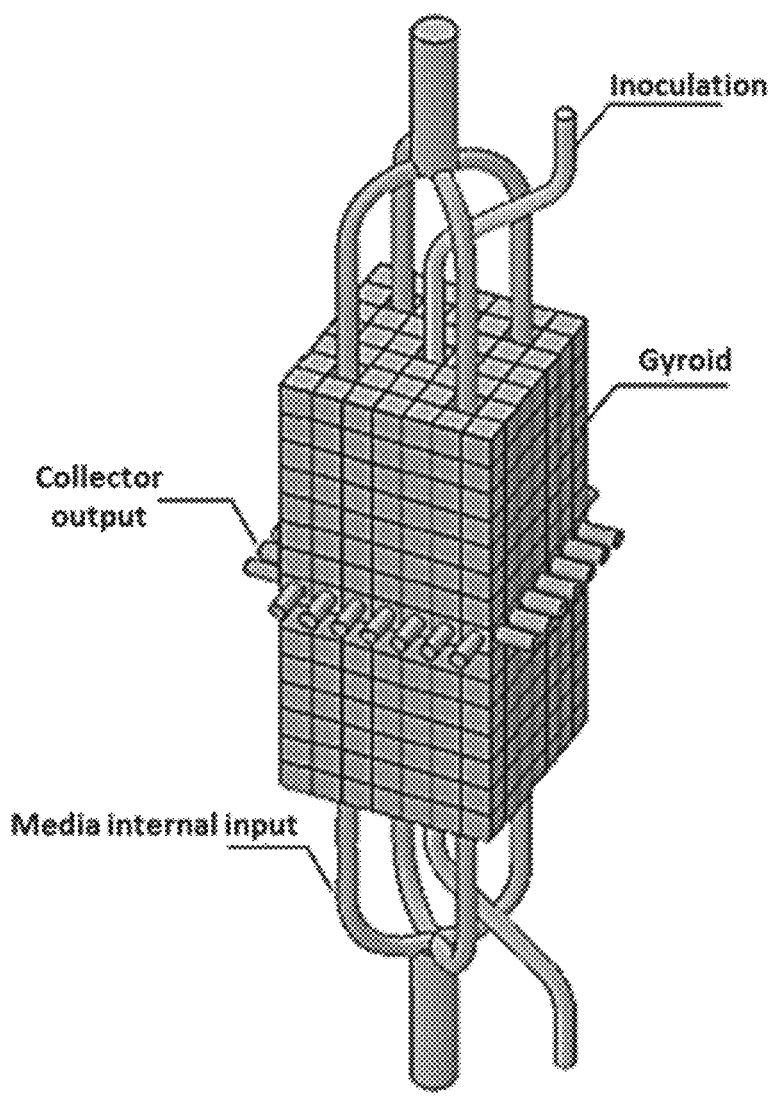

FIGS. 6A-6C display examples of macrostructures for use with the production bioreactors described herein. FIG. 6A shows an example pyramid macrostructure 881 and a pyramid macrostructure 883 overlaid with media distribution system 825. FIG. 6B shows example hollow pyramid macrostructures 885 and 887. FIG. 6A shows an example log macrostructure 889.

Figure 7A:
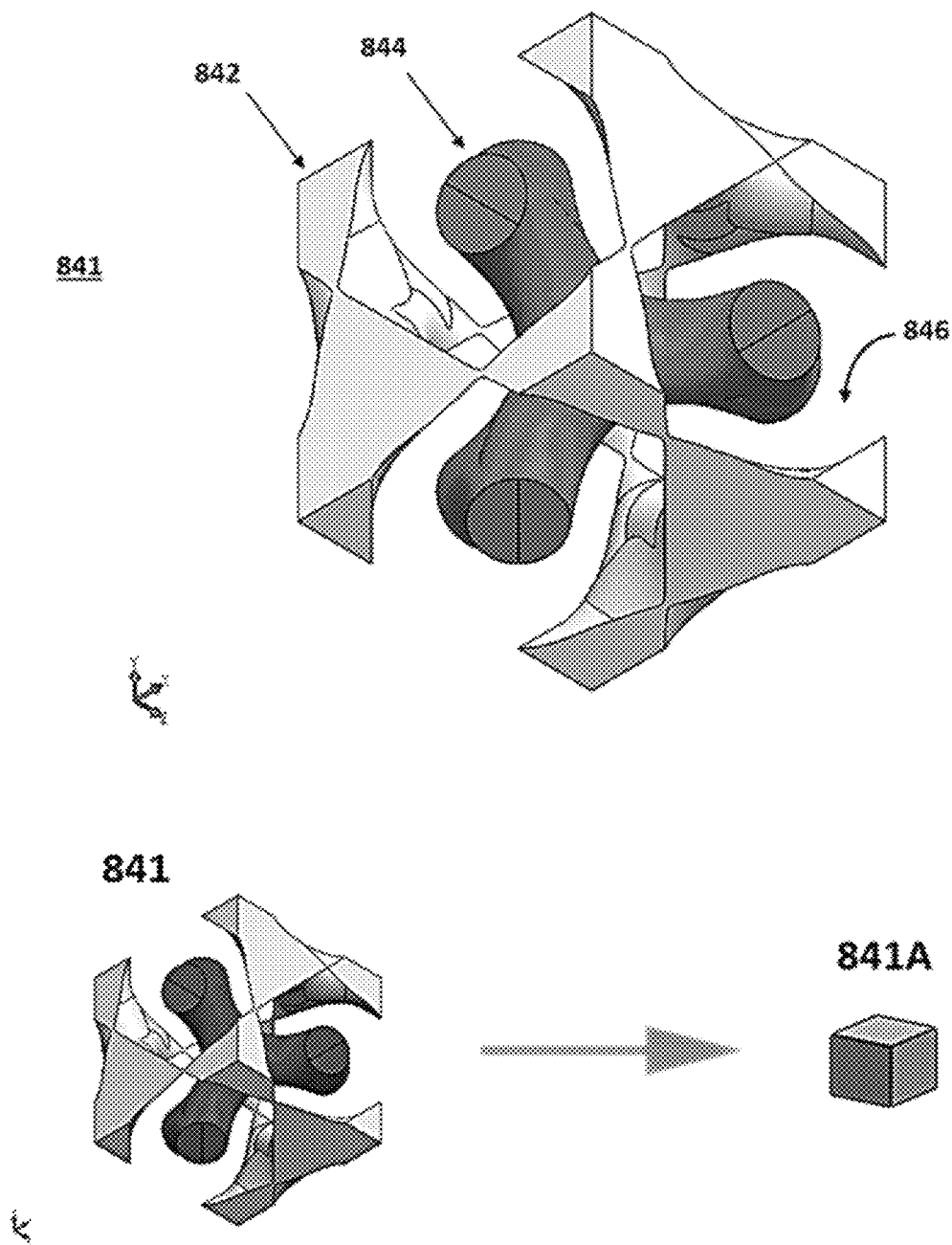
FIG. 7A shows an example embodiment of a modified double gyroid shape or structure and assembly into overlaying channels such as for use in a production bioreactor as described herein.
Figure 7B:
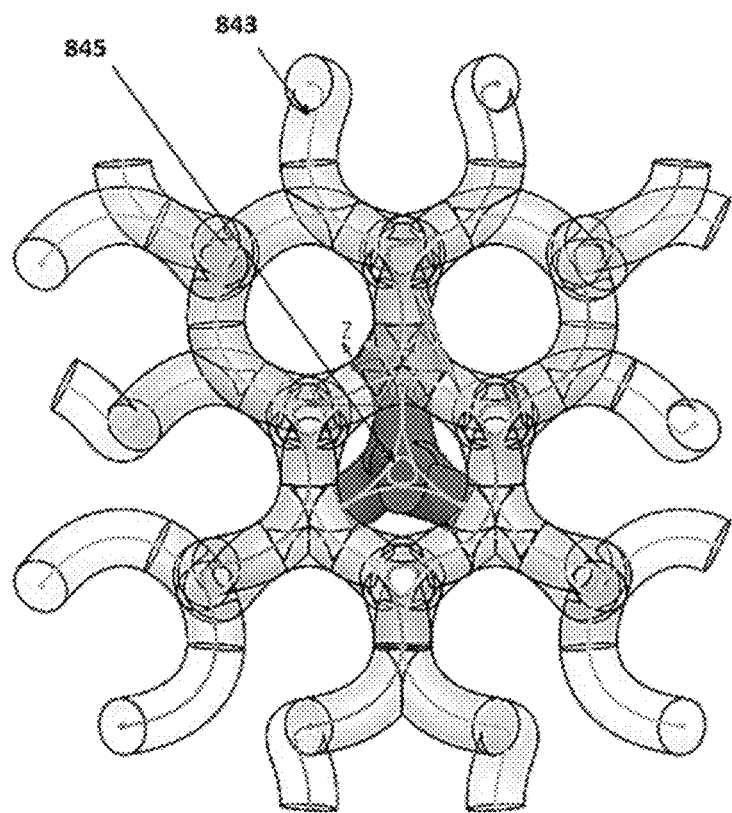
FIG. 7B provides an example of assembled modified double gyroid shapes or structures into two overlapping networks of channels.
Figure 7C:
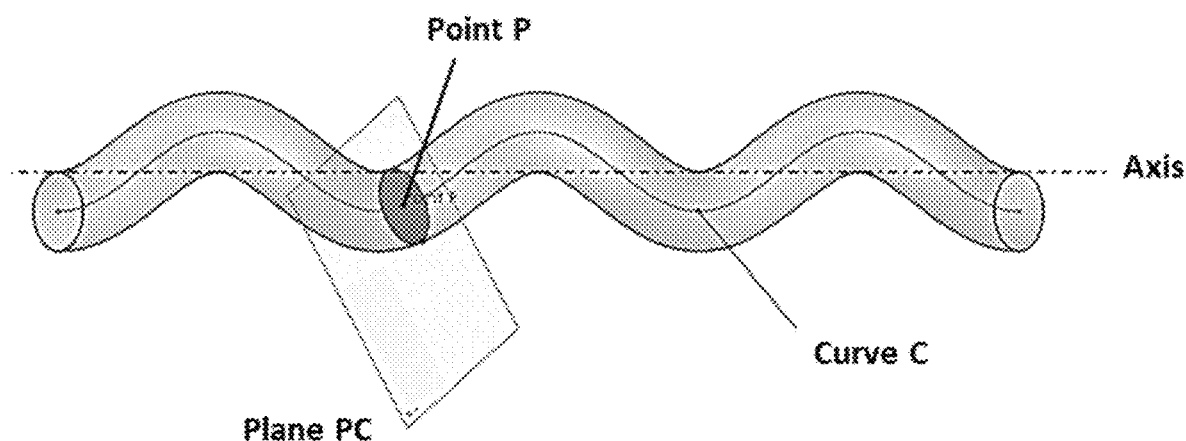
FIG. 7C provides an example of the curvature created by the assembly of modified double gyroids into a channel.

In some embodiments, the macrostructures for production bioreactors are made up of minimodules each of which may be have a given shape, such as a double gyroid or modified double gyroid. FIG. 7A shows an example embodiment of a modified double gyroid shape 841 for use in constructing one or more minimodules for a production bioreactor. As shown in the bottom of the figure the double gyroid minimodule is schematically represented as box 841A, such as shown in macrostructures of FIGS. 6A-6C. Modified double gyroid shape 841 may include phases 842 and 844, which when assembled, such as displayed in FIG. 7B, can be assembled into overlaying channels 843 and 845. Additionally, between phases 842 and 844 is intermembrane space 846. FIG. 7C shows an example sweep of a portion of example channel 842 which displays a constant diameter throughout the channel.

Assembly of Minimodules into Macrostructures

Figure 9B:
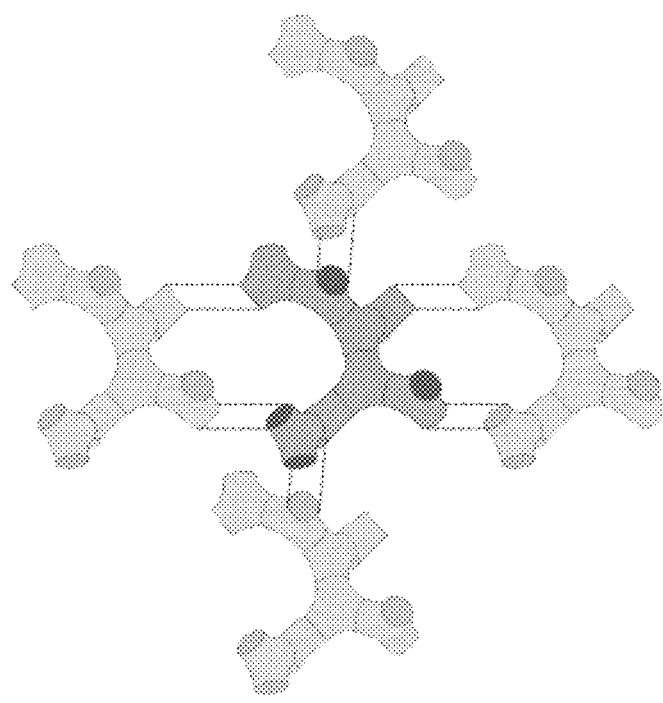
FIGS. 9A-9F shows an example schema for an assembly of minimodules into macrostructures.
Figure 9A:
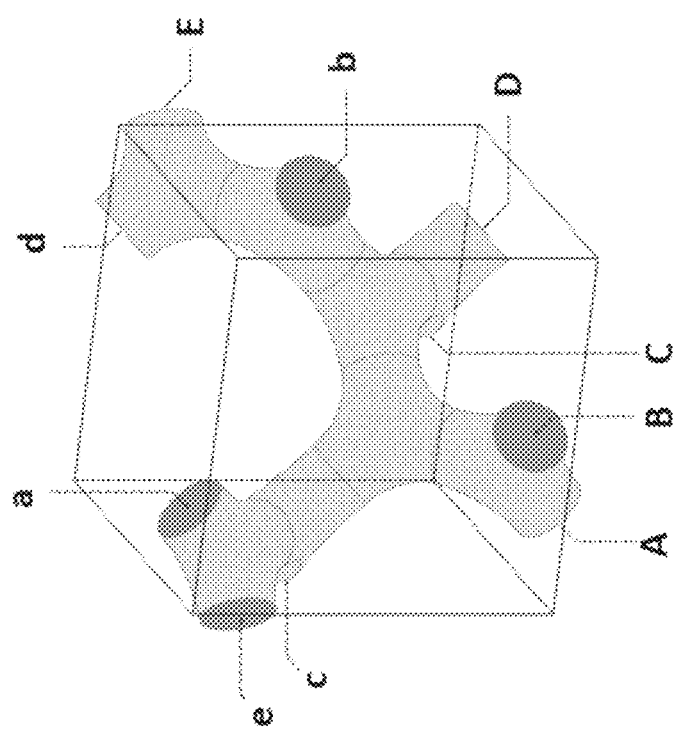
Figure 9C:
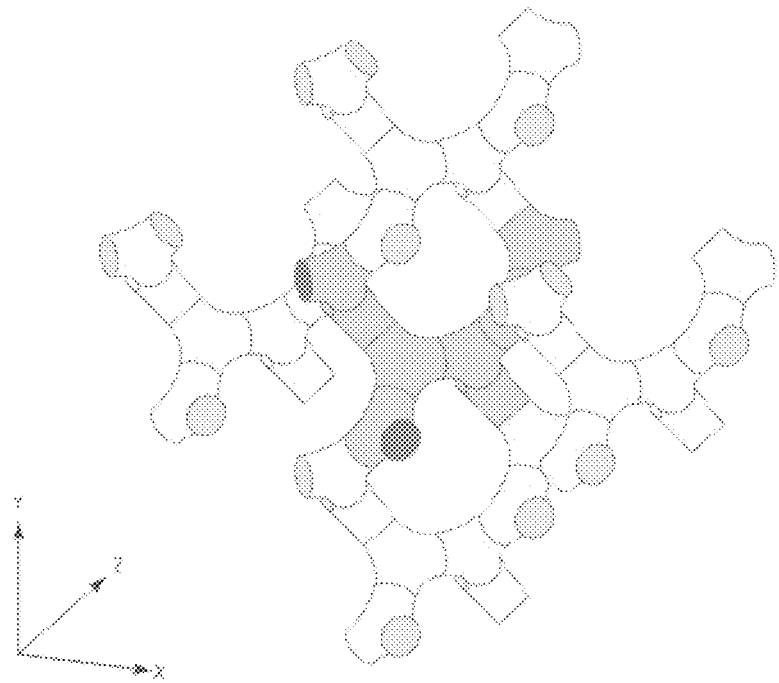
Figure 9D:
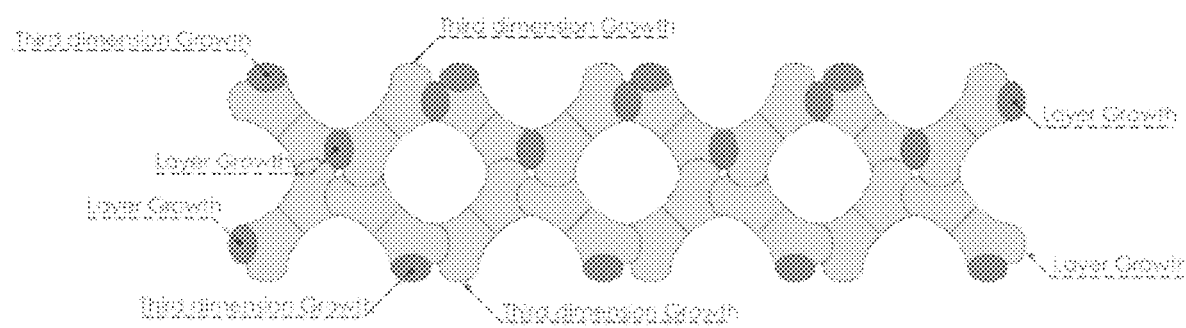
Figure 9E:
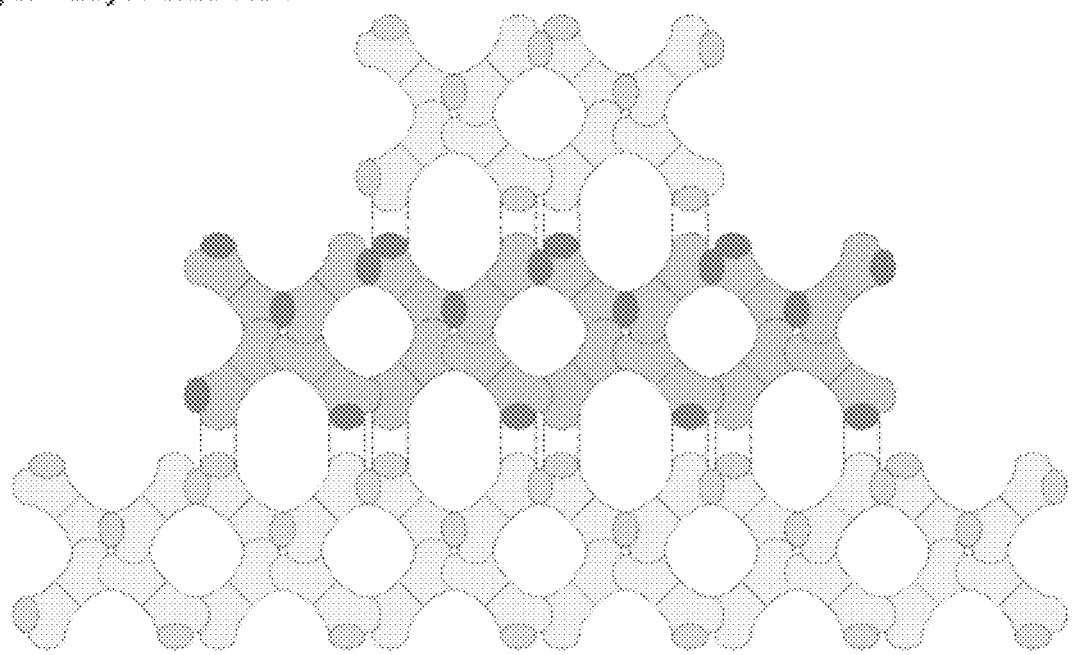
Figure 9F:
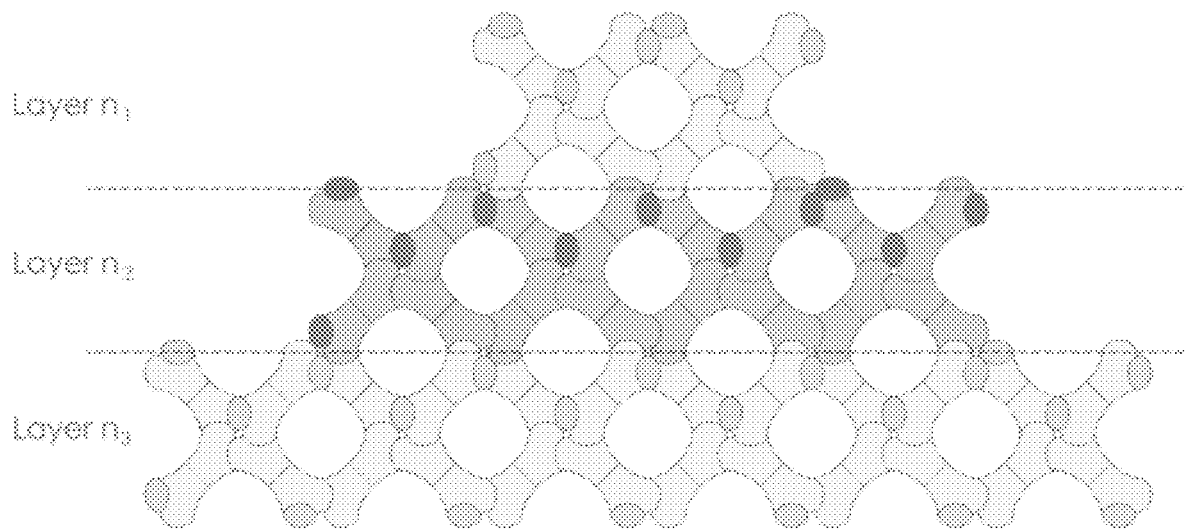

The minimodules described herein can be assembled into macrostructures providing for targeted control of media and gas flow and distribution. In some embodiments, the minimodule is a modified double gyroid (DG) that is assembled into a macrostructure to create the production bioreactor. FIGS. 9A-9F illustrates assembly starting with a first minimodule (e.g., DG) and assembling additional minimodules such that the geometry is repeated to form a three-dimensional (3-D) matrix whose growth is limited to two of the three possible dimensions. The connected points of one minimodule to another minimodule is referred to as a "mouth." This first assembly of interconnected minimodules which are oriented identically is referred to as a "layer." The layer can be arranged, for example, in a rhomboid shape such that in some embodiments, if the same number of modules are connected in the selected directions, the resultant growth is not proportional and as such the growth of the layers is irregular with respect to one another. In some embodiments, the layer is arranged in a square shape or such that the resultant growth is proportional. FIGS. 9D-9F illustrates one example embodiment of layer assembly and growth.

On the edges of each layer the unconnected mouths of the minimodules can be used to connect the layer with other functionalities, such as the input for media flow or for gas and the output of spent media, spent gas and output of cells or bioproduct produced by cells.

Figure 10B:
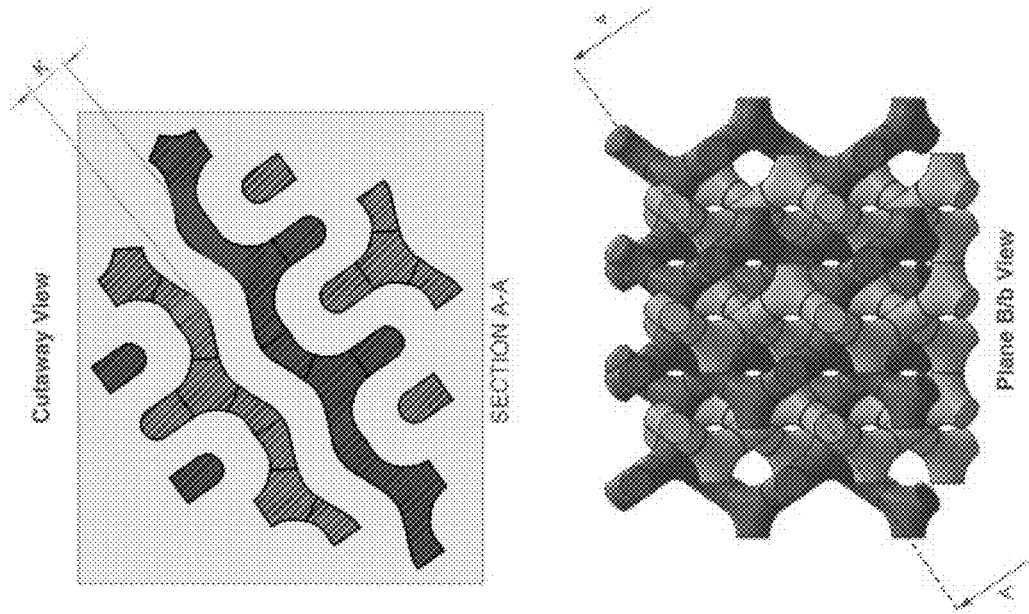
FIGS. 10A-10F show examples of layer assemblies of various shapes, for example square and square-like assembly shapes.
Figure 10A:
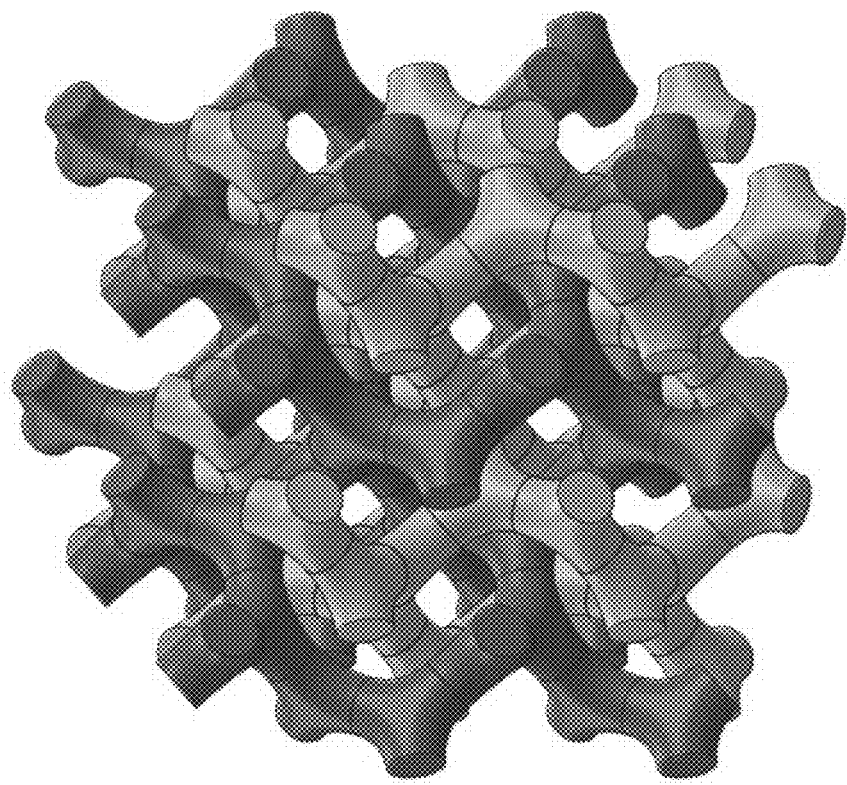
Figures 10C, 10D:
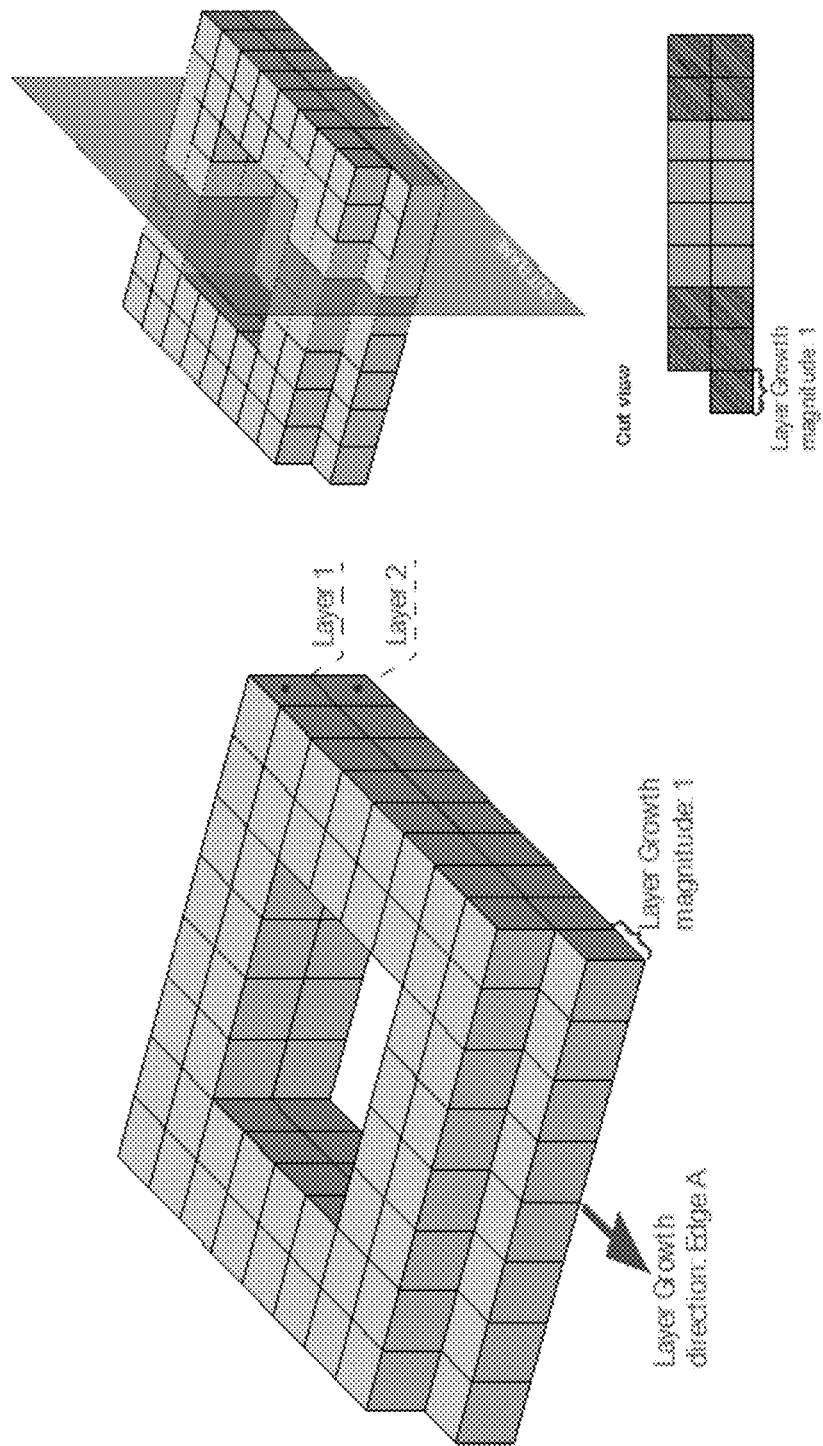
Figure 10F:
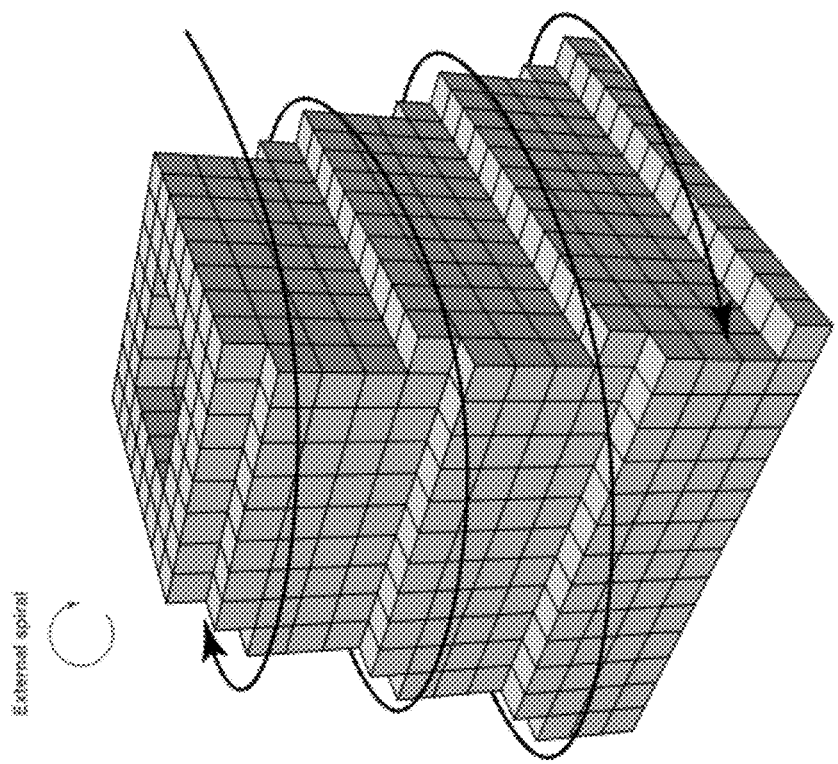
Figure 10E:
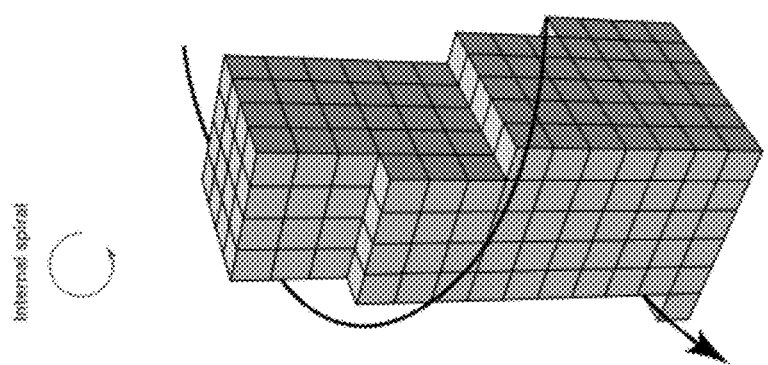
Figure 11A:
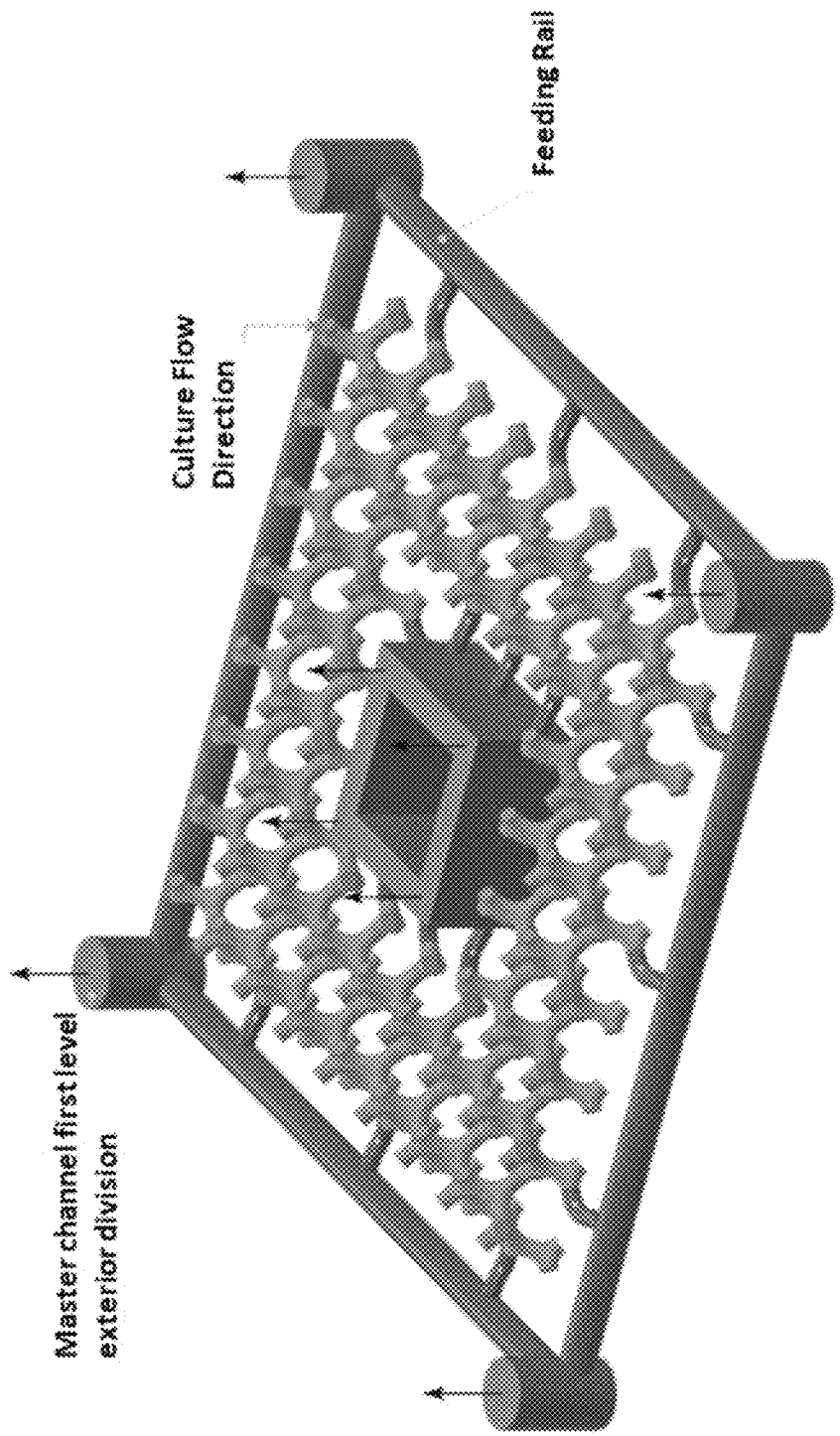
FIGS. 11A-11F show examples of module layers connected to example feeding circuits.
Figure 11B:
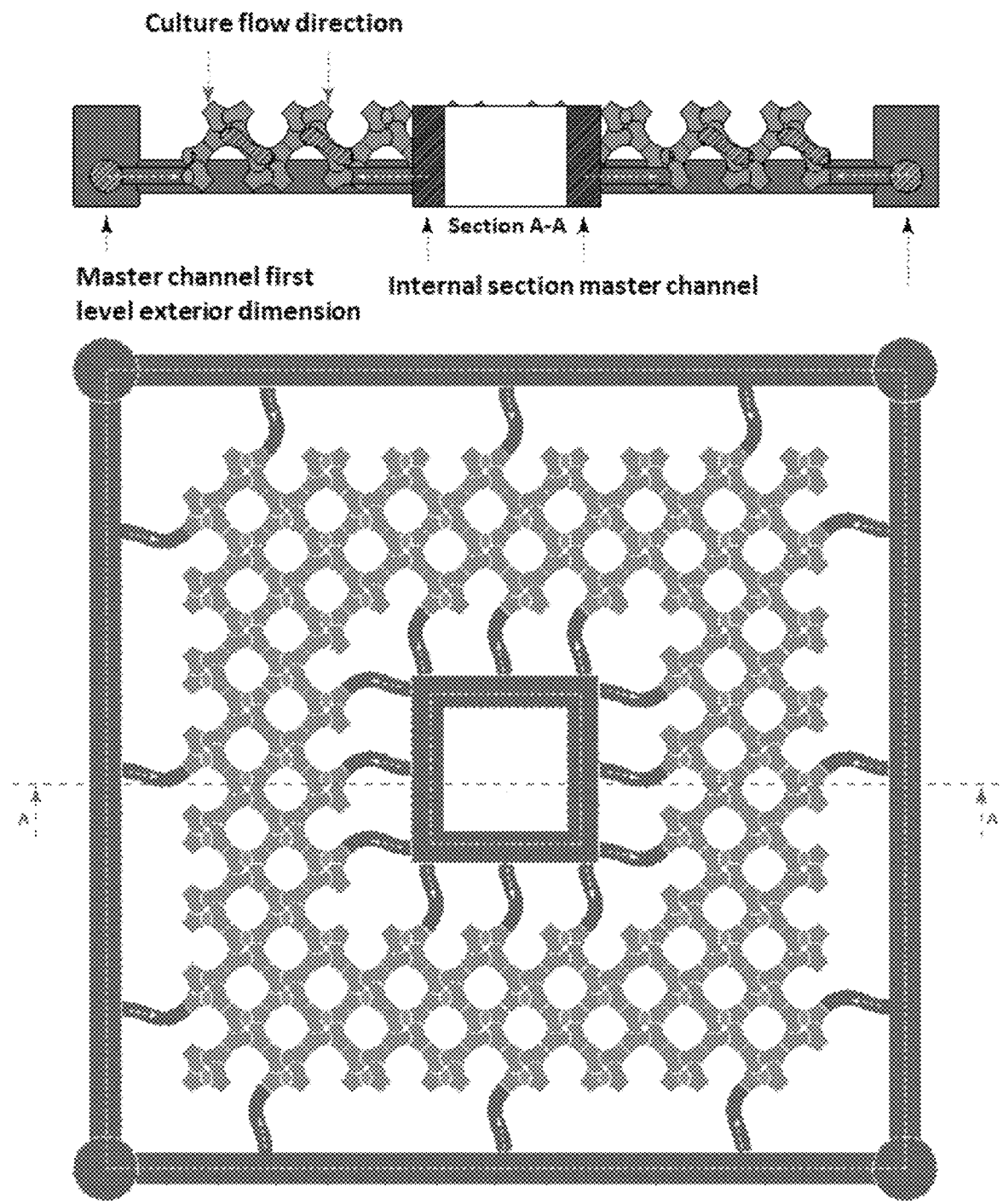
Figure 11C:
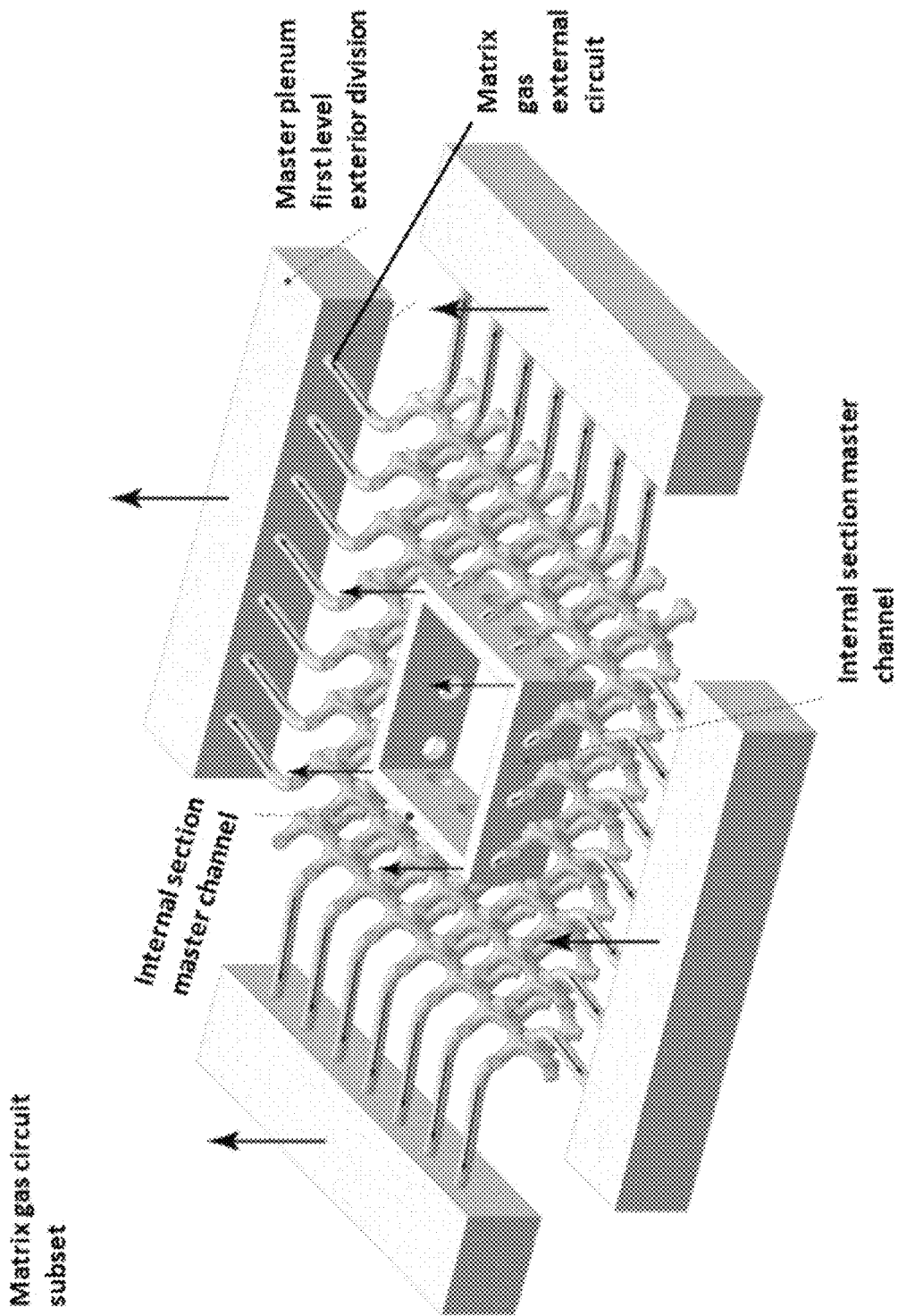
Figure 11D:
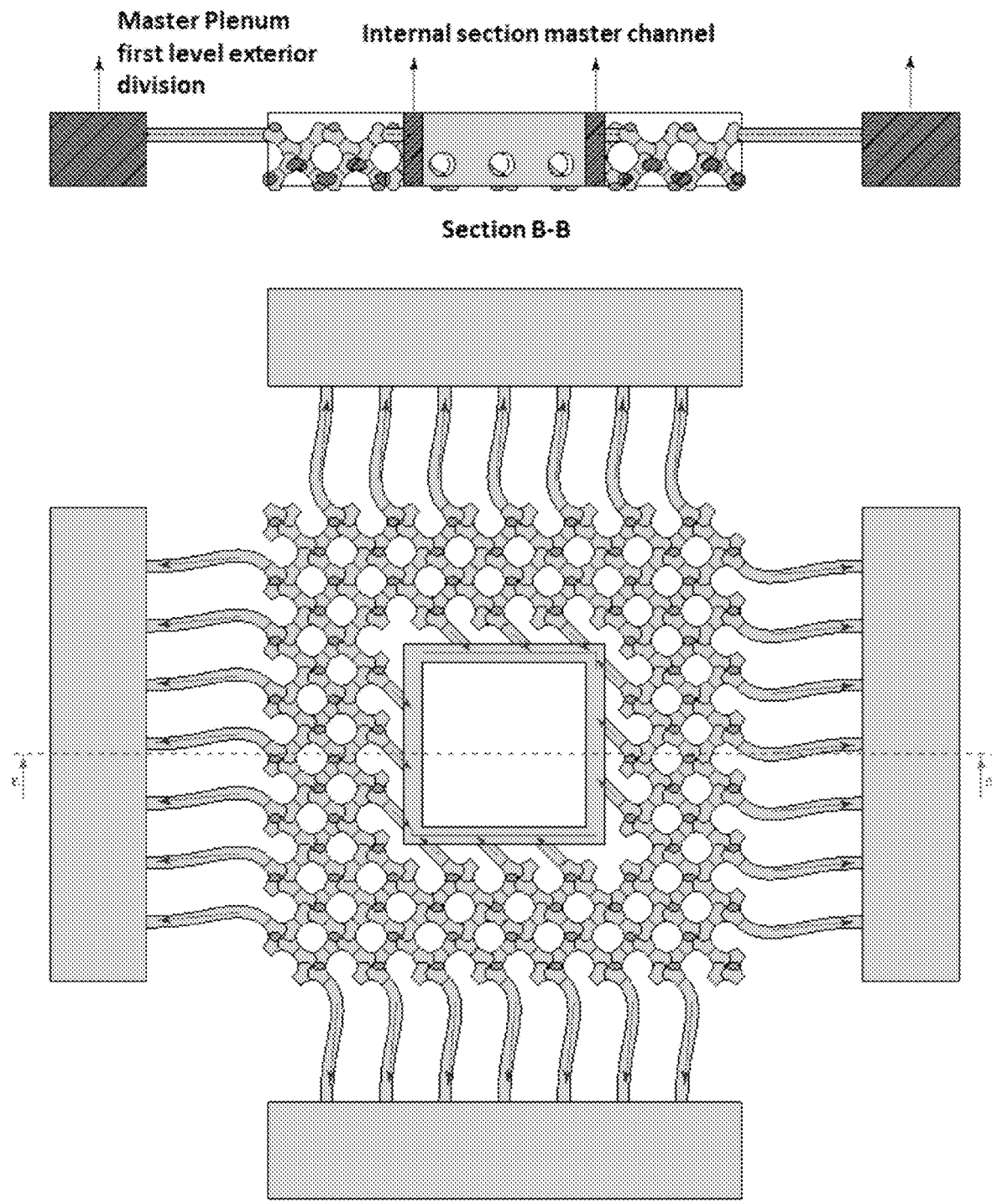
Figure 11E:
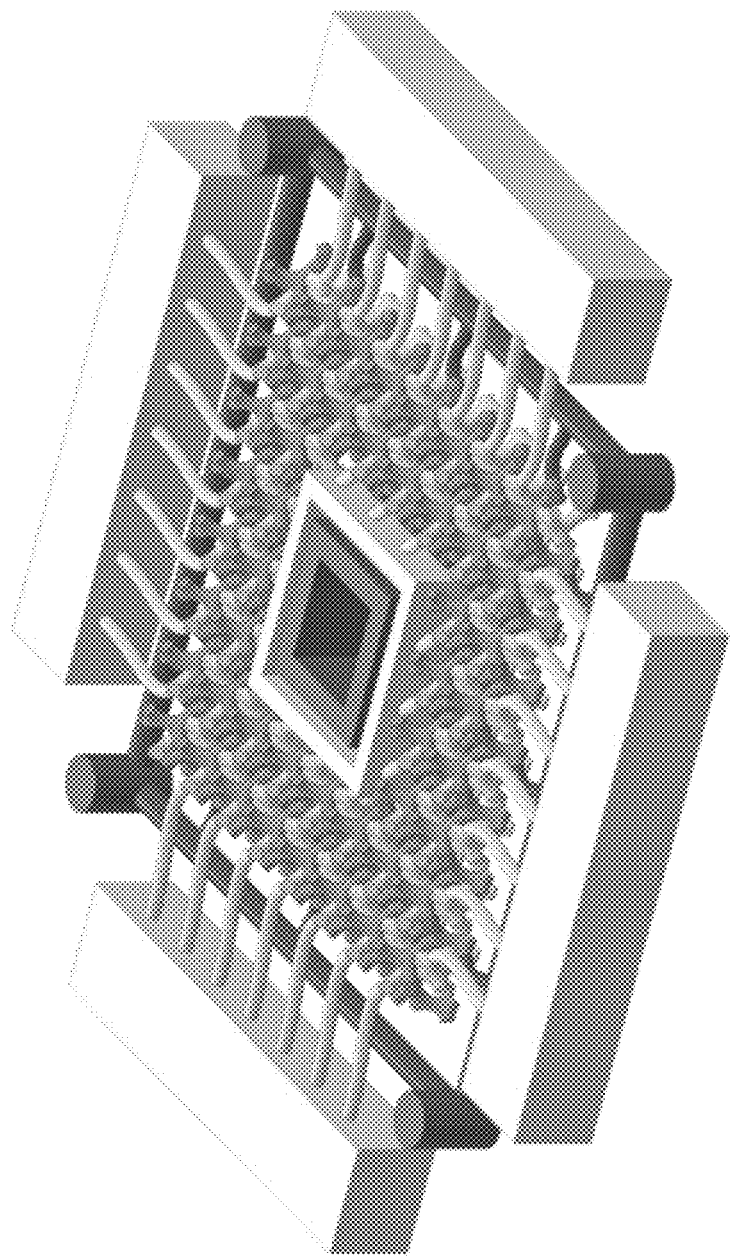
Figure 11F:
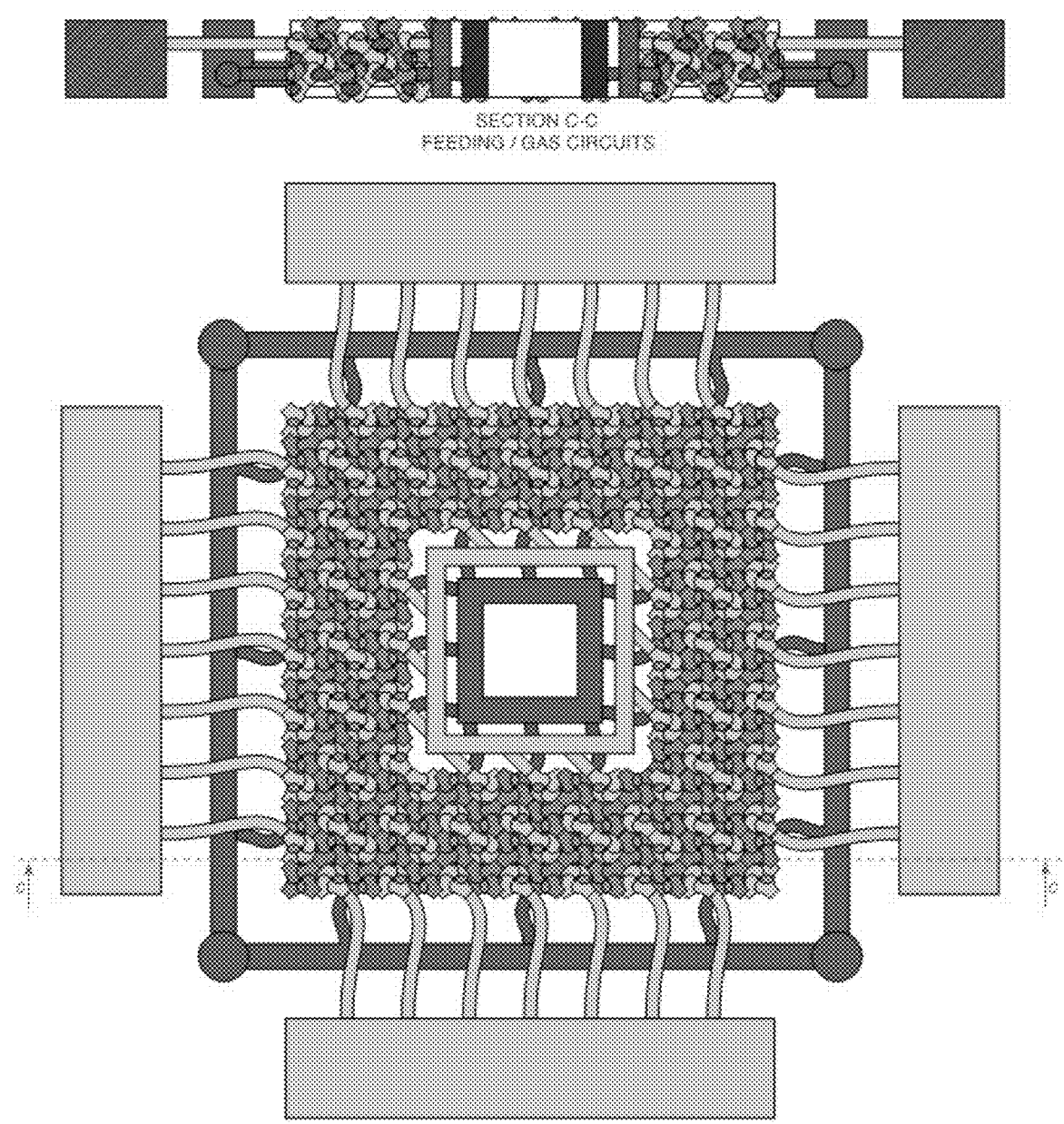

In some embodiments, an assembly of layers of minimodules ("first matrix") can be co-located with a second assembly of layer of minimodules ("second matrix") whereby the second matrix occupies the free spaces left by the first matrix and whereby the matrices occupying the same volume have no point of contact, and maintain a constant minimum distance. An example assembly of two matrices is shown in FIGS. 10A-10F. FIG. 10A shows an example of a portion of a double gyroid inscribed in a cube. FIG. 10B shows an orthogonal and cut away view of the structure of FIG. 10A. FIGS. 10C and 10D show an example of the direction of grown of a second layer with respect to the first layer. FIG. 10E shows and an example of the volume subtracted from a pyramid and counterclockwise growth. FIG. 10F shows an example of clockwise direction of growth of a macrostructure along a vertical axis of a hollow pyramid.

Figure 12:
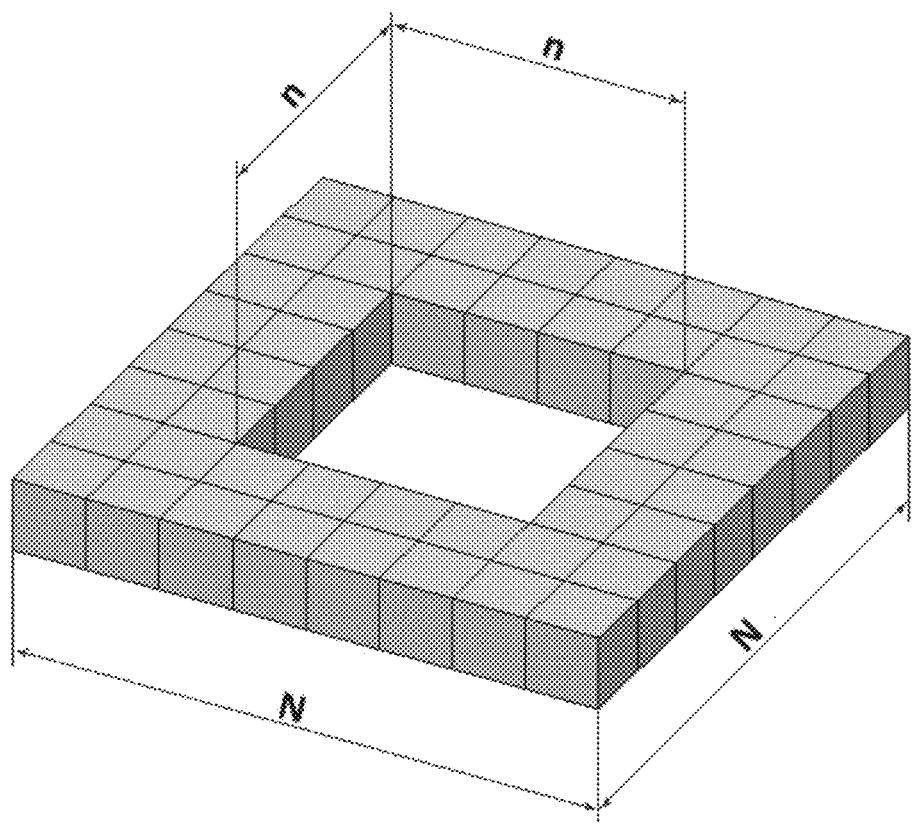
FIG. 12 shows an example layer for a hollow pyramid shape.
Figure 13B:
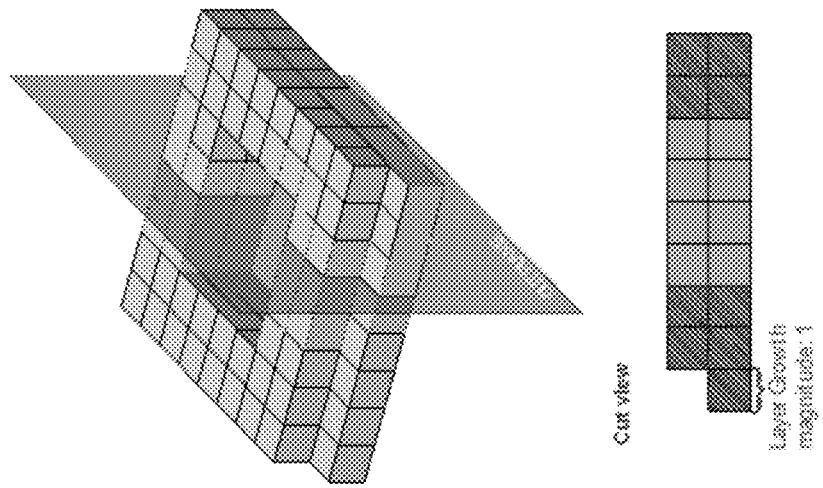
FIGS. 13A and 13B provide an example of growth for a hollow pyramid shape.
Figure 13A:
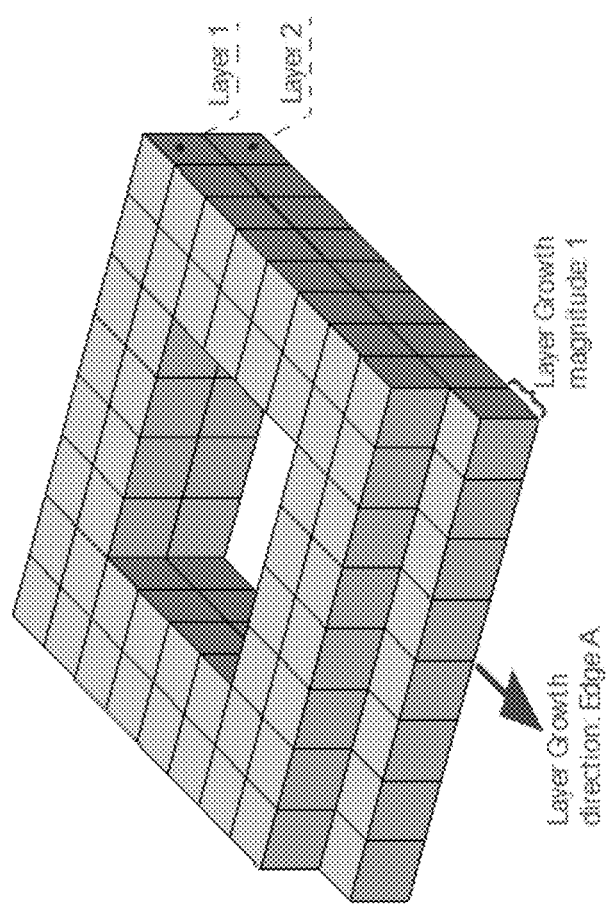

In some embodiments, the minimodules are assembled into a hollow pyramid macrostructure. A hollow pyramid has a volume of hollow center and of increasing transverse section. Using the hollow pyramid macrostructure, the feeding circuit can serve both the external and internal perimeters. For the construction of a hollow pyramid, the matrix has an initial layer that is linked to a distributor and a layer that in turn connects to the collector. The number of upper mouths of the initial layer, as of the lower ones of the layer that connect to the collector may belong to the set $M=2^n$. In this way it is ensured that the connecting channels, or trees, can branch in pairs in a balanced manner. A tree may be a distributed structure (input) and collection (output) of a bubble free bioreactor. In both the input and the output, a channel may transition or branch from a single channel to $2^n$ channels. The increase in volume between layers (this is the number of minimodules that are added between one layer and the next in the flow direction) are determined by the bioreactor and are ordered by (i) an alternating sense of growth between its edges of the outer perimeter; and (ii) an increase of its internal perimeter (i.e. the perimeter of the internal hollow center). For example, if N is the number of modules in one of the edges of the external perimeter of the hollow pyramid, and n is the number of minimodules that make up one of the edges of the internal perimeter of the hollow pyramid, then if at one layer N=(8;8) then n=(4;4) (See FIG. 12). This logic is repeated alternately between the outer edges of the pyramid in each layer and in a clockwise sense (considering the direction of the flow). The result is a stepped pyramid where its steps form a faceted spiral. The internal perimeter also has a spiral growth, but with a lower frequency than the external perimeter, and the direction of growth for the internal perimeter is opposite to that of the external perimeter (See FIGS. 13A and 13B). The interaction between the internal-external spirals and the direction of the flow result in a vortex-type movement of flowing media within the hollow pyramid structure.

In some embodiments, the feeding system is connected to the bioreactor through one or more sub-channel. A subchannel of the feeding circuit can surround the perimeter of one or more layers in a bioreactor at an equivalent distance on each face of a given layer. The subchannels can connect at one or more mouths of minimodules as the edges of a layer. An example set of connections is shown in FIGS. 11A-11F.

Figure 14:
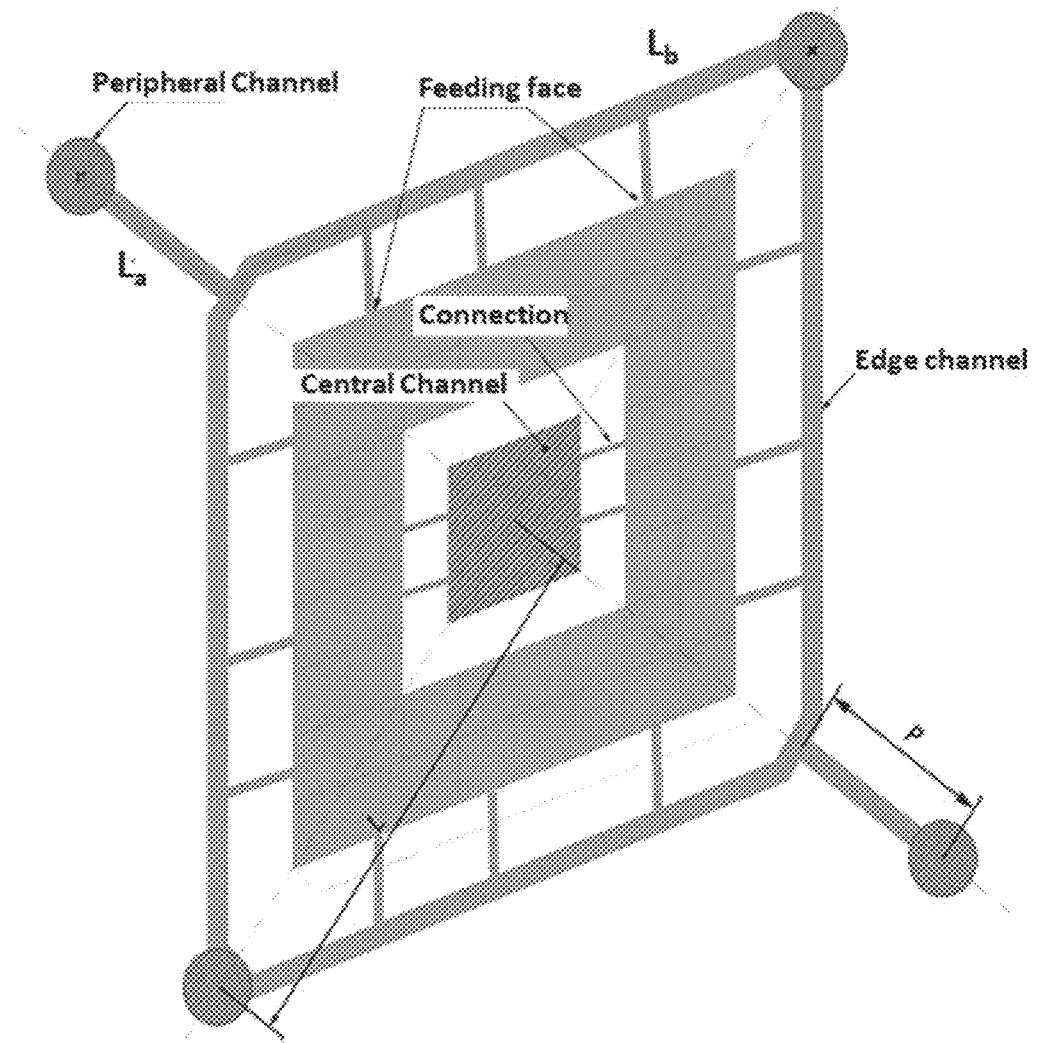
FIG. 14 shows an example of an external feed circuit for a hollow pyramid shape.

In some embodiments, the feeding circuit connects at 1, 2, 3, 4, 5, 6, 7, 8 or more than 8 points to the bioreactor. In one embodiment, the feeding circuit serves a hollow pyramid macrostructure bioreactor and the feeding circuit has a division of 5 subchannels. One of these subchannels extends into the inside of the pyramid Inner channel and the rest feed sub-channels parallel to the edges of each layer (external channels). The pressure and flow balance of the feed circuit is maintained through proportionality of the external and inner channels of the feeding system. An example feeding circuit for a hollow pyramid shape is shown in FIG. 14.

In some embodiments, the macrostructure of the bioreactor is a lamella. In some embodiments, the feeding system is connected the bioreactor through one or more sub-channel. A subchannel of the feeding circuit can surround the perimeter of one or more layers in a bioreactor at an equivalent distance on each face of a given layer. The subchannels can connect at one or more mouths of minimodules as the edges of a layer. An example set of connections is shown in FIGS. 11A-11F.

Figure 15:
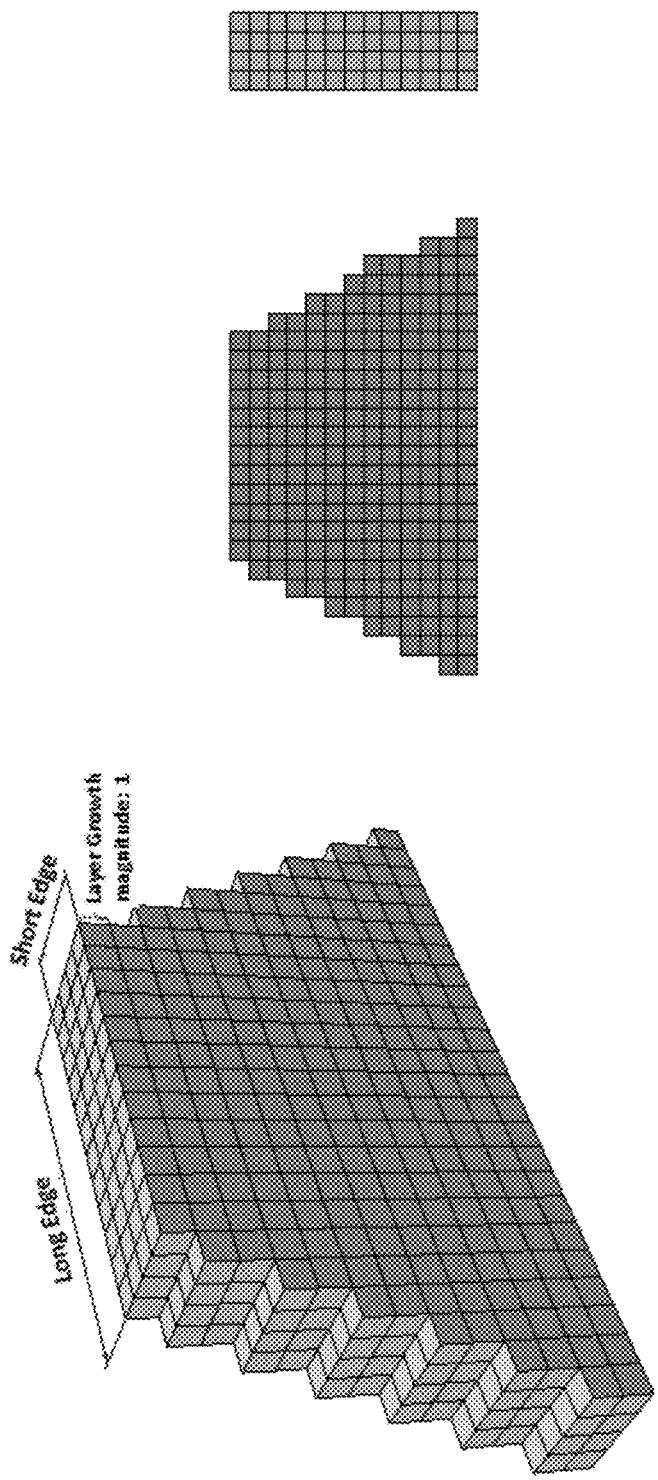
FIG. 15 shows an example of a lamella macrostructure.
Figure 16:
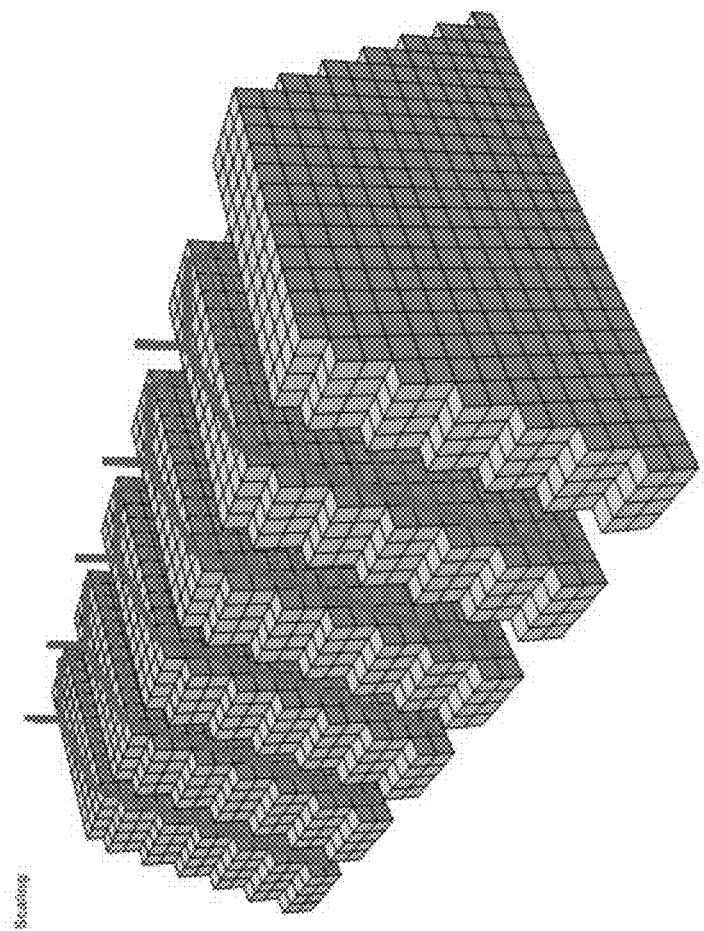
FIG. 16 shows an example of lamella macrostructures with feeding circuits.
Figure 16:
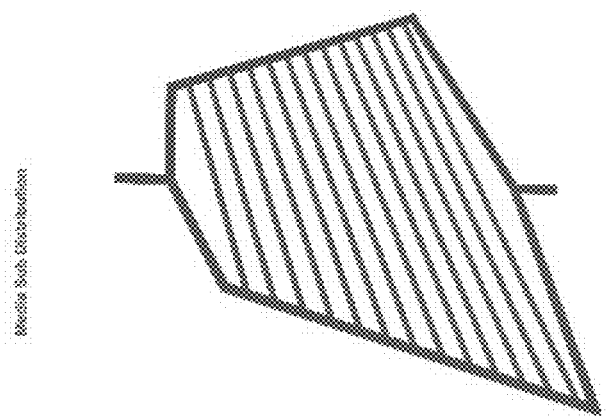

In some embodiments, the bioreactor employs a lamella macrostructure composed of minimodules such as DGs. A lamella macrostructure has a sheet of constant thickness and of increasing cross section comprised of minimodules. The constant thickness of the sheet allows even access of substances from the feeding circuit. The increase in volume between layers (this is the number of modules that are added between one layer and the next in the flow direction) is determined by the bioreactor, and is ordered by an alternating sense of growth between the shortest edges of the sheets (See e.g., FIG. 15). In the lamella macrostructure, there may be one or more than one sheet, for example 2, 3, 4, 5, 6, 7, 8 or more than 8 sheets arranged in parallel. The space between each sheet can be utilized to place the feeding circuit, or a portion thereof which feeds the modules in the sheet (See e.g., FIG. 16).

Figure 17:
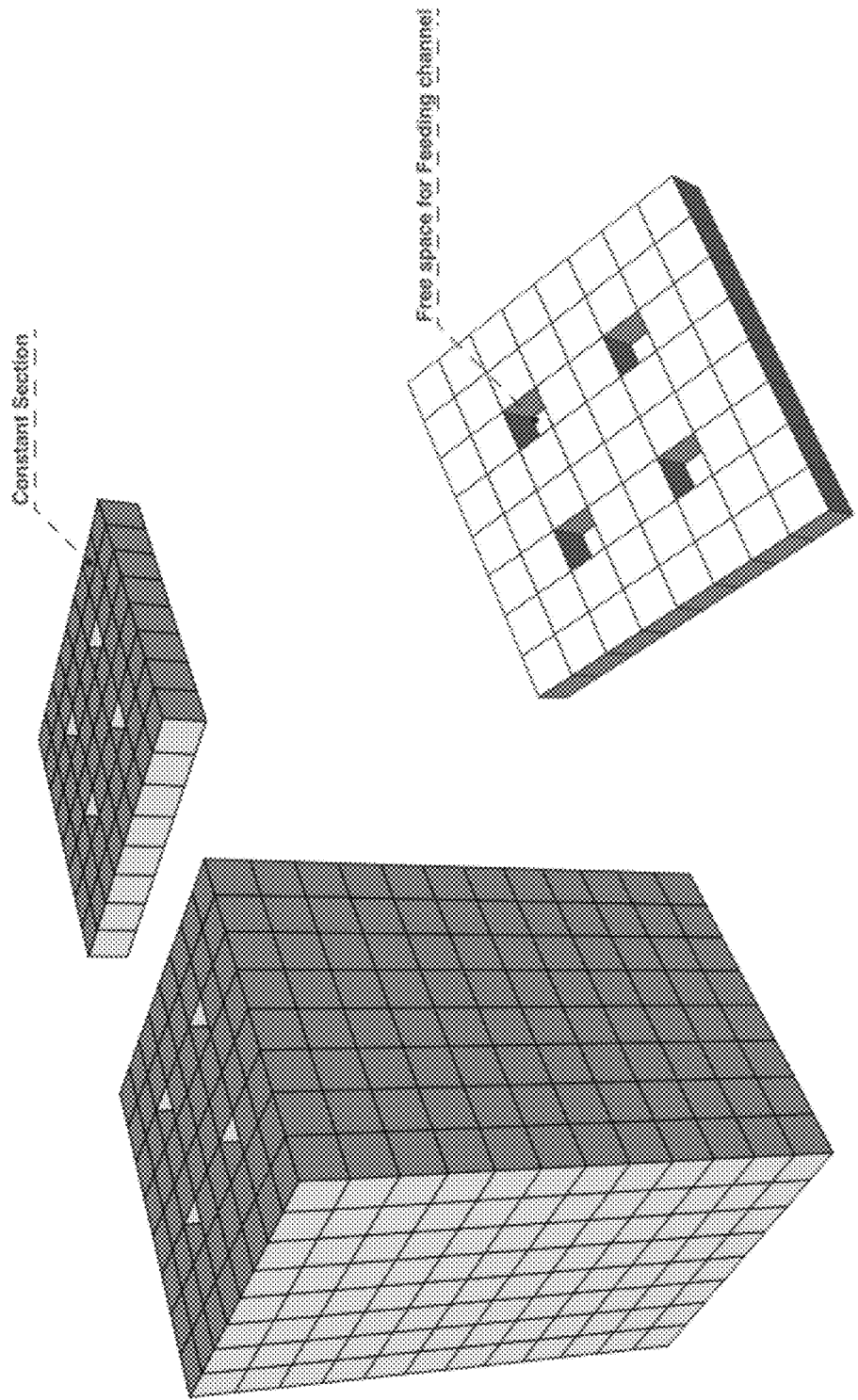
FIG. 17 shows an example macrostructure.
Figure 18:
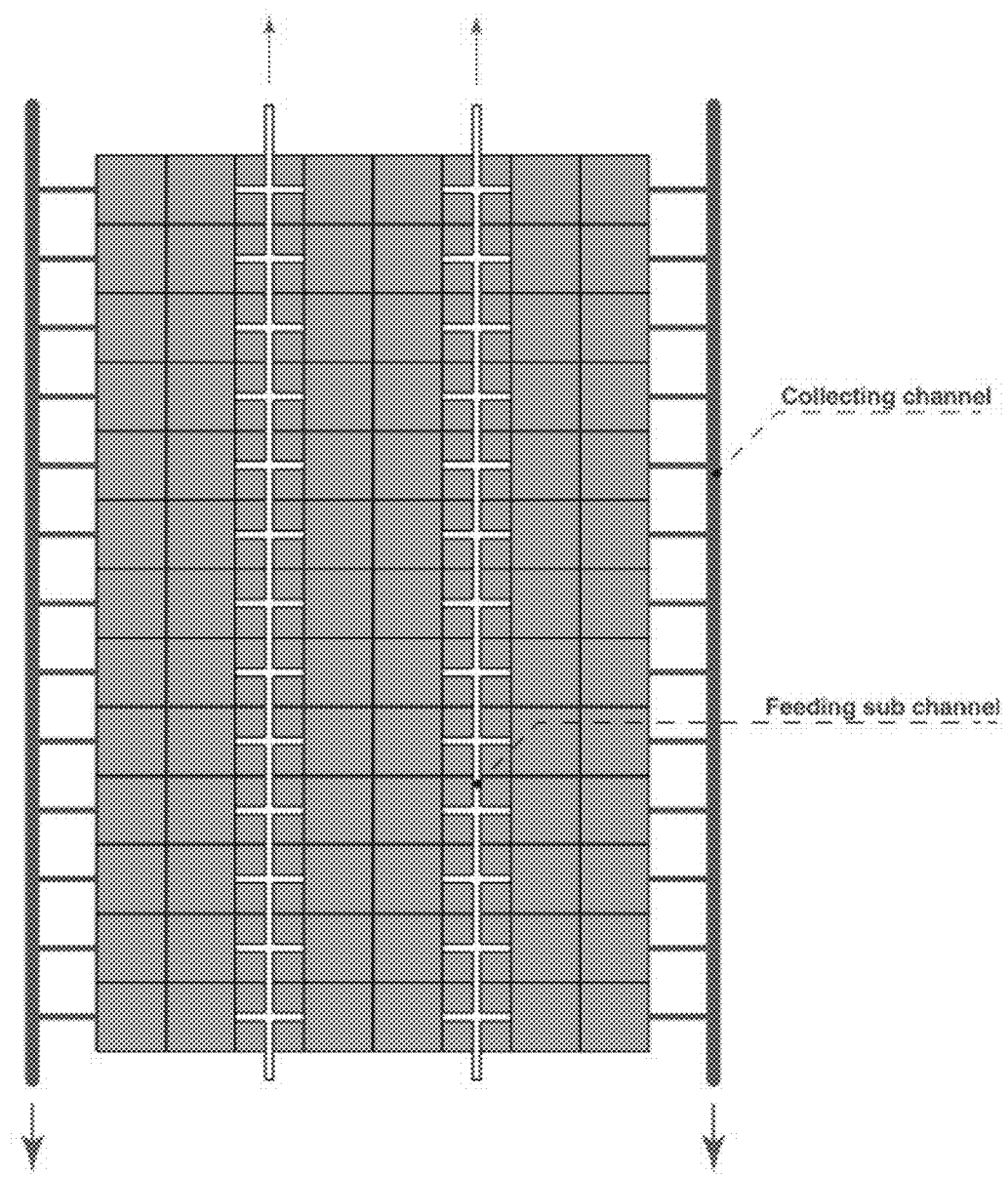
FIG. 18 shows an example feeding and collection arrangement.

In some embodiments, the minimodules are assembled into a tree-chess macrostructure, which has at least one hollow column of constant cross-section that crosses longitudinally the layers of minimodules. In some embodiments, a tree-chess macrostructure has 1, 2, 3, 4, or more than 4 such columns. The columns can be used to provide an area to transport liquid media and other substances through channels that follow the longitudinal column. Collection of spent media, gas, cells and bioproducts can be made on one or more or all of the external faces of the structure, driven by the pressure difference between the center of the column and the faces. An example tree-chess macrostructure is shown in FIG. 17, and example feeding and collection arrangement is shown in FIG. 18.

Bioreactor Connection Systems

Figure 19A:
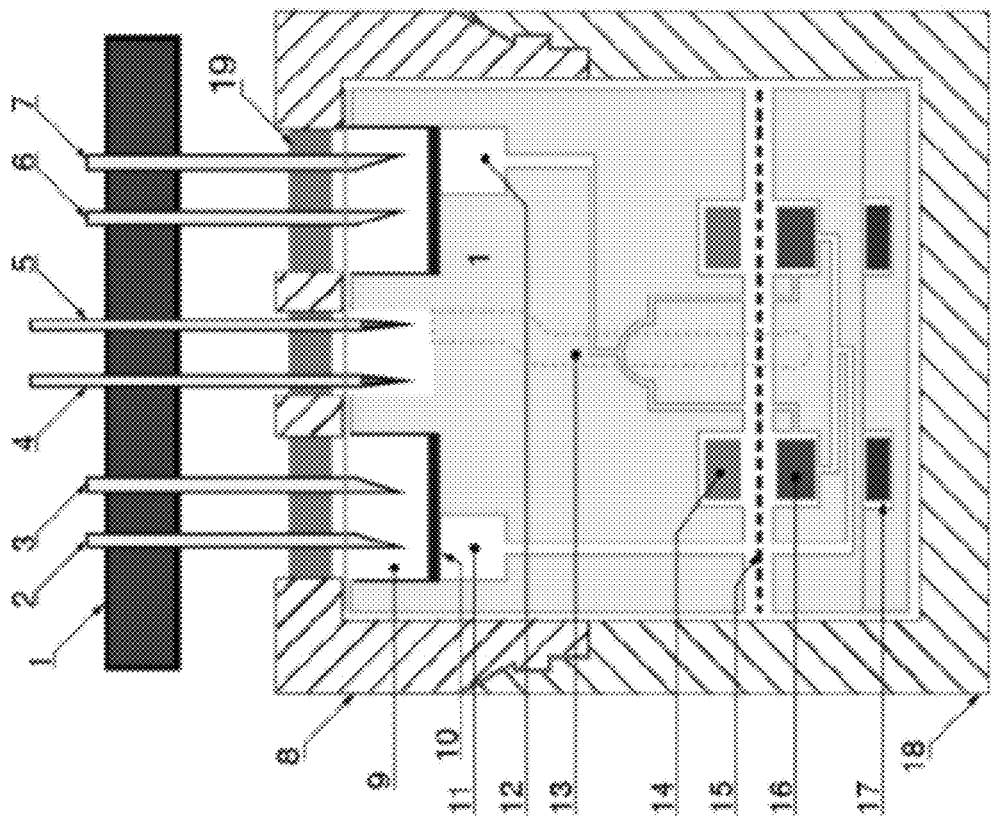
FIGS. 19A-19E shows an example connection system.

The modules may be connected, coupled, or in fluid communication by one or more connection systems. FIGS. 19A and 19B shows an example connection system which includes a connector between cell chip module and a fluid source or fluid collection module. The connector includes a support and a set of hollow needles which permit in the ingress and egress of fluid and/or fluid containing cells. In some embodiments, the connector, through the needles connects to a first module such as a cell chip module. The needles can be arranged as sets such that each set of needles can include a needle for input of fluid and another for output of fluid from the cell chip module. One end of the needle is for entry into a chamber or channel in the cell chip module and the other end of the needle can be connected to a fluid source, to a collection device or another module.

In some embodiments, the set of needles includes at least one input needle and one output needle. In some embodiments, there are a plurality of sets of needles. Each set of needles can be directed to a separate chamber and/or a separate channel to which fluid is directed for input or removed for output.

In some embodiments, the connector can connect the cell chip module to one or more sources of fluid such as culture medium, nutrient supplements, chemical inputs, trypsin, wash/buffer solutions that can be used to supply the cell chip module with fluid and optionally, remove spent fluid. In some embodiments, the connector can connect the cell chip module to a second module such as a sandbox bioreactor or a production bioreactor, such as for transferring cells from one module to the other.

In one embodiment, the connection system includes a cleaning chamber such that the needles are cleansed and/or sterilized prior to entering a module such as a cell chip module. In one embodiment, the cleaning chamber is one or more separate chambers at one end of the cell chip module. The cleaning chamber(s) are bounded on a first end by a septum that contains the cleaning chamber from the environment and through which the needles can perforate from one end into the cleaning chamber. The cleaning chamber can be bounded on a second end by a safety film or other boundary, which can contain cleaning or sterilization fluid (or gas) within the cleaning chamber. The connector in such embodiments, is connected at the other end of the needles to a fluid source such as with cleaning or sanitization agent, and wash solution(s).

On the other side of the safety film or boundary is a channel. Once cleaned and sterilized, the needles can be placed through the safety film or boundary into the channel. The channel can be a culture medium channel which flows culture medium from the needle to other locations in the cell chip. The channel can be a cell harvesting channel, from which cells present in the chip (such as cells growing and multiplying in the chip) can then be directed to the channel and then through a needle to a separate module or harvesting component. The channel can be a waste channel through which spent media can be directed and removed from the chip.

Figure 19C:
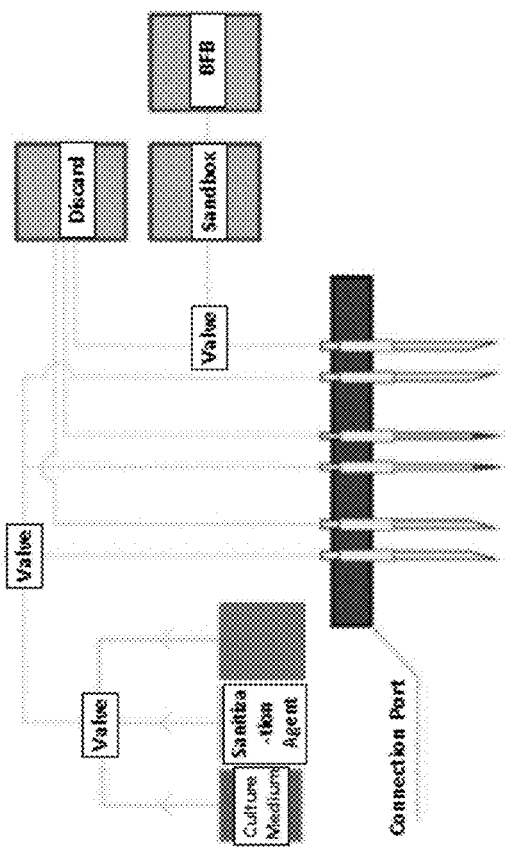
Figure 19B:
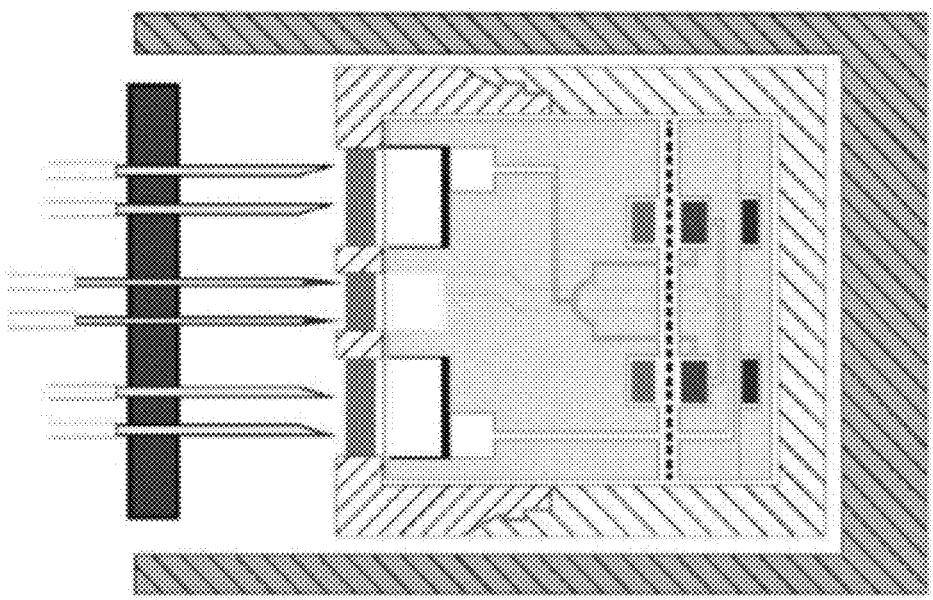

FIG. 19C shows an example embodiment of connections made by the connector system to components containing culture media, sanitization agent, as well as to waste collection and to a sandbox module. Connecting tubes or channels connect from the connector system and utilizes valves to direct fluids from the connector to the appropriate source, collector or module.

Figure 19E:
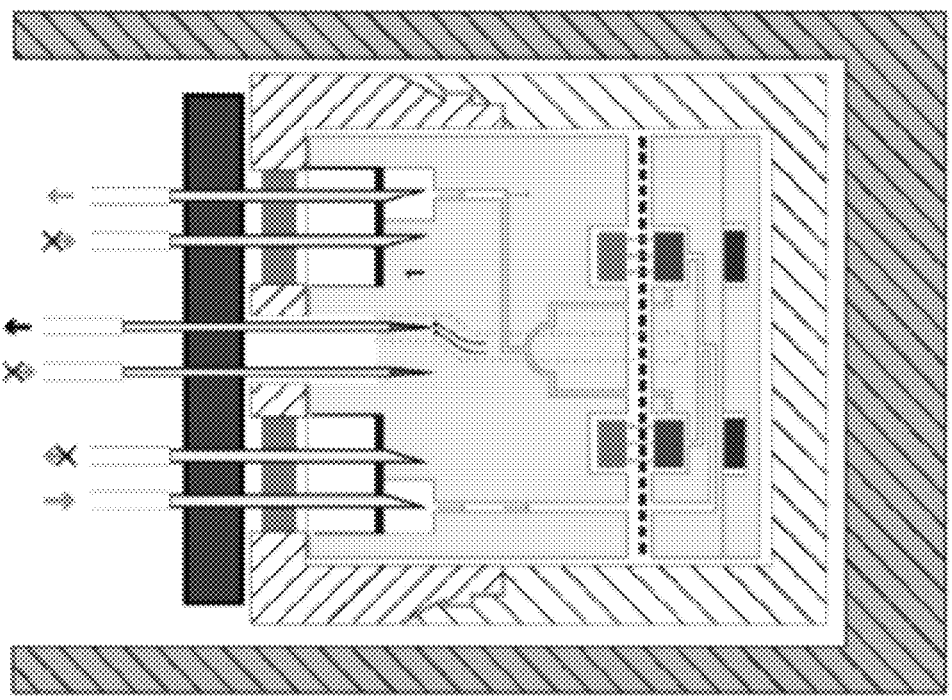
Figure 19D:
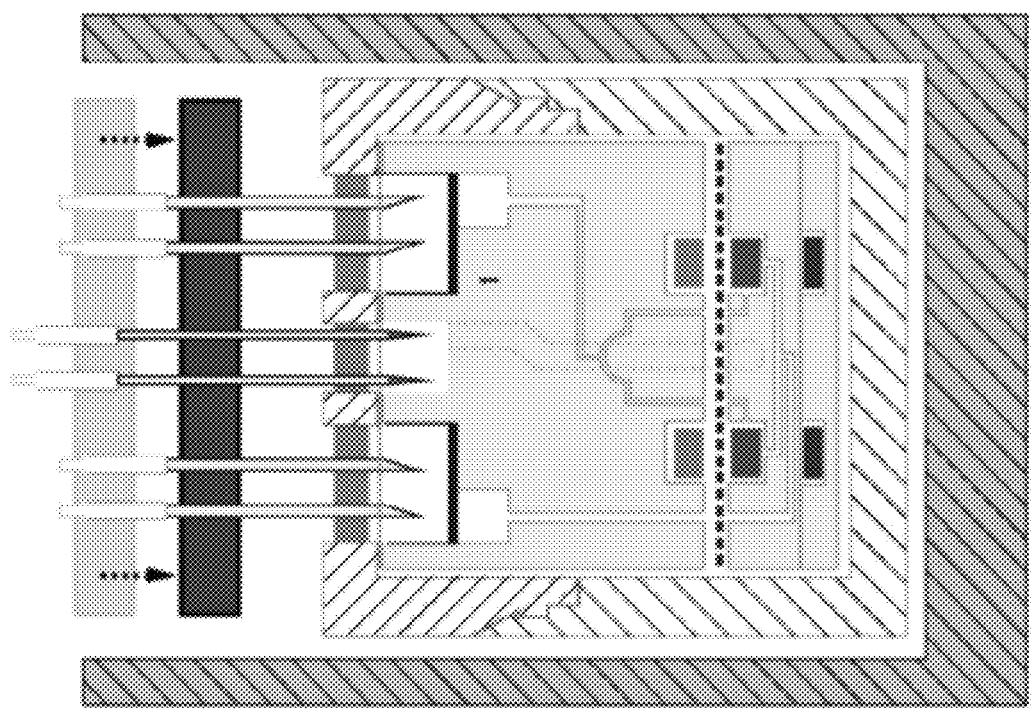

FIG. 19D shows an example embodiment of the connection system with the needles penetrating a first chamber in a cell chip module, such as for cleaning and sterilization, illustrating an example embodiment of the connection system during the process of cleaning, having fluid flow from a component containing sanitization fluid to the sanitizing chambers in the cell chip and having one of each set of needles to remove spent sanitization fluid.

FIG. 19E shows an example embodiment of the connection system with the needles penetrating a second chamber after cleaning/sterilization. The first set of needles (left) is positioned such that the input needle enters a culture media channel/chamber and allows new culture media to flow into the cell chip module. The middle set of needles is positioned so that one needle is positioned for output of spent media and culture waste from a channel in the cell chip module. The third set of needles (right) is positioned so just the output needle enters a chamber/channel and is positioned for output of media and cells from the cell chip module.

Module for Adherent Cell Culture

In another aspect, the present disclosure provides methods for culturing cells. The method may include providing a plurality of cells to an adherent bioreactor. The adherent bioreactor may comprise at least one channel and a microporous membrane. The adherent bioreactor may be a part of a cell chip module or a sandbox bioreactor. At least a portion of the cells may be permitted to adhere to a surface of the at least one channel such that the at least the portion of the plurality of cells grow and/or replicate on the surface of the channel to generate attached cells. A liquid medium may be flowed from the at least one channel through the microporous membrane. Flowing the liquid medium from the channel to through the microporous membrane may wash the adherent cells (such as with fresh media or sterile wash buffer), or may be employed to detach the cells from the surface of the channel or may wash detached cells. The detached cells (e.g., suspended cells) may be collected by flowing another liquid medium with the cells through the channel. The adherent bioreactor may be fluidically coupled to a cell chip module, a sandbox bioreactor, a bioreactor (e.g., production bioreactor), or any combination thereof. The cell chip module may provide cells to the adherent bioreactor. The adherent bioreactor may provide cells to a bioreactor (e.g., production bioreactor).

Figure 20:
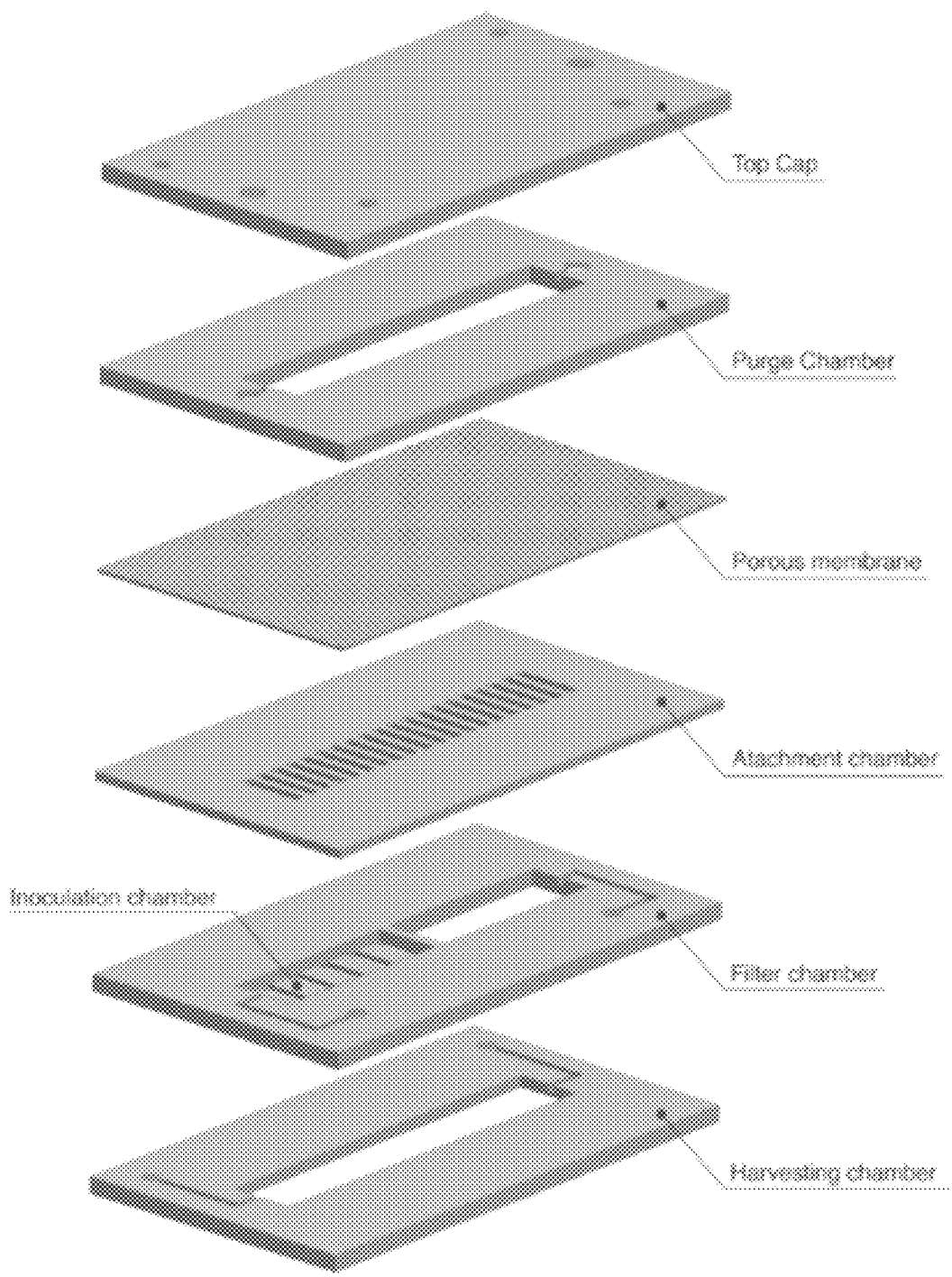
FIG. 20 shows an example multilayer module for adherent cells.
Figure 21A:
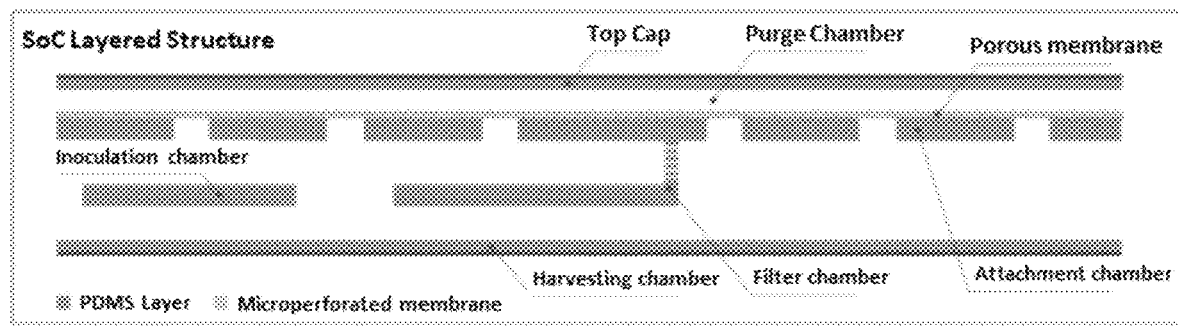
FIG. 21A shows an embodiment of a layer module for adherent cells.
Figure 21B:
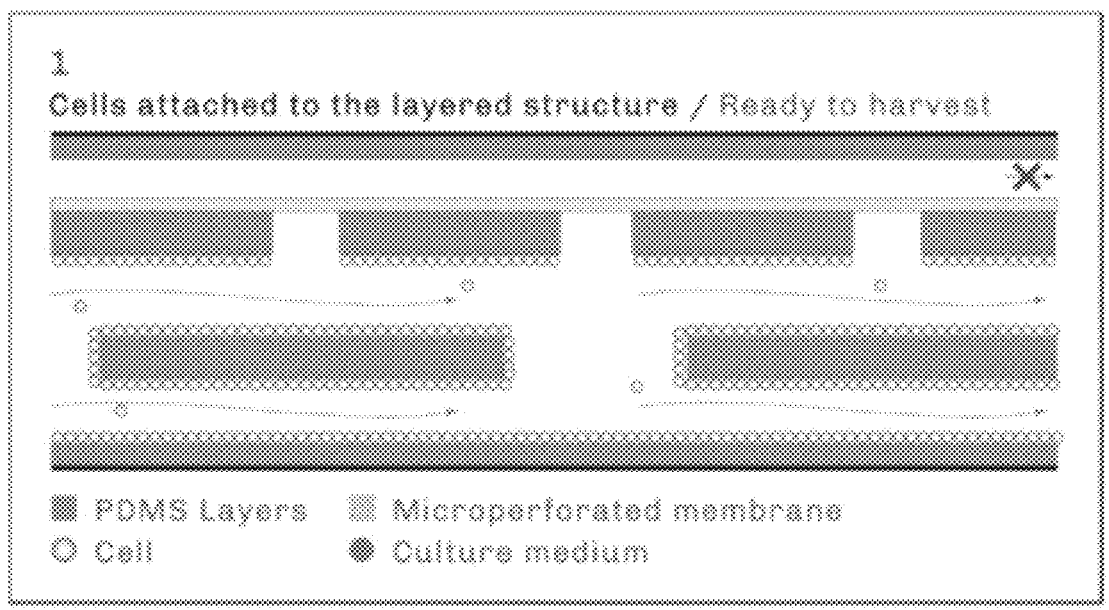
FIG. 21B shows an example of cells attached to a layered structure.
Figure 21C:
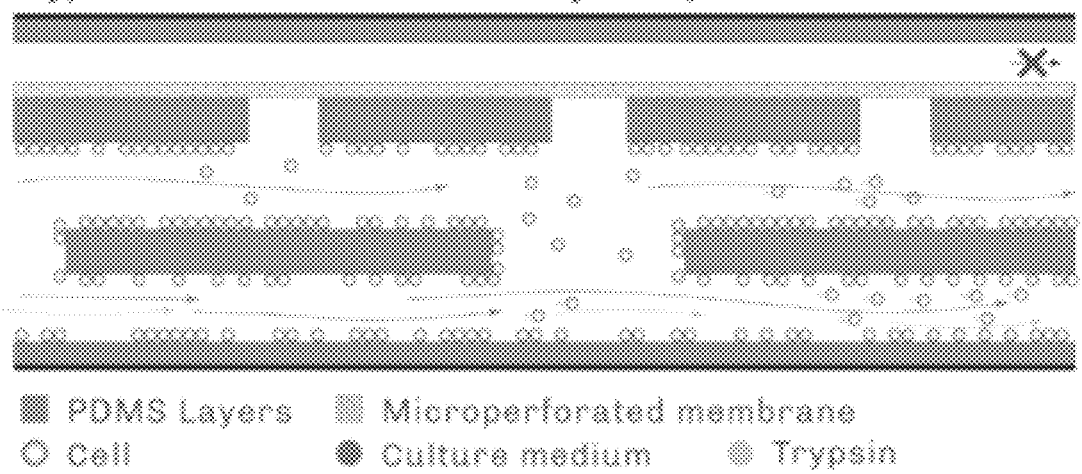
FIG. 21C shows an example of a trypsin wash for cellular detachment.
Figure 21D:
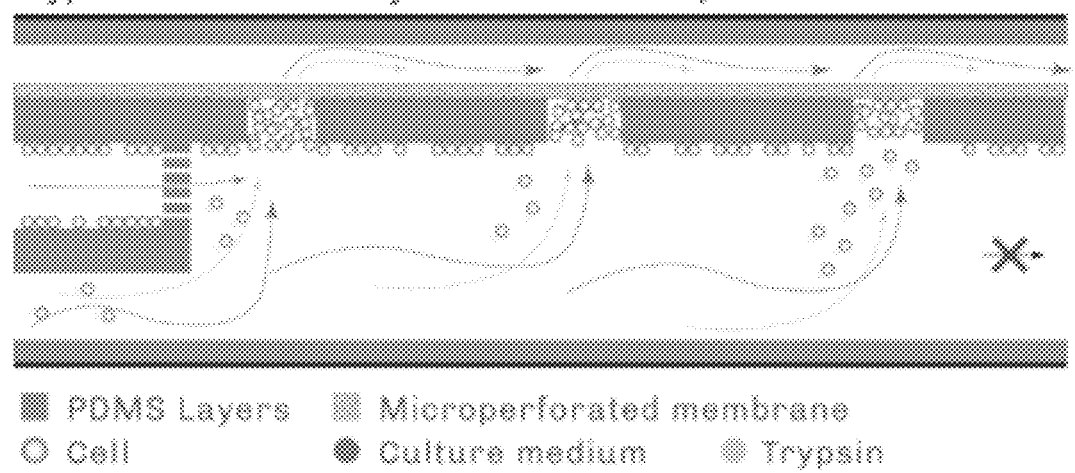
FIG. 21D shows an example of cellular detachment.
Figure 21E:
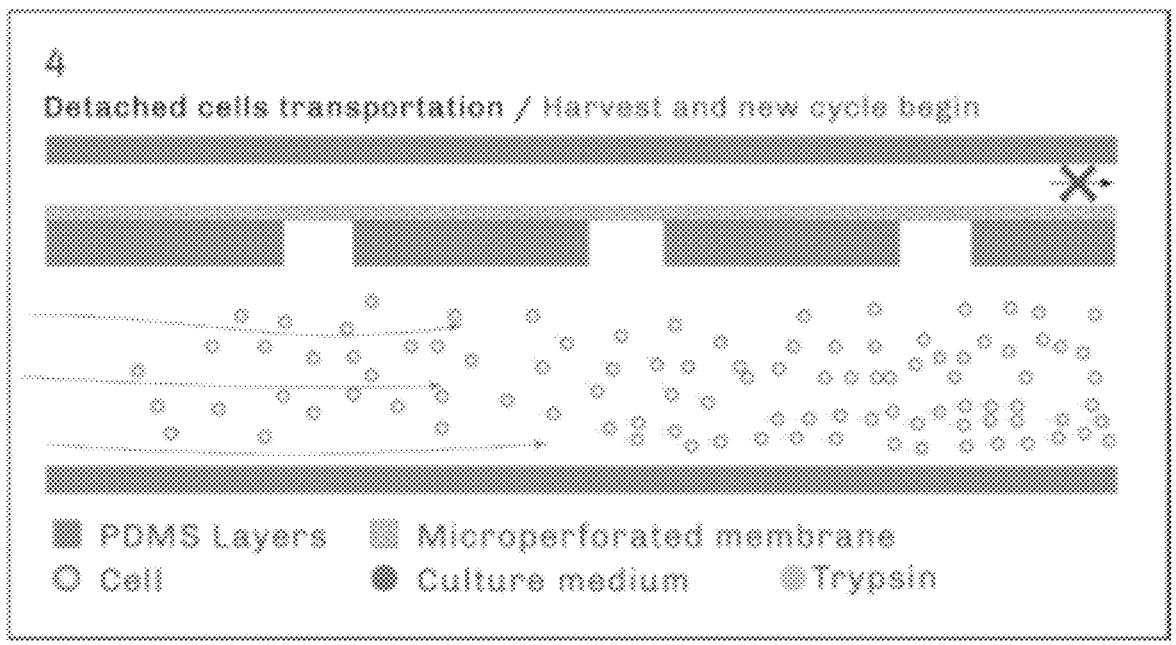
FIG. 21E shows an example of detached cell flow.

Cells may be cultured or grown under controlled conditions on a surface or artificial substrate. For example, cells may be cultured in a monolayer or other surface growth configuration. FIG. 20 shows an example layered module for adherent cell culture. FIG. 21A shows an embodiment of a module suitable for adherent cell culture. The cells can adhere to a material suitable for cell adhesion, such as PDMS. At a selected time point or selected cell density, adherent cells can be removed from the adherent material and released into the surrounding culture media, such as with the addition of enzymes such as trypsin in the liquid flowing past the adherent (e.g., attached) cells such that the cells or a portion thereof can be harvested from the module.

In some embodiments, the adherent material is bounded by one or more open channels whereby culture media flows by the adhered cells. The module can also contain a boundary such as a microperforated membrane that allows culture media or other fluids to pass, but through which cells cannot pass due to the size of the microperforations.

In some embodiments, the module for adherent cells can have one or more chambers. An example embodiment is shown in FIG. 20 having an inoculating chamber for inputting cells into the module, a filter chamber, and attachment chambers. The attachment chambers can have adherent material such that cells adhere to their surface.

Cells can be removed from the adherent positions, such as by including trypsin into the culture media or other fluid flowing past or incubating with the adherent cells. Once the cells are dislodged (such as from the PDMS material), trypsin can be removed by washing with culture media or other fluid, and then such media or fluid passed through the microperforated membrane, leaving the cells behind. Such cells can then be resuspended in fresh media or other liquid, and, the cells or a portion thereof, can be moved using the liquid flow through the channel to a harvest chamber or other output channel for collection.

FIGS. 21B-21E show an example series of cell attachment, trypsinization for cell detachment, and wash and harvesting. In some embodiments, the adherent cell module is a cell chip module or a portion thereof. In some embodiments, the adherent cell module is a sandbox module or a portion thereof. In some embodiments, the adherent cell module is a part of a sandbox module or a portion thereof, such as one or more minimodules.

Computer Systems

Figure 34:
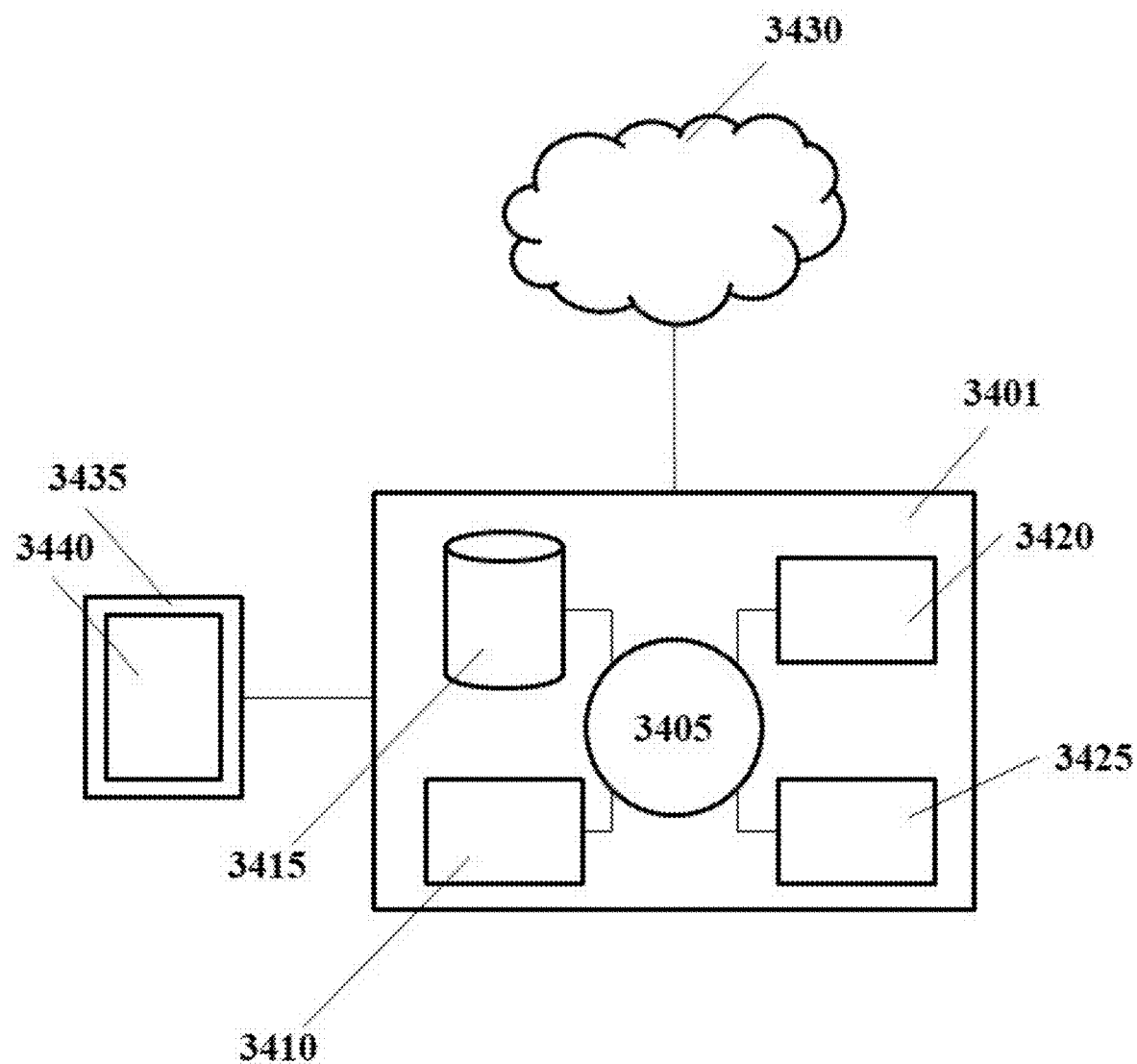
FIG. 34 shows a computer system that is programmed or otherwise configured to implement methods provided herein.

The present disclosure provides computer systems that are programmed to implement methods of the disclosure. FIG. 34 shows a computer system 3401 that is programmed or otherwise configured to control all the internal processes of the systems as programmed, such as media formulation and sterilization, flow control, gas flow rate, pressure and formulation, data acquisition through embedded sensors (e.g., physical, chemical, and biological data), sensor data fusion and commanding control loops, image processing, and creating data sets associated with each process. The computer system 3401 can regulate various aspects of the microenvironment conditions witnessed by the cells within the systems of the present disclosure, such as, for example, media flow rate and subcomponents concentrations, mixing time, reservoir filling; number of pulses, voltage of pulses, duty cycle applied by the electroporator to the media, gas flow and pressure, differential gas solution formulation, differential gas flow for some or all components, differential flow media for some or all components; differential pH values for some or all components; differential dissolved gases for some or all components, differential sugar profile for some or all components, differential temperature for some or all components, sampling time for some or all components, analysis of physical, chemical, biological parameters for some or all components such as temperature, pH, amount and type of dissolved gases, flow, cell density, sugar profile, and biochemical analyses such as proteomics, metabolomics, transcriptomics, and the like. The computer system 3401 can be an electronic device of a user or a computer system that is remotely located with respect to the electronic device. The electronic device can be a mobile electronic device.

The computer system 3401 includes a central processing unit (CPU, also "processor" and "computer processor" herein) 3405, which can be a single core or multi core processor, or a plurality of processors for parallel processing. The computer system 3401 also includes memory or memory location 3410 (e.g., random-access memory, read-only memory, flash memory), electronic storage unit 3415 (e.g., hard disk), communication interface 3420 (e.g., network adapter) for communicating with one or more other systems, and peripheral devices 3425, such as cache, other memory, data storage and/or electronic display adapters. The memory 3410, storage unit 3415, interface 3420 and peripheral devices 3425 are in communication with the CPU 3405 through a communication bus (solid lines), such as a motherboard. The storage unit 3415 can be a data storage unit (or data repository) for storing data. The computer system 3401 can be operatively coupled to a computer network ("network") 3430 with the aid of the communication interface 3420. The network 3430 can be the Internet, an internet and/or extranet, or an intranet and/or extranet that is in communication with the Internet. The network 3430 in some cases is a telecommunication and/or data network. The network 3430 can include one or more computer servers, which can enable distributed computing, such as cloud computing. The network 3430, in some cases with the aid of the computer system 3401, can implement a peer-to-peer network, which may enable devices coupled to the computer system 3401 to behave as a client or a server.

The CPU 3405 can execute a sequence of machine-readable instructions, which can be embodied in a program or software. The instructions may be stored in a memory location, such as the memory 3410. The instructions can be directed to the CPU 3405, which can subsequently program or otherwise configure the CPU 3405 to implement methods of the present disclosure. Examples of operations performed by the CPU 3405 can include fetch, decode, execute, and writeback.

The CPU 3405 can be part of a circuit, such as an integrated circuit. One or more other components of the system 3401 can be included in the circuit. In some cases, the circuit is an application specific integrated circuit (ASIC).

The storage unit 3415 can store files, such as drivers, libraries and saved programs. The storage unit 3415 can store user data, e.g., user preferences and user programs. The computer system 3401 in some cases can include one or more additional data storage units that are external to the computer system 3401, such as located on a remote server that is in communication with the computer system 3401 through an intranet or the Internet.

The computer system 3401 can communicate with one or more remote computer systems through the network 3430. For instance, the computer system 3401 can communicate with a remote computer system of a user (e.g., Virtual Private Networks, Computer hosted in services such as Amazon Web Services (AWS), Satellite communication). Examples of remote computer systems include personal computers (e.g., portable PC), slate or tablet PC's (e.g., Apple® iPad®, Samsung® Galaxy Tab®), telephones, Smart phones (e.g., Apple® iPhone®, Android-enabled device, Blackberry®), or personal digital assistants. The user can access the computer system 3401 via the network 3430.

Methods as described herein can be implemented by way of machine (e.g., computer processor) executable code stored on an electronic storage location of the computer system 3401, such as, for example, on the memory 3410 or electronic storage unit 3415. The machine executable or machine readable code can be provided in the form of software. During use, the code can be executed by the processor 3405. In some cases, the code can be retrieved from the storage unit 3415 and stored on the memory 3410 for ready access by the processor 3405. In some situations, the electronic storage unit 3415 can be precluded, and machine-executable instructions are stored on memory 3410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 3401, can be embodied in programming. Various aspects of the technology may be thought of as "products" or "articles of manufacture" in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3401 can include or be in communication with an electronic display 3435 that comprises a user interface (UI) 3440 for providing, for example, settings, bioprocess report listing measured variables in real time of every stage of the system, capabilities to export and import files (e.g., configuration files, updates), calibration, alarms, (e.g., errors, maintenance, replacement of consumables). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3405. The algorithm can, for example, adjust variables of the control systems using feedback loops, detect problems in the process by image recognition and pattern analysis, fuzzy logic and with hard and soft threshold enforcements, correlate specific and unspecific data through machine learning (e.g., Supervised, Unsupervised and/or Reinforcement) to optimize process conditions within the system, the process outcomes, modelling behavior and simulation.

EXAMPLES

Example 1: Simulation of Fluid Flow and Mixing in Layers of Minimodules

Considering that the flow is laminar, the simulation can be solved in two instances; the velocity field on the one hand, and the advective-diffusive transport of the microorganisms to be analyzed by another. In this case, it was decided to use two species (S1 and S2) that enter with a certain concentration for each branch of entrance of the module, or of the entrances of the different coupled modules. The diffusion values were established according to the diffusion coefficient of fluorescein in water for S1, and a diffusion coefficient 2 orders of magnitude lower for S2.

The progress and mixing process between streams was simulated with an average rate of income considered at a constant 5 micrometer per second (μm/sec), and the concentration of the species was traced from the exit through the whole section. A concentration of 50% of the income value can be expected from good mixing, given that the flows for both income branches are equal.

Figure 22A:
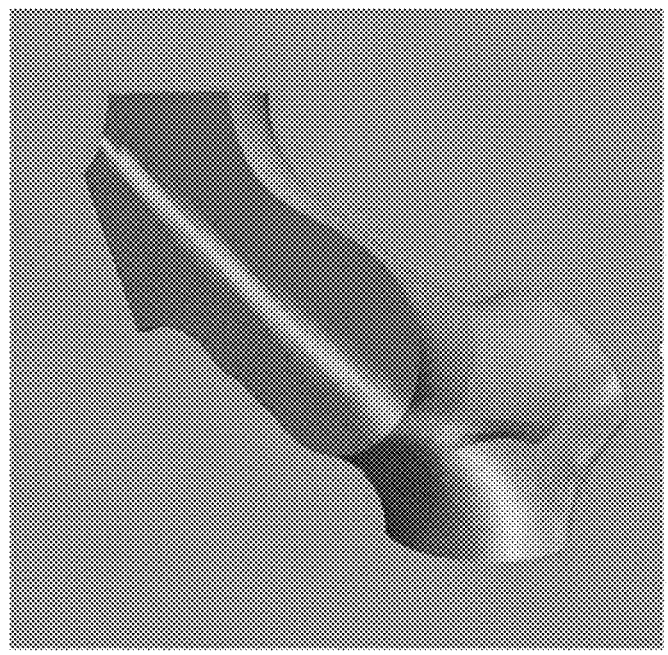
FIG. 22A shows a cut-away view of an example minimodule.
Figure 22B:
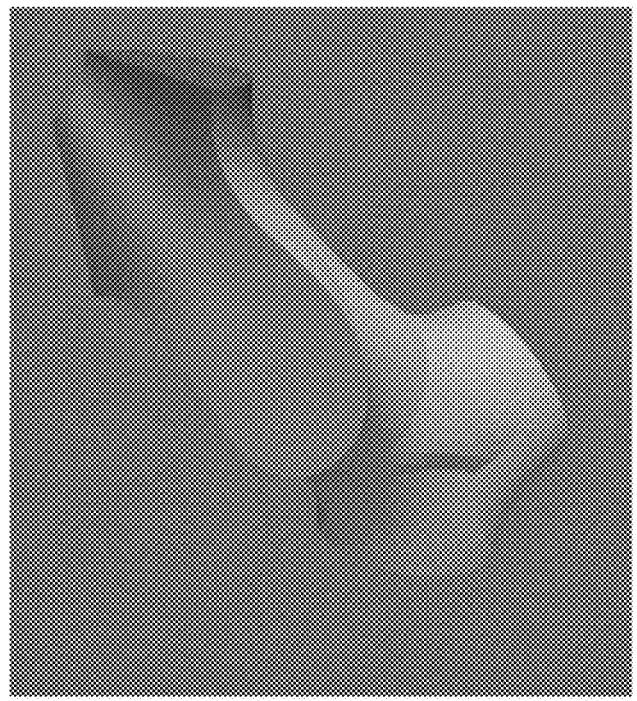
FIG. 22B shows a cut-away of an example minimodule with increased mixing.
Figure 23A:
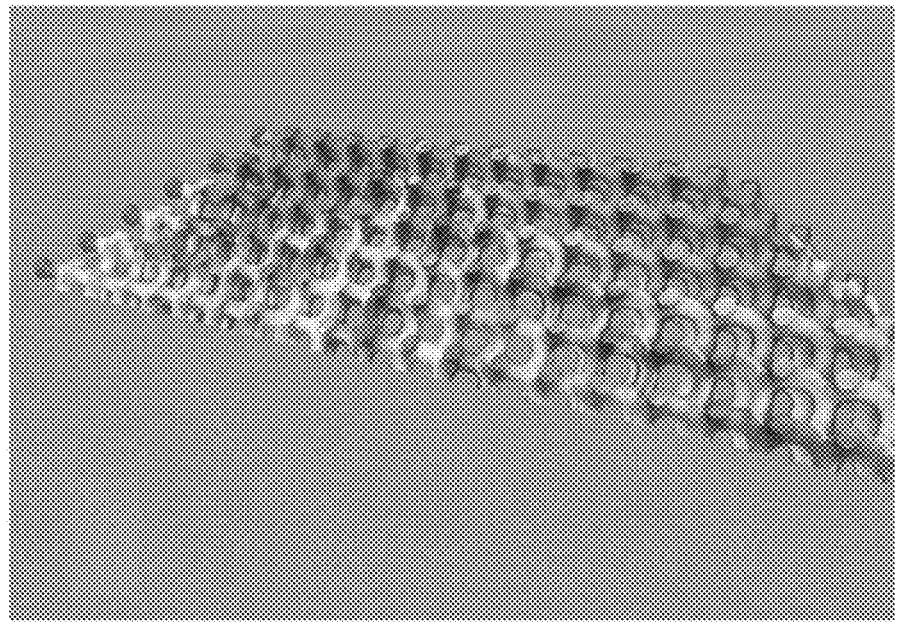
FIG. 23A shows an example assemblage of ten minimodules.
Figure 23B:
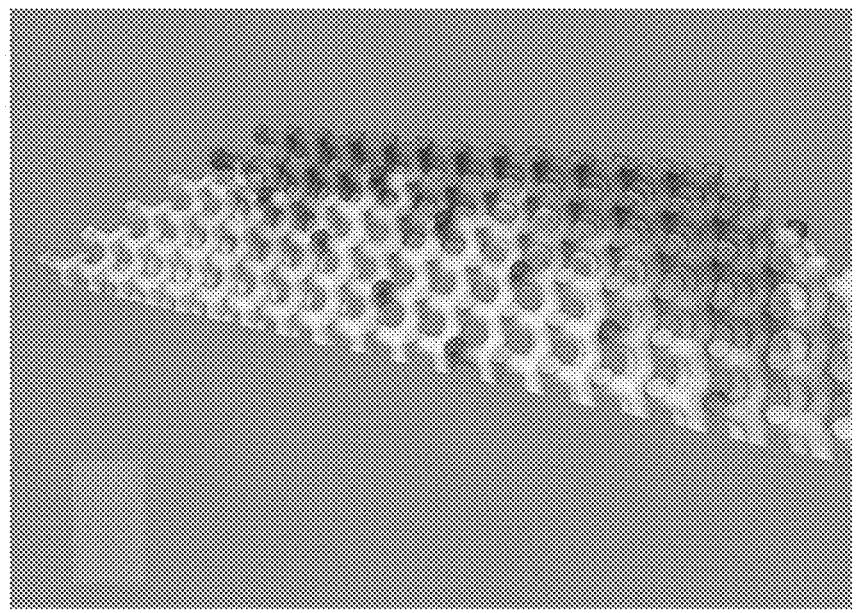
FIG. 23B shows an example assemblage of ten minimodules with increased mixing.
Figure 25A:
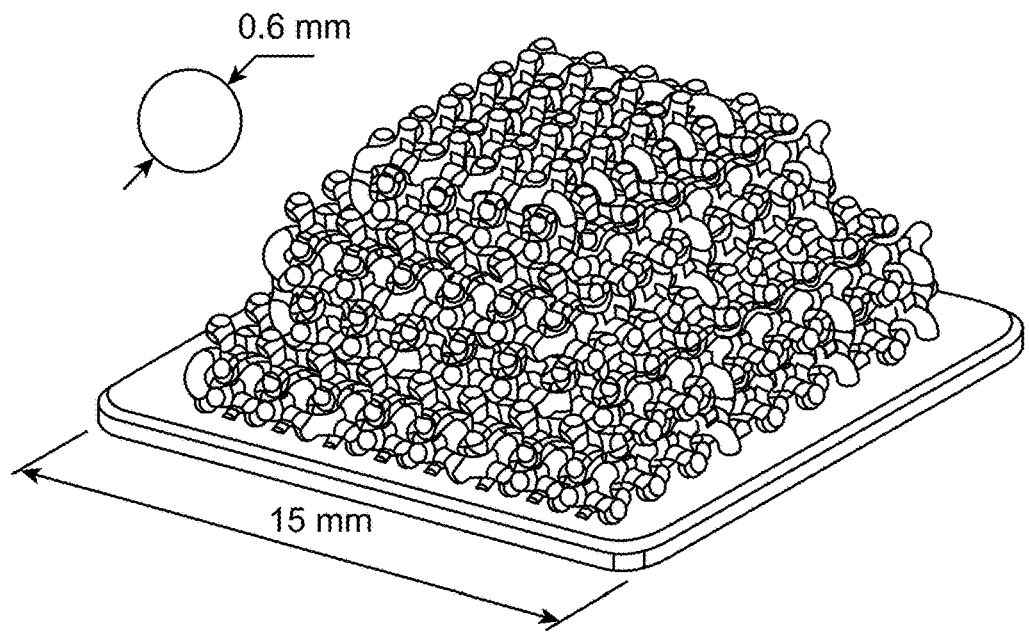
FIG. 25A shows an isometric view of an example macrostructure.
Figure 25B:
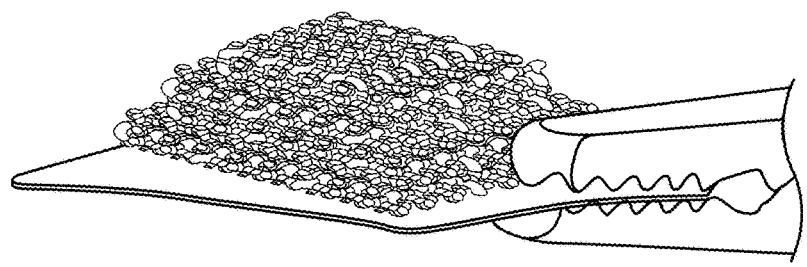
FIG. 25B shows an example printed macrostructure.
Figure 25C:
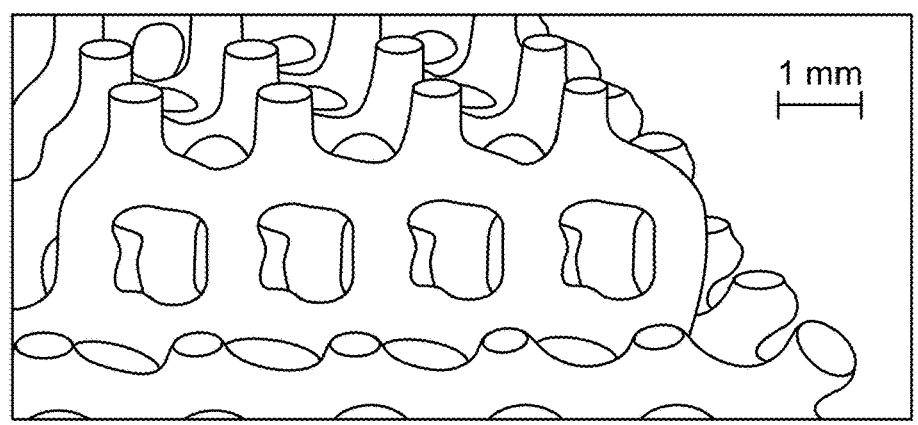
FIG. 25C shows an example printed macrostructure made from a commercial resin.

In FIG. 22A a cut-away view of a single minimodule is showing a poor or low mixed situation caused by a low diffusion coefficient of the species, while in FIG. 22B the diffusion coefficient is higher and the successful mixing can be appreciated. FIGS. 23A-23B shows the result of an assemblage of ten minimodules that were subjected to the simulation process. The scalar distribution (representing the cells) and the concentration of culture medium (color) are shown. It can be observed, on one hand, that this particular distribution of minimodules, with the cells entering from the top, and the culture medium entering through the laterals, the cells do not exit at all the lower exits and the culture medium is not evenly distributed (due to the short flow path in the simulation). FIGS. 25A-25C shows another arrangement of minimodules simulation was carried out with 6 levels of modules. In this arrangement, the first level starts with a greater number of modules, so that the percentage growth of modules in each level is smaller (1 module column is added by row/layer) and a different culture medium income array with fewer mouths was used. In this arrangement, both the distribution of cells and the distribution of medium cultivation are suitably uniform.

Example 2: Construction of a Macrostructure of Minimodules

Figure 24:
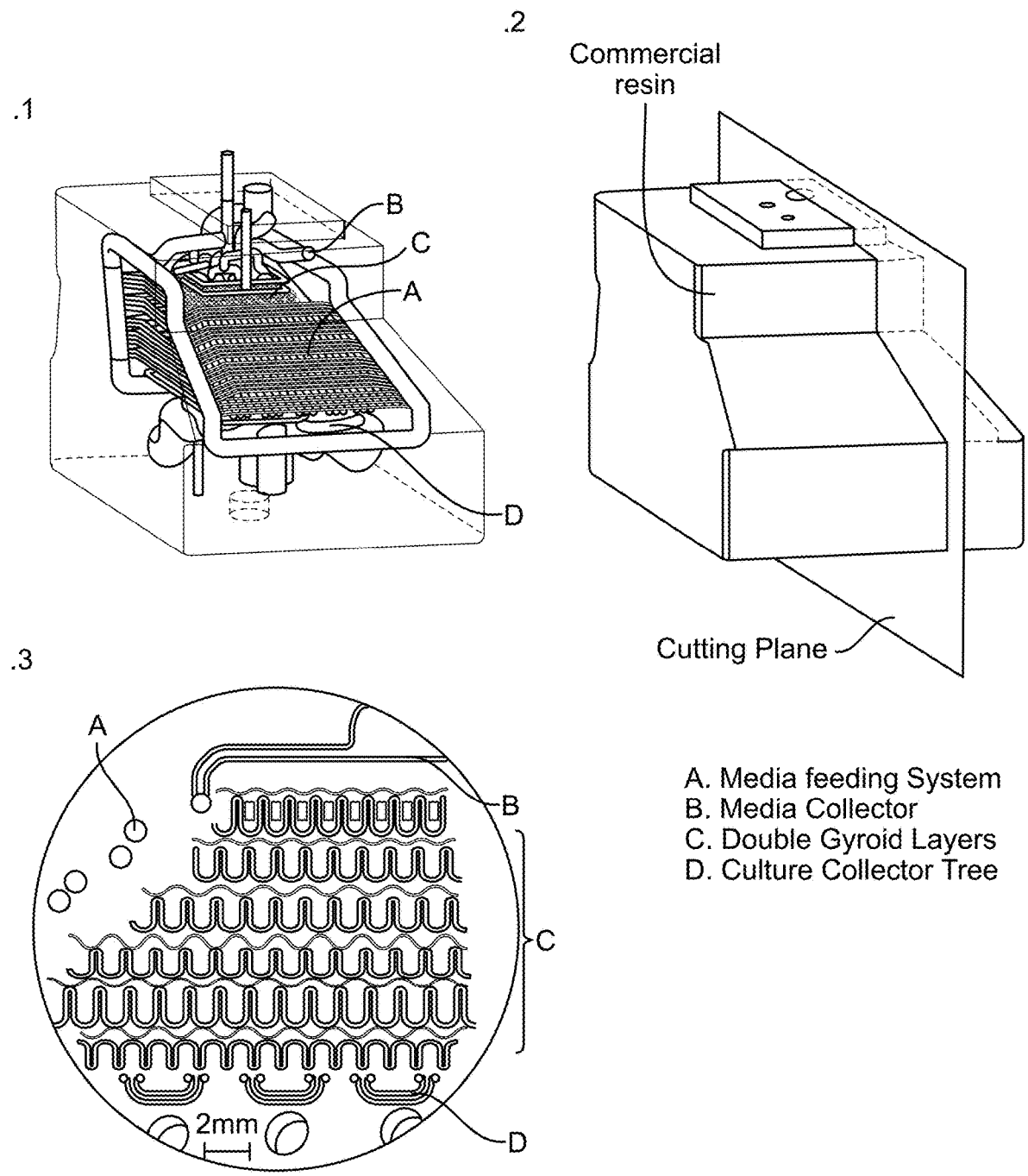
FIG. 24 shows an example bioreactor design with a macrostructure.

A bioreactor was designed using a macrostructure shown in FIG. 24, composed of layers of DG minimodules, and having a feeding circuit as shown. A SLA 3-D Printer (Peopoly Moai) with commercial resin was employed to 3-D print including all systems and connections. The printed bioreactor, as a cutaway view, is shown in FIGS. 23A and 23B.

Additional bioreactors were printed with an SLA printer and photocurable resin. The design included two phases in "positive form" (the volumes of both phases intertwined without intermembrane). FIG. 25A shows an isometric view of the test file used, including a few layers of double gyroid (diameter: 600 micrometers (μm)) and a solid base for better manipulation. Note that the feeding systems of each phase were not placed. FIG. 25B shows a successfully printed test file on PEGDA photocurable resin and FIG. 25C a successfully printed test file with a commercial resin.

Example 3: Demonstration of Fluid Flow Through Minimodules

Figure 26A:
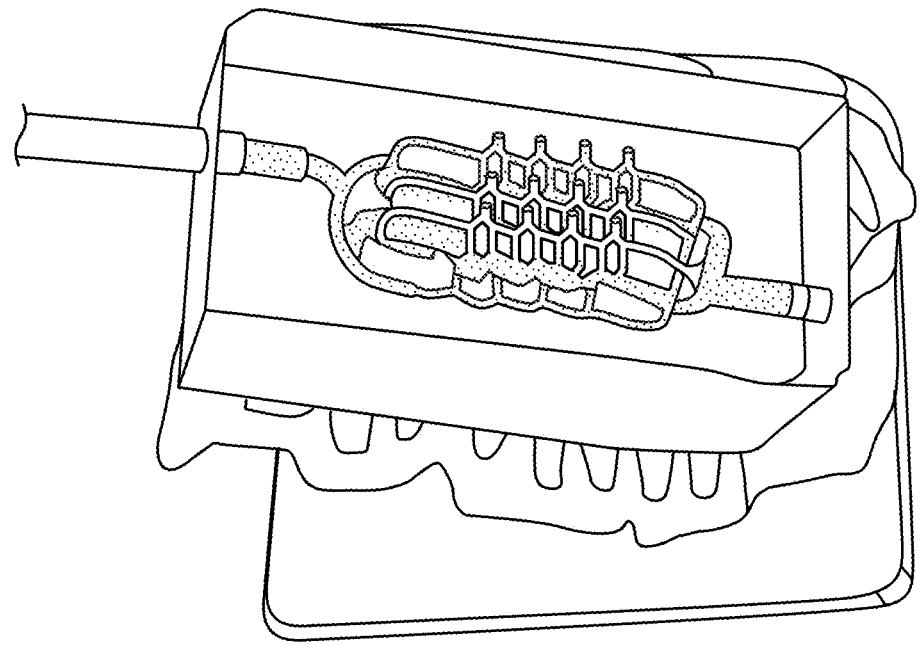
FIG. 26A shows an example bioreactor circuit saturated with dye.
Figure 26B:
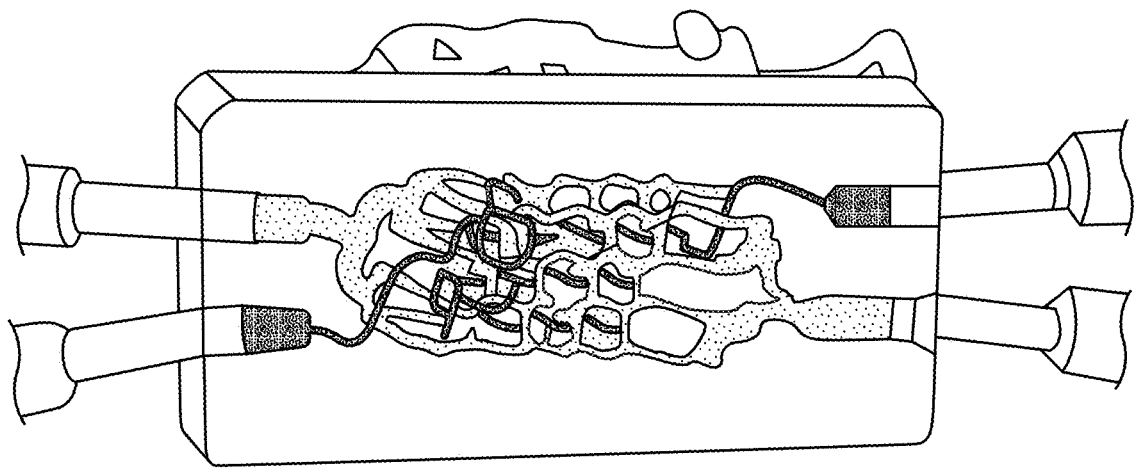
FIG. 26B shows an example double gyroid structure saturated with dye.

A Direct Light Projection type 3-D printer with commercial resin was used to print a matrix composed of 4 layers and rows of 4×2 modules with input/output connection, where the diameter of gyroid was 500 μm). The printed bioreactor was injected at one input connection with red dye. FIG. 26A shows the circuit saturated with red dye. A second printing was performed composes of a first and second matrix to form the double gyroid, both gyroids with diameter 500 μm. One matrix was injected with red dye at an input connection, and the other matrix injected with blue dye. FIG. 26B shows the 2 matrices differentiated by color.

Example 4: Strain on a Chip

Figure 27:
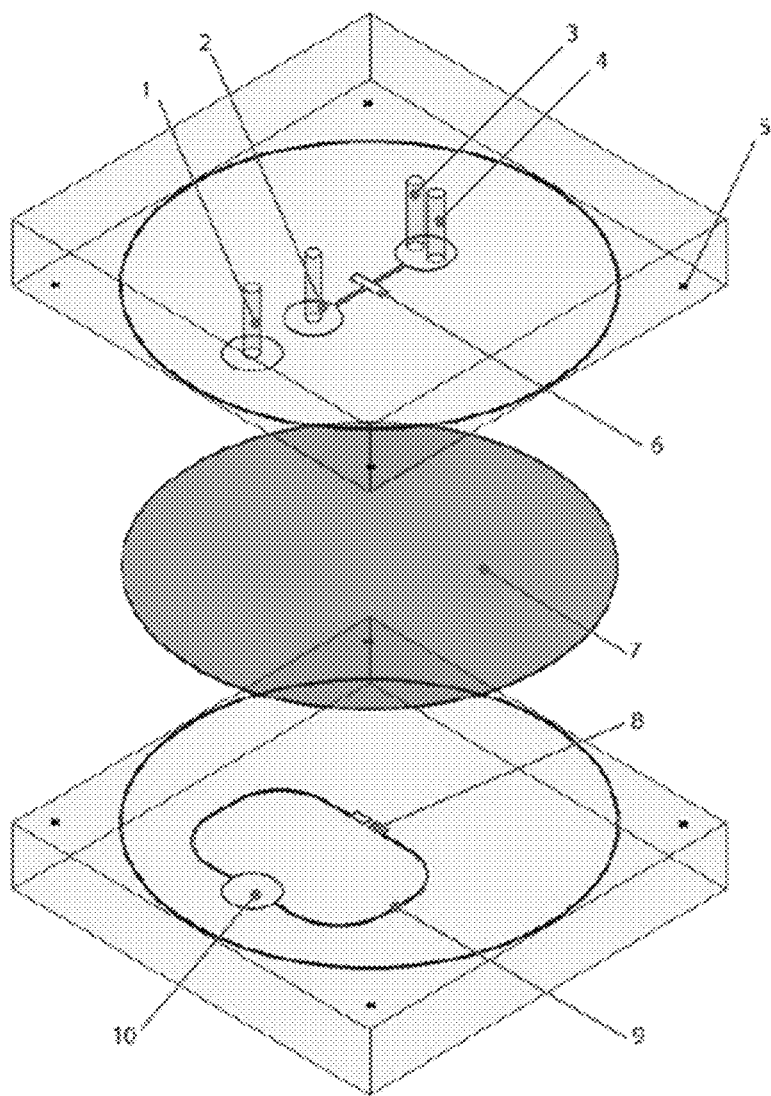
FIG. 27 shows an example design for an example strain on a chip.
Figure 28:
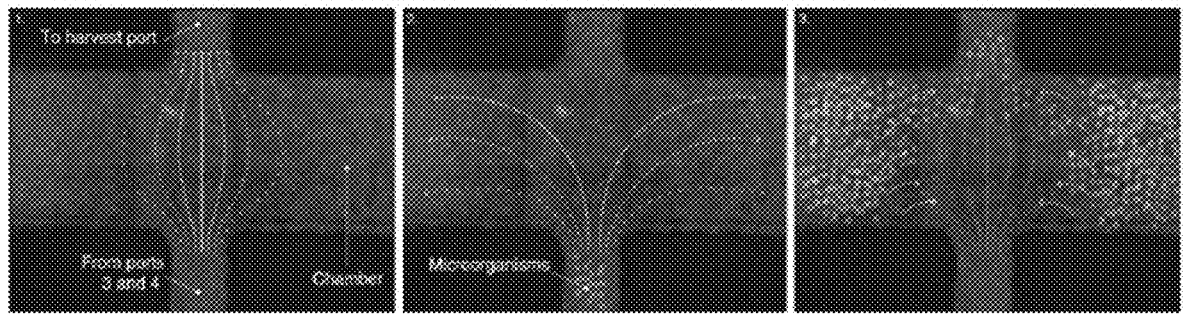
FIG. 28 shows an example of particle flow in a chamber.

An example strain on a chip embodiment was constructed using the design shown in FIG. 27. FIG. 28 shows a progression of images through time obtained in an assay. To simulate the microorganisms, glass particles with an approximate average diameter of 50 microns were introduced to the structure as follows.

With port 2 closed, a distilled water flow was applied from port 3 to 1. In an initial stage the circuits were saturated with lyophilized water for the simulation; for microorganism inoculation the circuits may first be saturated with culture medium. The harvest output (2) was closed and the chip was "inoculated" with the glass particles to simulate microorganisms. The behavior of the flow transports the particles to the chamber and once the port 2 is opened, the suction effect through the porous membrane kept most of the particles in place.

The circuit has input ports 3-4 and an output of culture medium (1). With this configuration, the main circuit is inoculated through port 3, together with the introduction of liquid medium (here water) in port 4. The balance of pressures forces the culture medium to occupy the secondary circuit and leave the circuit by output port 1. The porous membrane functioned as a filter, leaving simulated microorganisms trapped in the main circuit chamber.

Figure 29:
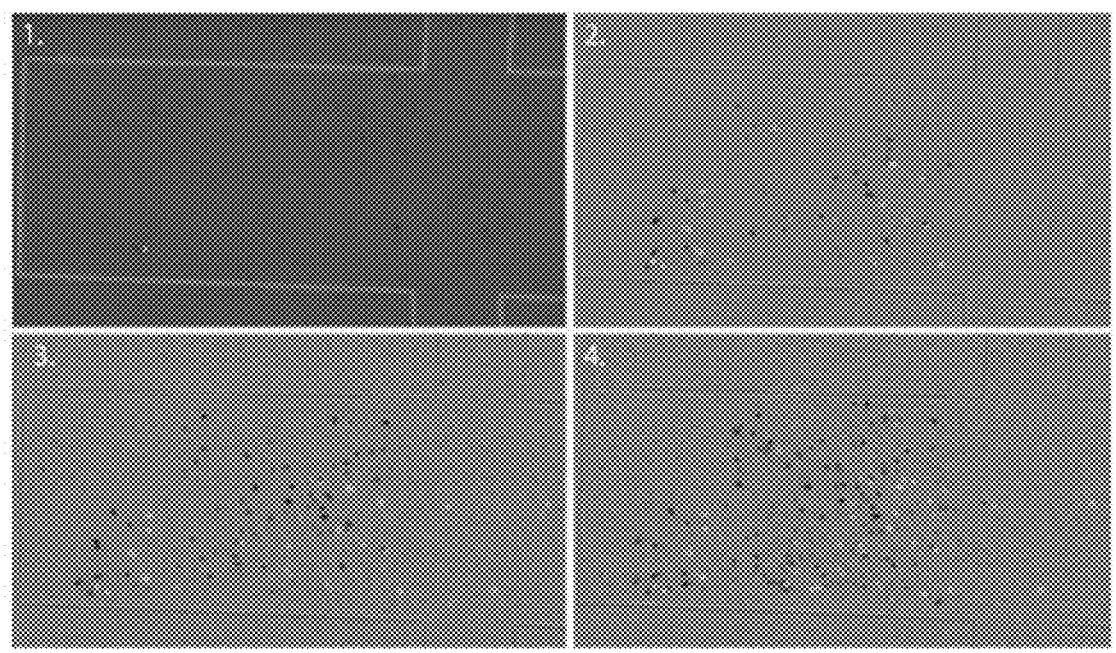
FIG. 29 shows an example of particle flow over a time course.

Once the chamber was saturated, the inoculation port was closed and the harvest output was enabled. Due to the dynamics of the flow through the chamber, the velocities and the influence on the particles in the chamber diminish drastically as they move away from the central axis (see FIG. 28. This, added to the effect of suction of the secondary circuit, keeps a population of microorganisms settled in the room multiplying (when using live organisms in place of the simulation used in this example). As its number increases, some microorganisms are displaced to a certain point near the central axis of the flow coming from port 4 and are dragged to port 2 (see FIG. 28). FIG. 29 shows the particle movement over a time course.

Example 5: Example Sandbox Bioreactor Unit

Figure 30A:
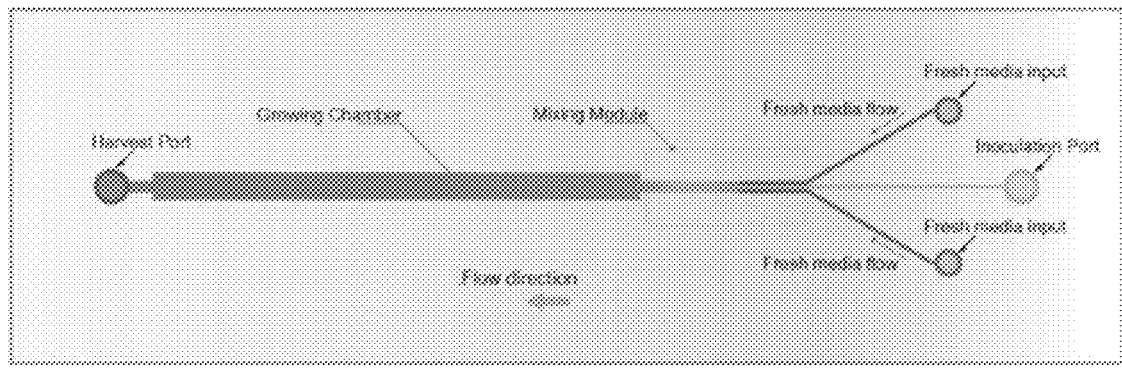
FIG. 30A shows an example sandbox unit with a mixing module.
Figure 30B:
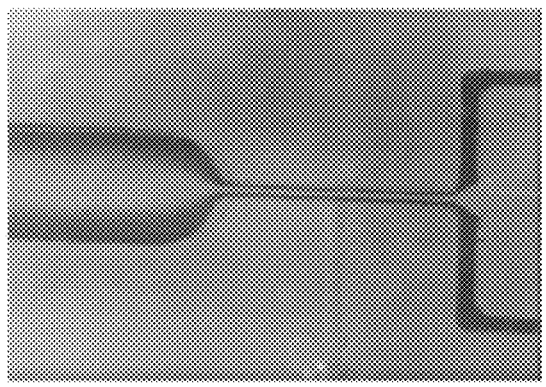
FIGS. 30B-30D show example sandbox units formed from polydimethylsiloxane.
Figure 30C:
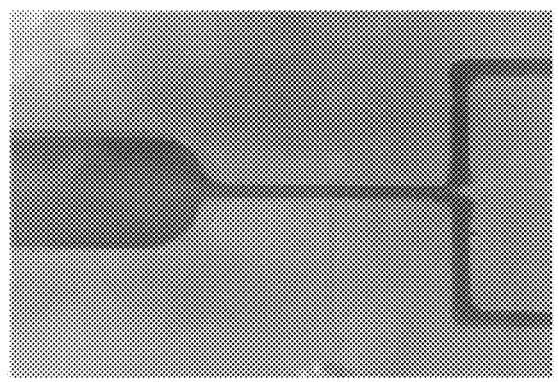
Figure 30D:
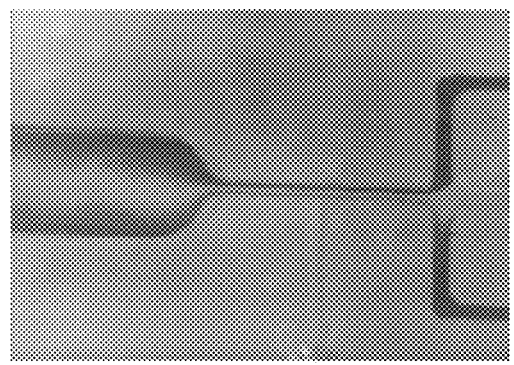

FIG. 30A shows the design of an example sandbox unit with a mixing module, single growth chamber and harvest port. FIGS. 30B-30D show a constructed unit fabricated from PDMS. In FIG. 30B, water (no color) was inoculated into the center channel at a flow rate of 985 microliters (μL) per hour, and water with blue dye was inoculated into each of the sides channels at a flow rate of 985 μL per hour. In FIG. 30C, water (no color) was inoculated into the center channel at a flow rate of 984 μL per hour, and water with blue dye was inoculated into each of the sides channels at a flow rate of 3335 μL per hour. FIG. 30C shows the module inoculated with an unbalanced flow between side channels.

Figure 31:
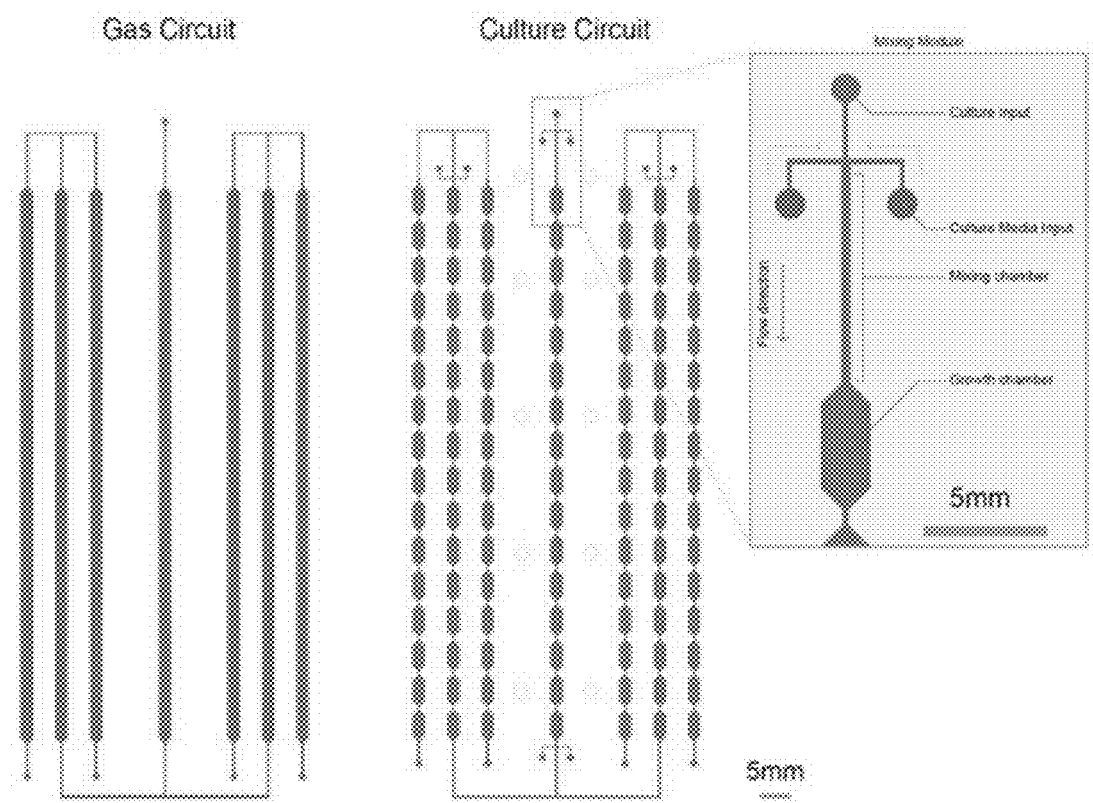
FIG. 31 shows a gas circuit and culture circuit for an example sandbox bioreactor.

Example 6: Construction of a Sandbox Bioreactor with Multiple Interconnected Units FIG. 31 shows the design of the culture circuit and the gas circuit for an example sandbox bioreactor module. The three layers of the module share a series of through-holes where screws, washers and nuts are adjusted to prevent leakage.

Figure 32:
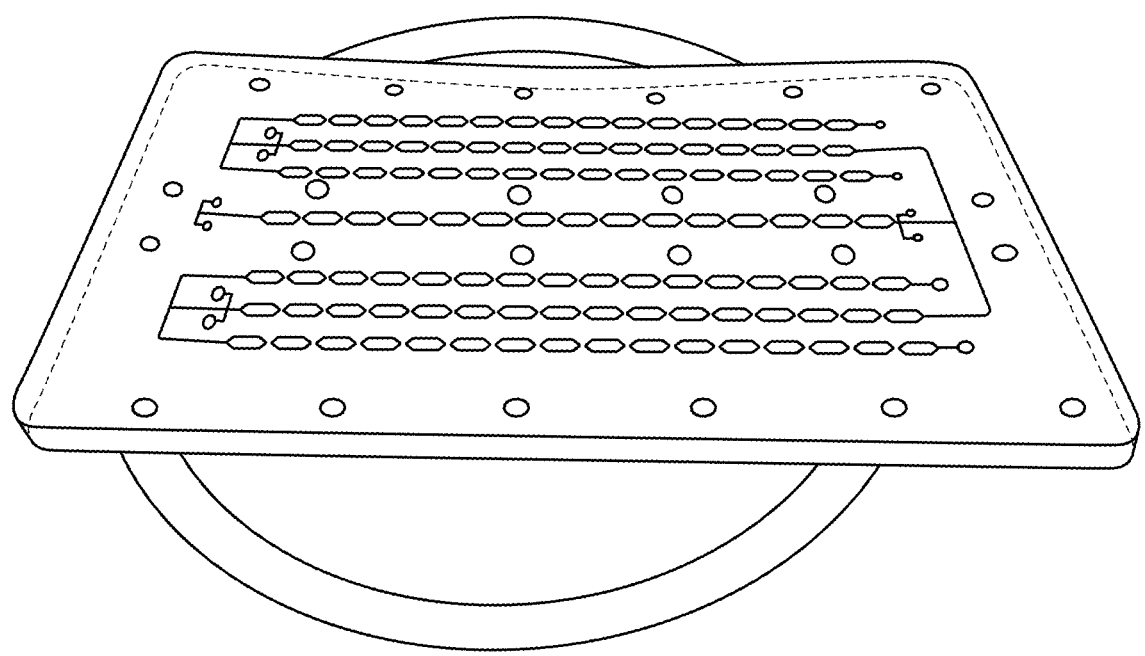
FIG. 32 shows an example printed culture layer of a sandbox.
Figure 33:
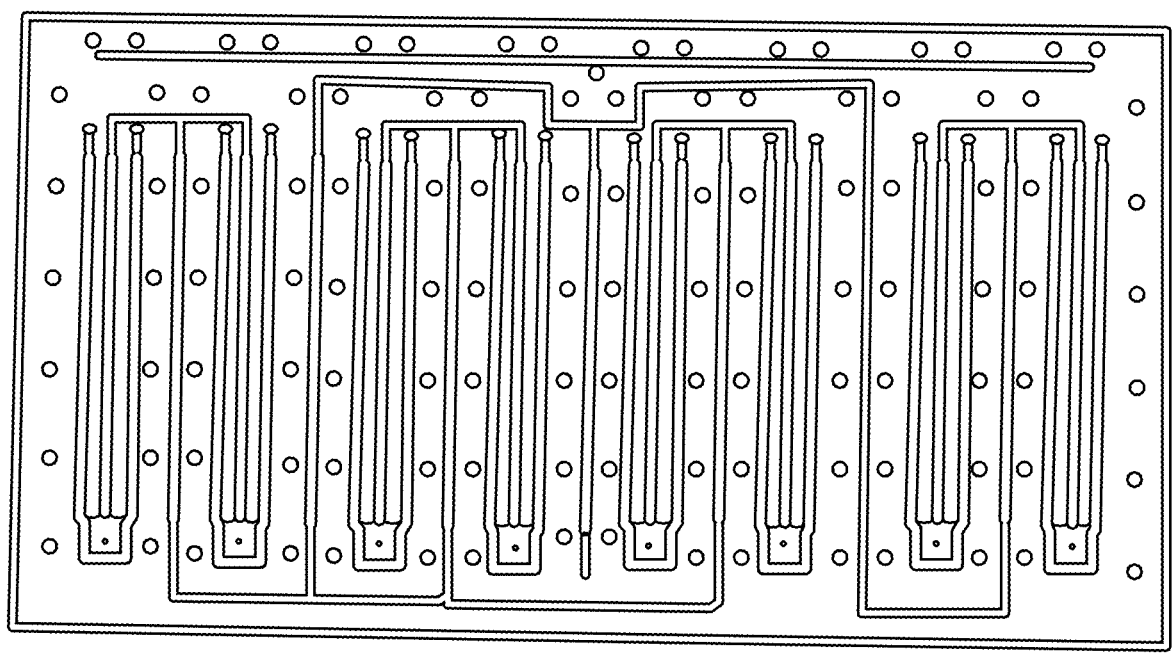
FIG. 33 shows assembled layers of an example sandbox.

The Culture Media distribution layer in this module is a compound distribution system formed with hoses. The hoses may have diameters between 50 and 500 micrometers and may be formed of biocompatible materials. The length of the hose was adjusted by calculating the load loss of the culture medium and comparing it with the pressure in each mixing module. A PDMS layer separates the gas layer and the culture layer. FIG. 32 shows the printed culture layer of the sandbox. FIG. 33 shows the assembled layers. Water with blue dye was used to inoculate the sandbox from the input port to show the flow through the sandbox module.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A bioreactor, comprising:
an inlet configured to receive a plurality of cells;
a macrostructure comprising a plurality of minimodules in fluid communication with the inlet, wherein a minimodule of the plurality of minimodules (i) comprises a gyroid structure, double gyroid structure, a modified gyroid structure, or a modified double gyroid structure and (ii) is fluidically connected to another minimodule of the plurality of minimodules via one or more connections to provide at least one microchannel configured to flow the plurality of cells, and wherein the modified gyroid structure or modified double gyroid structure comprises a modification to (1) a shape or (2) a connection of the one or more connections of the gyroid structure or double gyroid structure, respectively; and
an outlet in fluid communication with the plurality of minimodules, wherein the outlet is configured to direct the plurality of cells or cell products generated from the plurality of cells out of the at least one microchannel.

2. The bioreactor of claim 1, wherein the plurality of minimodules is connected in a manner to provide at least two non-overlapping microchannels each having a constant-mean-curvature.

3. The bioreactor of claim 2, wherein a first microchannel of the at least two non-overlapping microchannels is configured to flow a liquid medium, and wherein a second microchannel of the at least two non-overlapping microchannels is configured to flow a gas composition.

4. The bioreactor of claim 1, wherein the macrostructure is selected from the group consisting of a pyramid, a hollow pyramid, a lamella pyramid, a lamella, a chessboard arrangement, and a log.

5. The bioreactor of claim 1, further comprising (i) a cell input at a first end of the macrostructure configured to provide the plurality of cells to the inlet and (ii) a cell collection device at a second end of the macrostructure configured to harvest the plurality of cells from the outlet.

6. The bioreactor of claim 1, wherein the plurality of minimodules is generated using three-dimensional (3-D) printing.

7. A method for scaling production of cells, comprising:
introducing the plurality of cells into the inlet of the bioreactor of claim 1;
flowing a liquid medium into the bioreactor;
supplying a gas composition into the bioreactor; and
collecting the plurality of cells from the outlet of the bioreactor,
wherein the plurality of cells transit between minimodules of the plurality of minimodules, and wherein the plurality of cells transit from the inlet of the bioreactor to the outlet of the bioreactor.

8. The method of claim 7, wherein a cell of the plurality of cells is selected from the group consisting of a bacterial cell, a fungal cell, a yeast cell, a eukaryotic cell, a plant cell, and an algal cell.

9. A method for culturing cells, comprising:
(a) providing the plurality of cells to the bioreactor of claim 1, wherein the bioreactor comprises at least one channel and a microporous membrane;
(b) permitting at least a portion of the plurality of cells to adhere to a surface of the at least one channel such that the at least the portion of the plurality of cells replicate on the surface of the at least one channel to generate attached cells;
(c) flowing a liquid medium from the at least one channel through the microporous membrane to (i) wash the attached cells, (ii) detach the attached cells to generate suspended cells, or (iii) wash the suspended cells; and
(d) collecting the suspended cells.

10. The bioreactor of claim 1, wherein the minimodule of the plurality of minimodules comprises the gyroid structure.

11. The bioreactor of claim 1, wherein the minimodule of the plurality of minimodules comprises the modified gyroid structure.

12. The bioreactor of claim 1, wherein a liquid medium flowing through the at least one microchannel has a velocity greater than a free fall velocity of a cell flowing through the at least one microchannel.

13. The bioreactor of claim 4, wherein the plurality of minimodules is arranged in layers within the macrostructure.

14. The bioreactor of claim 13, further comprising a liquid medium input device configured to flow a liquid medium into each layer of the within the macrostructure such that a volume of liquid medium provided by the liquid medium input device to each layer maintains a substantially constant cell density in each of the layers.

15. The method of claim 7, wherein the plurality of minimodules is arranged in layers forming a macrostructure, and wherein the plurality of cells divides on average one time during the transit from one layer to a next layer of the macrostructure.

16. The method of claim 15, wherein an amount of liquid medium flowing in each layer of the layers maintains substantially the same density of cells in each layer.

17. The method of claim 9, wherein the at least one channel comprises a material suitable for adhesion of the at least the portion of the plurality of cells.

18. The method of claim 9, further comprising flowing an additional liquid medium through the at least one channel to (i) provide a culture medium to permit growth or replication of the at least the portion of the plurality of cells, (ii) detach the attached cells from the at least one channel, or (iii) flow the suspended cells from the at least one channel to a collection area.

* * * * *

UNITED STATES PATENT AND TRADEMARK OFFICE
CERTIFICATE OF CORRECTION

| | |
|---|---|
| PATENT NO. | : 12,331,274 B2 |
| APPLICATION NO. | : 17/225307 |
| DATED | : June 17, 2025 |
| INVENTOR(S) | : Juan Francisco Llamazares Vegh |

Page 1 of 1

It is certified that error appears in the above-identified patent and that said Letters Patent is hereby corrected as shown below:

On the Title Page

Item (12), "Llamazares" should read --Llamazares Vegh--

Item (72), Inventor: "Juan Francisco Llamazares, San Francisco, CA (US)" should read --Juan Francisco Llamazares Vegh, San Francisco, CA (US)--

Signed and Sealed this
Fifteenth Day of July, 2025

Coke Morgan Stewart
*Acting Director of the United States Patent and Trademark Office*